US011033266B2

(12) United States Patent
Jones et al.

(10) Patent No.: US 11,033,266 B2
(45) Date of Patent: Jun. 15, 2021

(54) DECOUPLING MECHANISM FOR LINEAR SURGICAL STAPLER

(71) Applicant: ETHICON LLC, Guaynabo, PR (US)

(72) Inventors: Jason Jones, Cincinnati, OH (US); Carol J. Wynn, Kings Mills, OH (US); Matthew S. Corbin, Loveland, OH (US); Brian D. Schings, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 317 days.

(21) Appl. No.: 16/165,587

(22) Filed: Oct. 19, 2018

(65) Prior Publication Data

US 2020/0046351 A1 Feb. 13, 2020

Related U.S. Application Data

(63) Continuation-in-part of application No. 16/102,164, filed on Aug. 13, 2018, now Pat. No. 10,898,187.

(51) Int. Cl.
*A61B 17/072* (2006.01)
*A61B 17/00* (2006.01)
(Continued)

(52) U.S. Cl.
CPC ...... *A61B 17/072* (2013.01); *A61B 17/07207* (2013.01); *A61B 17/068* (2013.01);
(Continued)

(58) Field of Classification Search
CPC ............... A61B 17/068; A61B 17/072; A61B 17/07207; A61B 17/115; A61B 17/2833;
(Continued)

(56) References Cited

U.S. PATENT DOCUMENTS 4,520,817 A * 6/1985 Green ............... A61B 17/07207
227/176.1
4,863,088 A * 9/1989 Redmond ........ A61B 17/07207
227/19
(Continued)

FOREIGN PATENT DOCUMENTS

CN 202 875 415 U 4/2013
EP 0061466 A1 10/1982
(Continued)

OTHER PUBLICATIONS

U.S. Appl. No. 16/102,164.
(Continued)

*Primary Examiner* — Scott A Smith
(74) *Attorney, Agent, or Firm* — Frost Brown Todd LLC

(57) ABSTRACT

A surgical stapler includes a first elongate member having a distal portion that supports a plurality of staple forming pockets, a second elongate member having a distal portion that receives a staple cartridge, and a clamp member operable to releasably clamp the first and second elongate members together. A retaining member is provided on one of the first elongate member or the second elongate member and is configured to releasably couple proximal ends of the first and second elongate members together with a resilient bias such that the first and second elongate members are pivotable relative to one another at the proximal ends. A decoupling mechanism is configured to overcome the resilient bias of the retaining member and thereby decouple the proximal ends from one another in response to the first and second elongate members being pivoted away from one another.

15 Claims, 34 Drawing Sheets

(51) Int. Cl.
 *A61B 17/28* (2006.01)
 *A61B 17/068* (2006.01)

(52) U.S. Cl.
 CPC . *A61B 17/2833* (2013.01); *A61B 2017/00477* (2013.01); *A61B 2017/00862* (2013.01); *A61B 2017/07214* (2013.01); *A61B 2017/07264* (2013.01); *A61B 2017/07271* (2013.01); *A61B 2017/07278* (2013.01)

(58) Field of Classification Search
 CPC ...... A61B 17/2841; A61B 2017/00477; A61B 2017/07214; A61B 2017/07271
 USPC .............. 227/19, 176.1, 175.1, 175.2, 180.1; 606/1, 139, 219
 See application file for complete search history.

(56) References Cited

U.S. PATENT DOCUMENTS

| | | | |
|---|---|---|---|
| 4,991,764 | A | 2/1991 | Mericle |
| 5,141,144 | A | 8/1992 | Foslien |
| 5,636,779 | A | 6/1997 | Palmer |
| 5,792,135 | A | 8/1998 | Madhani et al. |
| 5,817,084 | A | 10/1998 | Jensen |
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,783,524 | B2 | 8/2004 | Anderson et al. |
| 7,524,320 | B2 | 4/2009 | Tierney et al. |
| 7,631,794 | B2 * | 12/2009 | Rethy .............. A61B 17/07207 227/175.1 |
| 7,691,098 | B2 | 4/2010 | Wallace et al. |
| 7,806,891 | B2 | 10/2010 | Nowlin et al. |
| 7,905,381 | B2 | 3/2011 | Baxter, III et al. |
| 7,954,686 | B2 | 6/2011 | Baxter, III et al. |
| 8,348,129 | B2 | 1/2013 | Bedi et al. |
| 8,479,969 | B2 | 7/2013 | Shelton, IV |
| 8,523,041 | B2 | 9/2013 | Ishitsuki et al. |
| 8,573,461 | B2 | 11/2013 | Shelton, IV et al. |
| 8,573,465 | B2 | 11/2013 | Shelton, IV |
| 8,602,288 | B2 | 12/2013 | Shelton, IV et al. |
| 8,616,431 | B2 | 12/2013 | Timm et al. |
| 8,783,541 | B2 | 7/2014 | Shelton, IV et al. |
| 8,789,740 | B2 | 7/2014 | Baxter, III et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 9,155,537 | B2 | 10/2015 | Katre et al. |
| 9,301,759 | B2 | 4/2016 | Spivey et al. |
| 9,402,629 | B2 | 8/2016 | Ehrenfels et al. |
| 9,539,007 | B2 | 1/2017 | Dhakad et al. |
| 9,724,095 | B2 | 8/2017 | Gupta et al. |
| 10,898,187 | B2 * | 1/2021 | Deck .................... A61B 17/072 |
| 2006/0219752 | A1 * | 10/2006 | Arad ................ A61B 17/07207 227/176.1 |
| 2009/0173766 | A1 * | 7/2009 | Wenchell ............ A61B 17/068 227/178.1 |
| 2009/0308907 | A1 | 12/2009 | Nalagatla et al. |
| 2012/0143218 | A1 | 6/2012 | Beardsley et al. |
| 2012/0312858 | A1 * | 12/2012 | Patankar .......... A61B 17/07207 227/176.1 |
| 2013/0172929 | A1 | 7/2013 | Hess et al. |
| 2013/0306703 | A1 * | 11/2013 | Ehrenfels ......... A61B 17/07207 227/175.2 |
| 2014/0353357 | A1 | 12/2014 | Agarwal et al. |
| 2015/0018875 | A1 | 1/2015 | Knodel |
| 2015/0034695 | A1 | 2/2015 | Kapadia |
| 2015/0327855 | A1 | 11/2015 | Katre |
| 2016/0135811 | A1 | 5/2016 | Gupta et al. |
| 2016/0249920 | A1 | 9/2016 | Gupta et al. |
| 2016/0262756 | A1 | 9/2016 | Patankar et al. |
| 2016/0310136 | A1 | 10/2016 | Gupta et al. |
| 2016/0338701 | A1 | 11/2016 | Patankar et al. |
| 2016/0338702 | A1 | 11/2016 | Ehrenfels et al. |
| 2017/0079652 | A1 | 3/2017 | Dhakad et al. |
| 2017/0143335 | A1 | 5/2017 | Gupta et al. |
| 2017/0143336 | A1 | 5/2017 | Shah et al. |
| 2017/0325811 | A1 | 11/2017 | Gupta et al. |

FOREIGN PATENT DOCUMENTS

| | | |
|---|---|---|
| EP | 0178941 B1 | 4/1986 |
| EP | 0677273 B1 | 10/1995 |
| EP | 1702567 B1 | 9/2006 |
| EP | 2 018 826 A2 | 1/2009 |
| EP | 2532312 B1 | 12/2012 |
| EP | 3065649 A1 | 9/2016 |
| EP | 2741685 B1 | 1/2017 |
| EP | 3155988 A1 | 4/2017 |
| EP | 2804541 B1 | 10/2017 |
| EP | 3 289 985 A1 | 3/2018 |
| EP | 3 520 710 A1 | 8/2019 |
| EP | 3 520 711 A1 | 8/2019 |
| WO | WO 2015/174984 A1 | 11/2015 |
| WO | WO 2017/056028 A1 | 4/2017 |
| WO | WO 2018/044669 A1 | 3/2018 |

OTHER PUBLICATIONS

U.S. Appl. No. 15/889,363, entitled "Release Mechanism for Linear Surgical Stapler," filed Feb. 6, 2018.
U.S. Appl. No. 15/889,370, entitled "Lockout Assembly for Linear Surgical Stapler," filed Feb. 6, 2018.
U.S. Appl. No. 15/889,374, entilted "Features to Align and Close Linear Surgical Stapler," filed Feb. 6, 2018.
U.S. Appl. No. 15/889,376, entitled "Releasable Coupling Features for Proximal Portions of Linear Surgical Stapler," filed Feb. 6, 2018.
U.S. Appl. No. 15/889,388, entitled "Firing Lever Assembly for Linear Surgical Stapler," filed Feb. 6, 2018.
U.S. Appl. No. 15/889,390, entitled "Clamping Mechanism for Linear Surgical Stapler," filed Feb. 6, 2018.
U.S. Appl. No. 16/102,164, entitled "Firing System for Linear Surgical Stapler," filed Aug. 13, 2018.
U.S. Appl. No. 16/102,170, entitled "Clamping Assembly for Linear Surgical Stapler," filed Aug. 13, 2018.
U.S. Appl. No. 16/157,599, entitled "Anvil Assembly for Linear Surgical Stapler," filed Oct. 11, 2018.
U.S. Appl. No. 16/157,605, entitled "Closure Assembly for Linear Surgical Stapler," filed Oct. 11, 2018.
European Search Report, Extended, and Written Opinion dated Dec. 2, 2019 for Application No. EP 19191312.8, 12 pgs.
European Search Report, Partial, and Provisional Written Opinion dated Jan. 3, 2020 for Application No. EP 19204124.2, 19 pgs.
International Search Report and Written Opinion dated Nov. 29, 2019 for Application No. PCT/IB2019/056697, 16 pgs.
International Serach Report and Written Opinion dated Jul. 7, 2020 for Application No. PCT/IB2019/058696, 22 pgs.

* cited by examiner

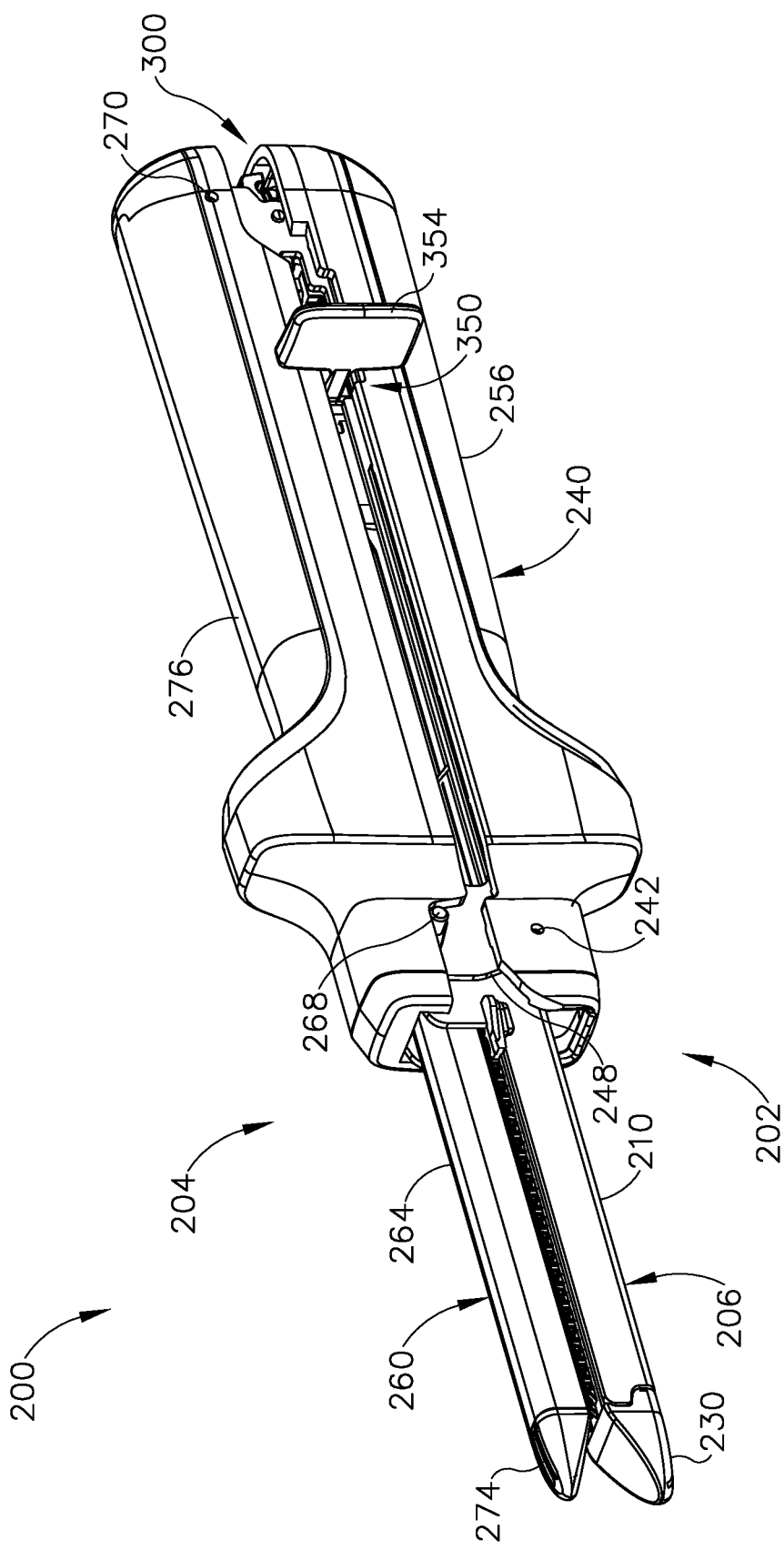

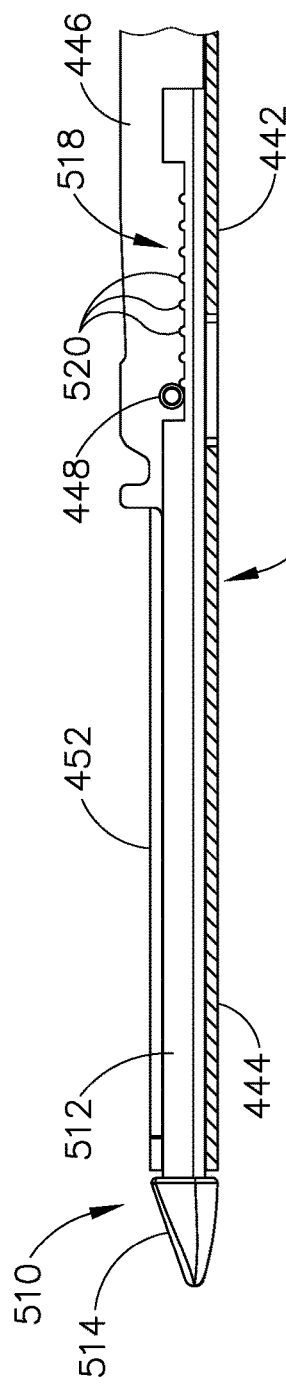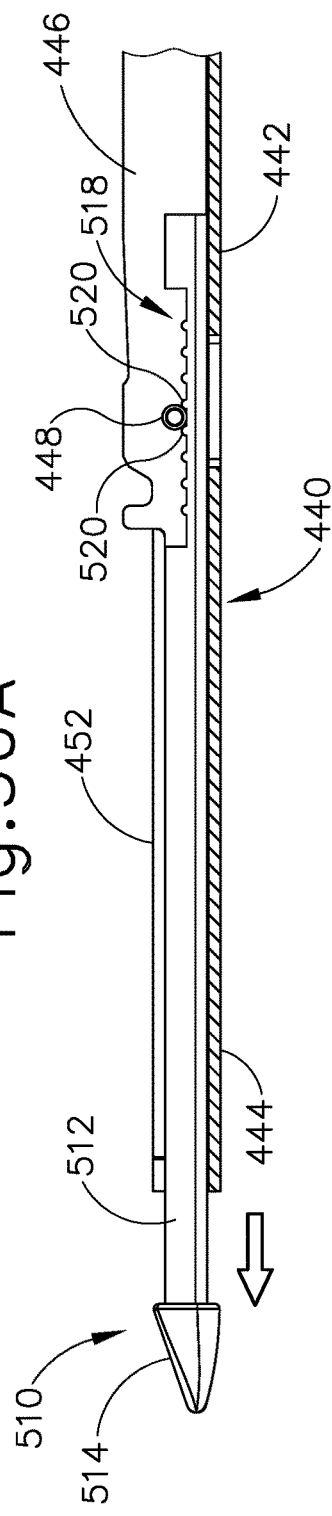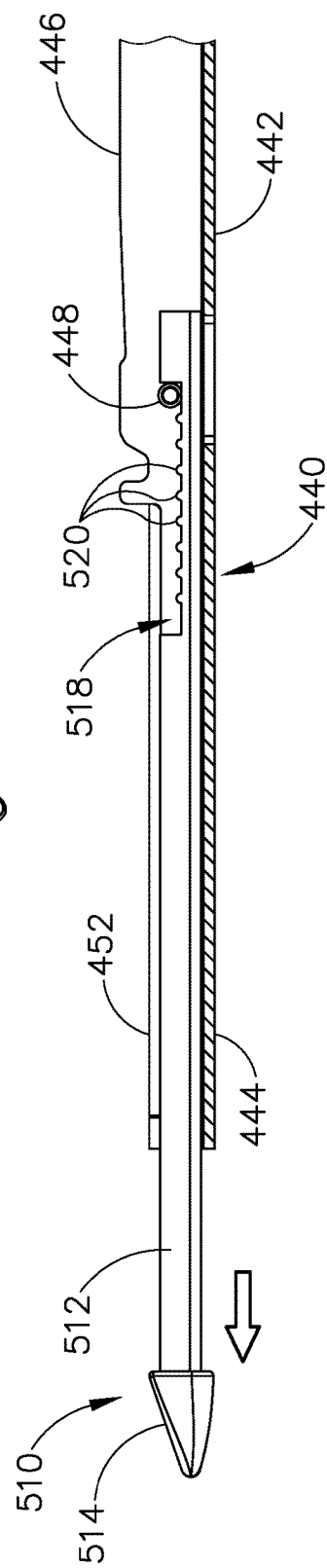

DECOUPLING MECHANISM FOR LINEAR SURGICAL STAPLER

This application is a continuation-in-part of U.S. patent application Ser. No. 16/102,164, entitled "Firing System for Linear Surgical Stapler," filed Aug. 13, 2018, now U.S. Pat. No. 10,898,187, the disclosure of which is incorporated by reference herein in its entirety.

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 6 depicts a distal perspective view of another exemplary linear surgical stapler, showing a cartridge half and an anvil half of the stapler coupled together with a clamp lever of the cartridge half in a fully closed position;

FIG. 30A depicts a side cross-sectional view of the distal portion of the linear surgical stapler of FIG. 22, showing the extendable tip member in a fully retracted position;

FIG. 30B depicts a side cross-sectional view of the distal portion of the linear surgical stapler of FIG. 22, showing the extendable tip member in an intermediate extended position;

FIG. 30C depicts a side cross-sectional view of the distal portion of the linear surgical stapler of FIG. 22, showing the extendable tip member in a fully extended position;

Figure 1:
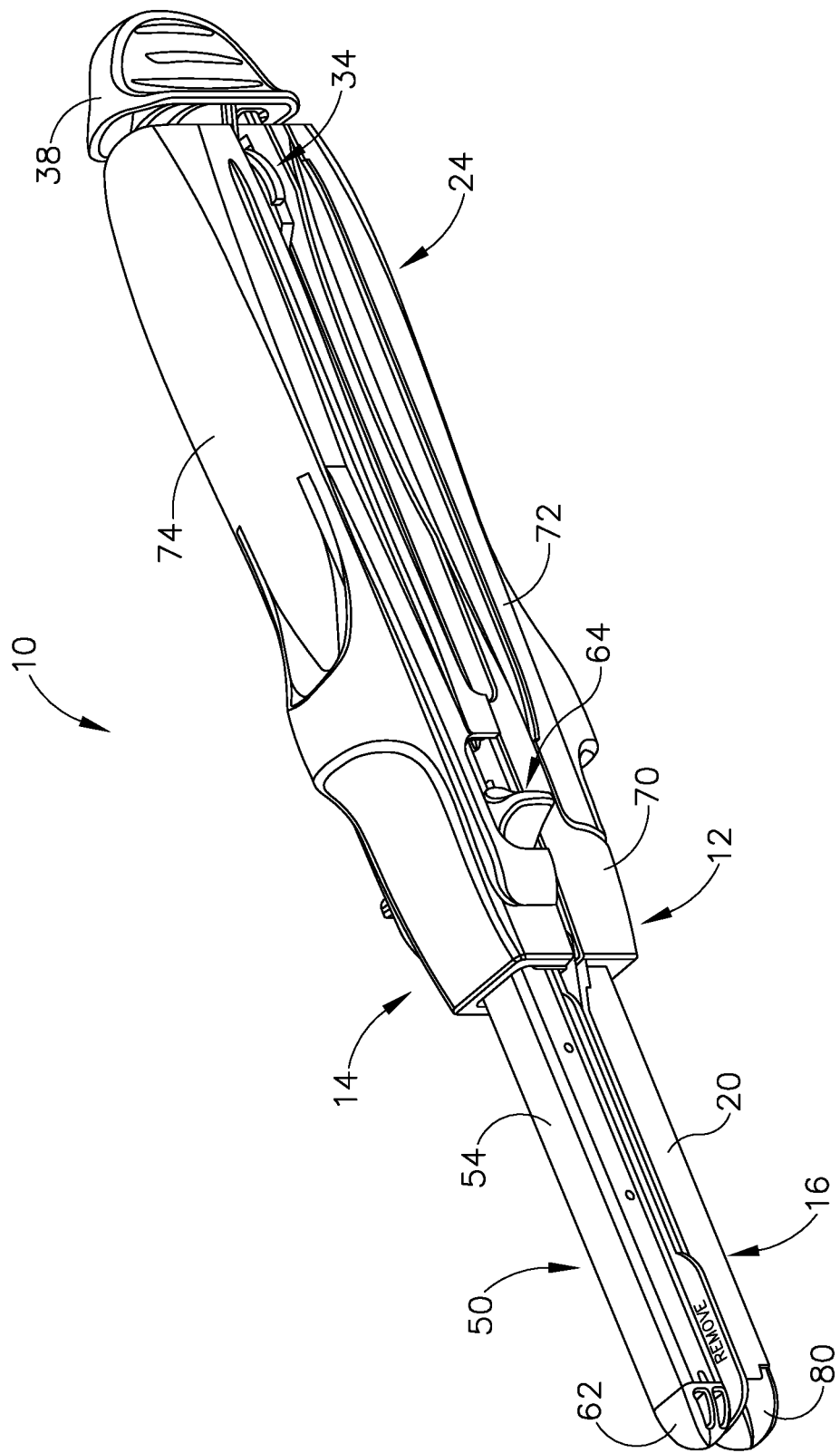
FIG. 1 depicts a distal perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
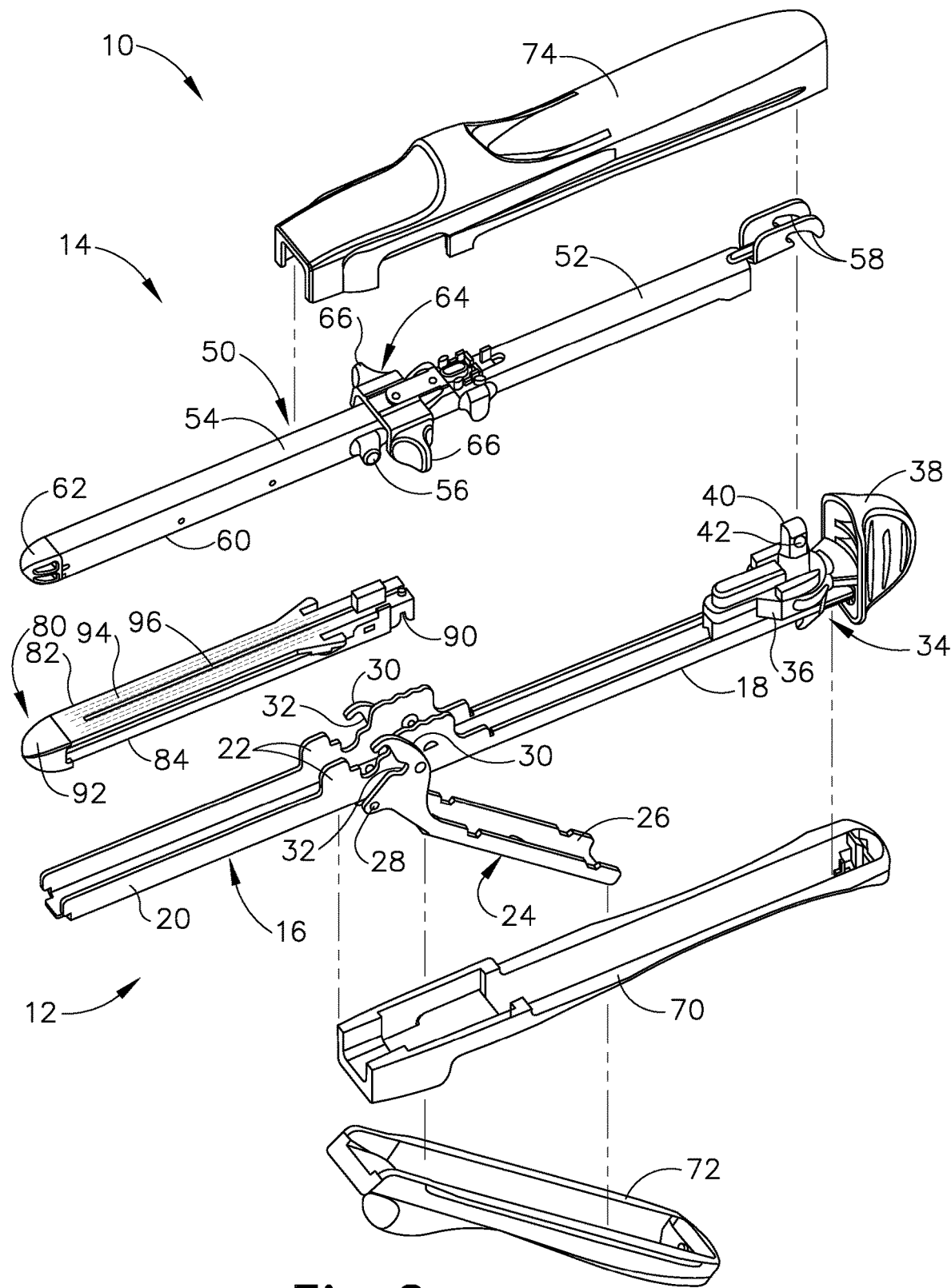
FIG. 2 depicts an exploded perspective view of the linear surgical stapler of FIG. 1.

FIGS. 1 and 2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween. Cartridge half (12) includes an elongate cartridge channel (16) having a proximal frame portion (18) that slidably retains a portion of a firing assembly (34), a distal jaw portion (20) that supports a staple cartridge (80) (or "reload"), and a pair of upright side flanges (22) arranged medially therebetween.

Cartridge half (12) further includes a clamp lever (24) pivotably coupled to an underside of cartridge channel (16) in approximate alignment with side flanges (22). Clamp lever (24) includes an elongate lever arm (26) having a free proximal end and a distal end that is pivotably coupled to cartridge channel (16) with a pivot pin (28). A pair of opposed jaws (30) extends distally from the distal end of lever arm (26) alongside flanges (22) of cartridge channel (16). Each jaw (30) includes a respective elongate slot (32) having a closed proximal end and an open distal end, and which defines upper and lower camming surfaces configured to engage a respective latch projection (56) of anvil half (14). As described below, clamp lever (24) is operable to pivot relative to cartridge channel (16) between open and closed positions to releasably clamp anvil half (14) against cartridge half (12) and thereby capture tissue layers therebetween.

As shown best in FIG. 2, firing assembly (34) of cartridge half (12) includes a slider block (36) slidably retained within proximal frame portion (18) of cartridge channel (16), an actuator (38) (or "firing knob") movably coupled with slider block (36), and an elongate actuating beam (not shown) extending distally from slider block (36) and configured to couple with a sled (100) (see FIG. 3) housed within staple cartridge (80). Actuator (38) of the present example is configured to pivot about the proximal end of cartridge half (12) to provide for "dual-sided firing" of stapler (10). Specifically, actuator (38) may be positioned along either lateral side of cartridge half (12) to perform a distal firing stroke, such that stapler (10) may be conveniently fired in a variety of orientations during a surgical procedure.

Figure 5A:
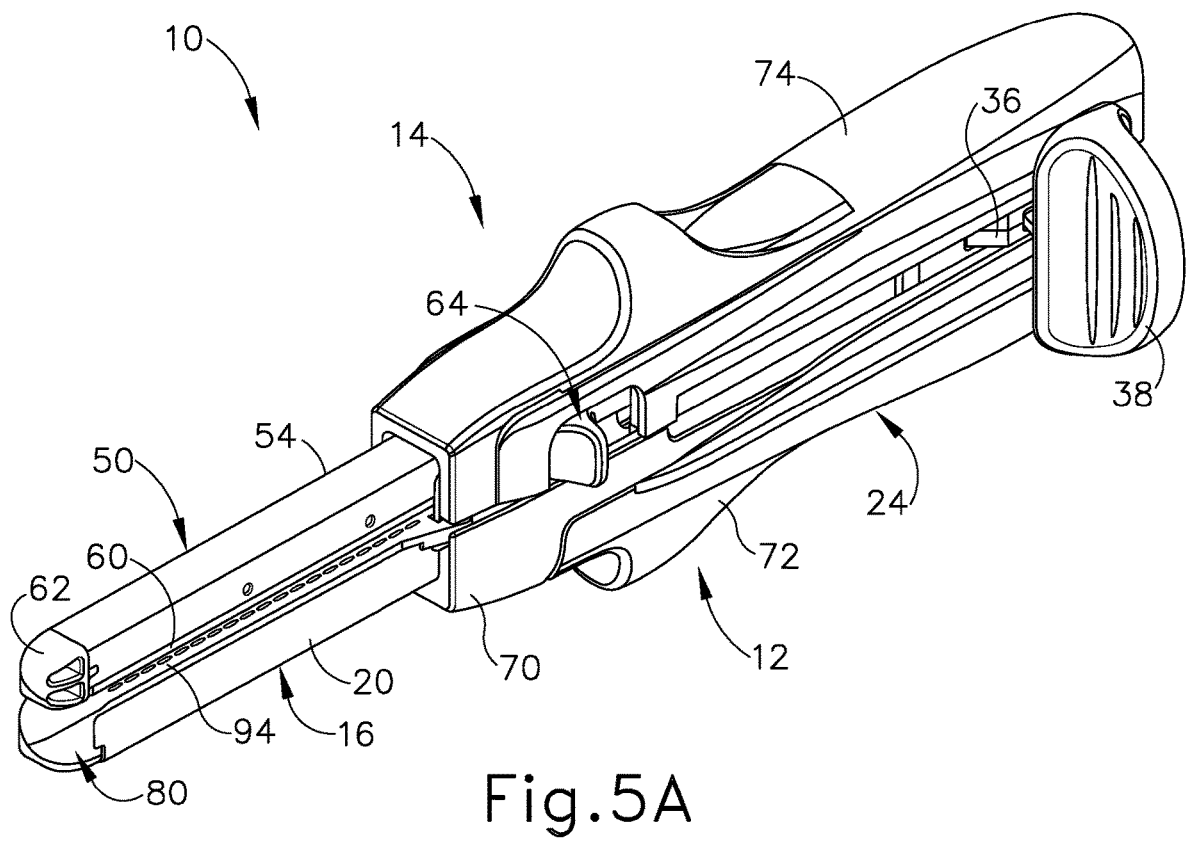
FIG. 5A depicts a distal perspective view of the linear surgical stapler of FIG. 1, showing an actuator of the stapler in a proximal, pre-fired position.
Figure 5B:
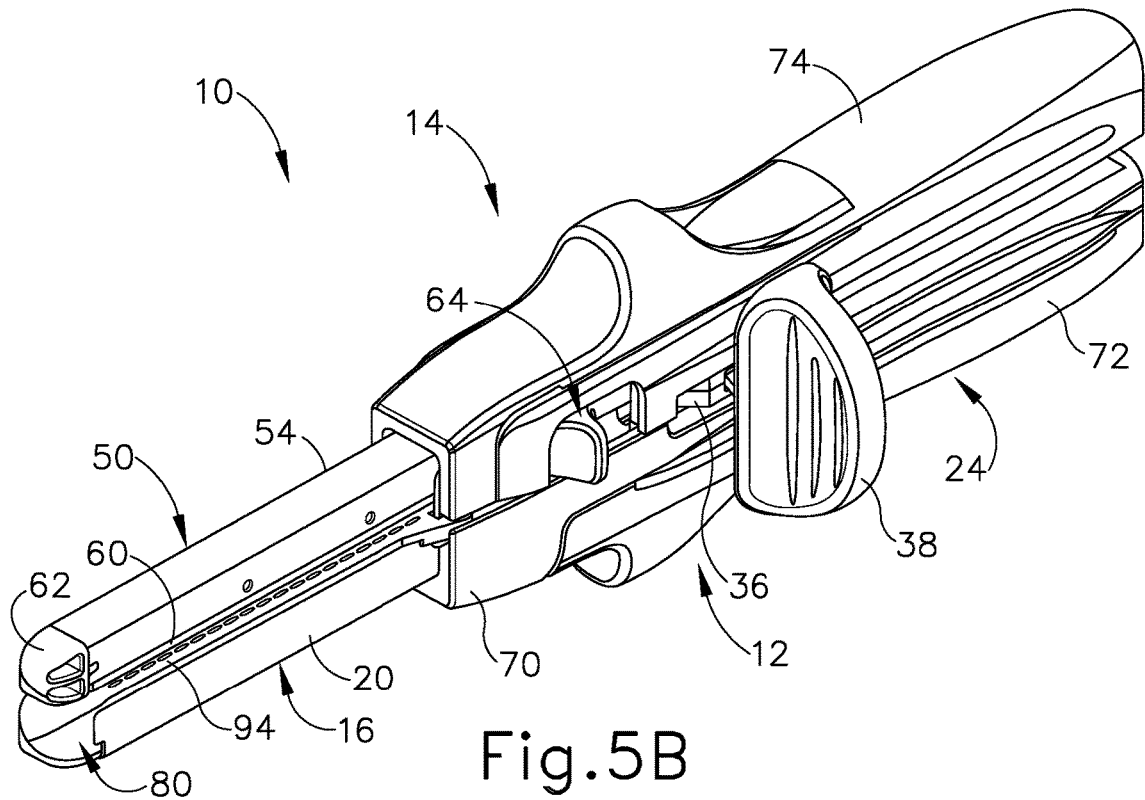
FIG. 5B depicts a distal perspective view of the linear surgical stapler of FIG. 1, showing the actuator in a distal, fired position.

Slider block (36) is configured to be translatably driven within proximal frame portion (18) by actuator (38) between a proximal home position shown in FIGS. 2 and 5A, and a distal fired position shown in FIG. 5B. In the proximal home position, slider block (36) abuts a post (40) fixed at a proximal end of cartridge channel (16). A free end of post (40) supports a laterally extending pivot pin (42). As described below, actuator (38) may be driven distally when stapler halves (12, 14) are fully coupled together and clamp lever (24) is closed. Distal advancement of actuator (38) along either lateral side of stapler (10) drives slider block (36) and the elongate actuating beam distally, which in turn drives sled (100) distally through staple cartridge (80). As described below, distal translation of sled (100) through staple cartridge (80) provides for simultaneous stapling and cutting of tissue clamped between stapler halves (12, 14).

As shown best in FIGS. 1 and 2, anvil half (14) of linear surgical stapler (10) includes an elongate anvil channel (50) having a proximal frame portion (52) and a distal jaw portion (54). Anvil channel (50) further includes a latch feature in the form of a pair of projections (56) that extend transversely from a medial portion of anvil channel (50) in a direction toward cartridge half (12). Each latch projection (56) may include a circular rotating cap configured to be captured within the slot (32) of a respective clamp lever jaw (30) when anvil half (14) is coupled with cartridge half (12) and clamp lever (24) is pivoted from the open position to the closed position, as described below. A pair of hooks (58) extend proximally from a proximal end of frame portion

(52) and are configured to releasably capture opposed lateral ends of proximal pivot pin (42) of cartridge half (12). Distal jaw portion (54) supports an anvil surface in the form of an anvil plate (60) having a plurality of staple forming pockets (not shown), and additionally supports a distal tip member (62). In other versions of stapler (10), the anvil surface may be formed integrally with or otherwise be rigidly connected to distal jaw portion (54) of anvil channel (50).

Anvil half (14) of the present example further includes a staple height adjustment mechanism (64) mounted to a medial portion of anvil channel (50). Staple height adjustment mechanism (64) is operatively coupled with anvil plate (60), for example via one or more camming features (not shown), and includes a pair of user-engageable projections (66). Longitudinal adjustment of projections (66) between a plurality of predetermined positions causes anvil plate (60) to move transversely relative to distal jaw portion (54) of anvil channel (50). This enables adjustment of a transverse gap distance between anvil plate (60) and a deck (94) of staple cartridge (80) that defines the height of staples being formed. A larger gap distance, and thus a greater staple height, may be set when stapling tissues of greater thicknesses. Conversely, a smaller gap distance, and thus a smaller staple height, may be set when stapling tissues of lesser thicknesses. It will be appreciated that staple height adjustment mechanism (64) may be omitted in some versions, in which case the anvil surface may be fixed relative to anvil channel (50). For instance, the anvil surface may be formed integrally with or otherwise fixedly secured to distal jaw portion (54).

As shown best in in FIGS. 1 and 2, linear surgical stapler (10) further includes a plurality of shrouds (70, 72, 74) that cover select portions of stapler (10) and promote effective grip and manipulation of stapler (10) by an operator during use. In the present example, cartridge half (12) includes a first shroud (70) that covers an outwardly facing side of proximal frame portion (18) of cartridge channel (16). Cartridge half (12) further includes a second shroud (72) that covers an outwardly facing side of clamp lever (24) and is configured to pivot with clamp lever (24) relative to cartridge channel (16) and first shroud (70). Anvil half (14) includes a third shroud (74) that covers an outwardly facing side of proximal frame portion (52) of anvil channel (50), including proximal hooks (58). Each shroud (70, 72, 74) may be coupled with its respective components of stapler (10) by any suitable means apparent to those of ordinary skill in the art. Additionally, each shroud (70, 72, 74) may be formed of one or more materials and be provided with texturing suitable to promote effective gripping of the shroud (70, 72, 74) by an operator to enable safe and efficient use of stapler (10) during a surgical procedure.

Figure 3:
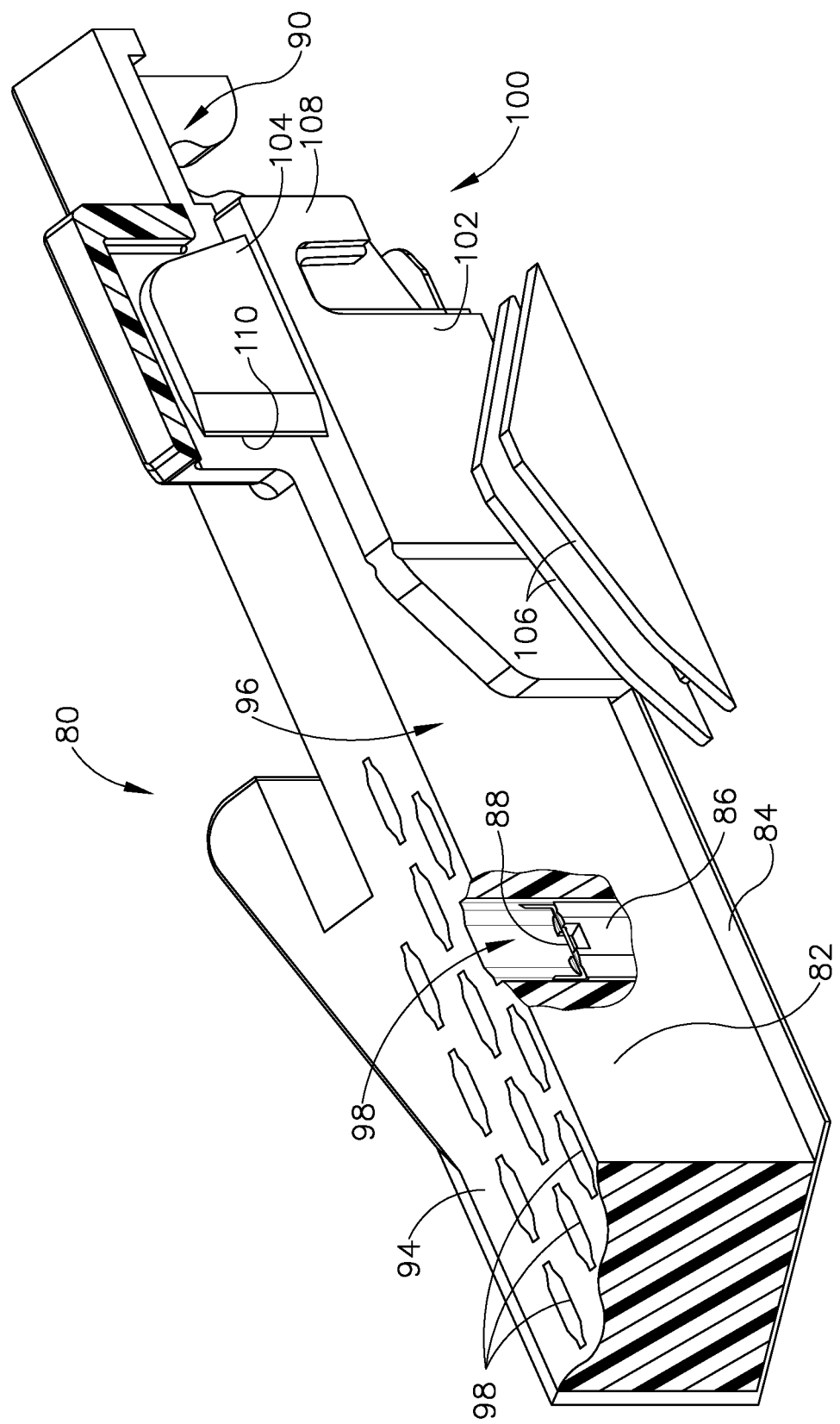
FIG. 3 depicts a cross-sectional perspective view of a staple cartridge assembly of the linear surgical stapler of FIG. 1.

As shown in FIGS. 2 and 3, staple cartridge (80) of the present example is an assembly that comprises a cartridge body (82), a pan (84) that covers an open lower side of cartridge body (82), and a plurality of staple drivers (86) housed within cartridge body (82) and each being configured to drive a respective staple (88). Cartridge body (82) includes a proximal end having coupling features (90) configured to releasably engage corresponding coupling features (not shown) of distal jaw portion (20) of cartridge channel (16), and a distal end defining a tapered nose (92). An upper side of cartridge body (82) defines a generally planar deck (94) through which a longitudinal slot (96) and a plurality of staple cavities (98) open. Each staple cavity (98) houses a respective staple driver (86) and a staple (88). As shown in FIG. 3, an interior of cartridge body (82) slidably houses a sled (100) that comprises a sled body (102) and knife member (104). Lateral sides of sled body (102) support a plurality of cam ramps (106) that taper distally. A proximal end of sled body (102) includes a downwardly extending tab (108) configured to lockingly engage a distal end of the elongate actuating beam (not shown) of firing assembly (34) when staple cartridge (80) is mounted to cartridge half (12) of stapler (10). Knife member (104) extends upwardly from an upper side of sled body (102) and presents a distally facing cutting edge (110) configured to cut tissue.

Sled (100) is configured to translate distally through cartridge body (82) in response to distal actuation of firing assembly (34), such that knife member (104) translates distally through longitudinal slot (96) to cut tissue clamped between stapler halves (12, 14). Simultaneously, cam ramps (106) translate distally through respective interior slots (not shown) of cartridge body (82) to actuate staple drivers (86) and staples (88) upwardly through staple cavities (98) so that free ends of staples (88) pierce through the clamped tissue and deform against staple forming pockets of anvil plate (60). In this manner, distal actuation of firing assembly (34) provides for simultaneous severing and stapling of tissue clamped between the distal end effector portions of stapler halves (12, 14).

Linear surgical stapler (10) and staple cartridge (80) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and/or U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Surgical Stapler

Figure 4A:
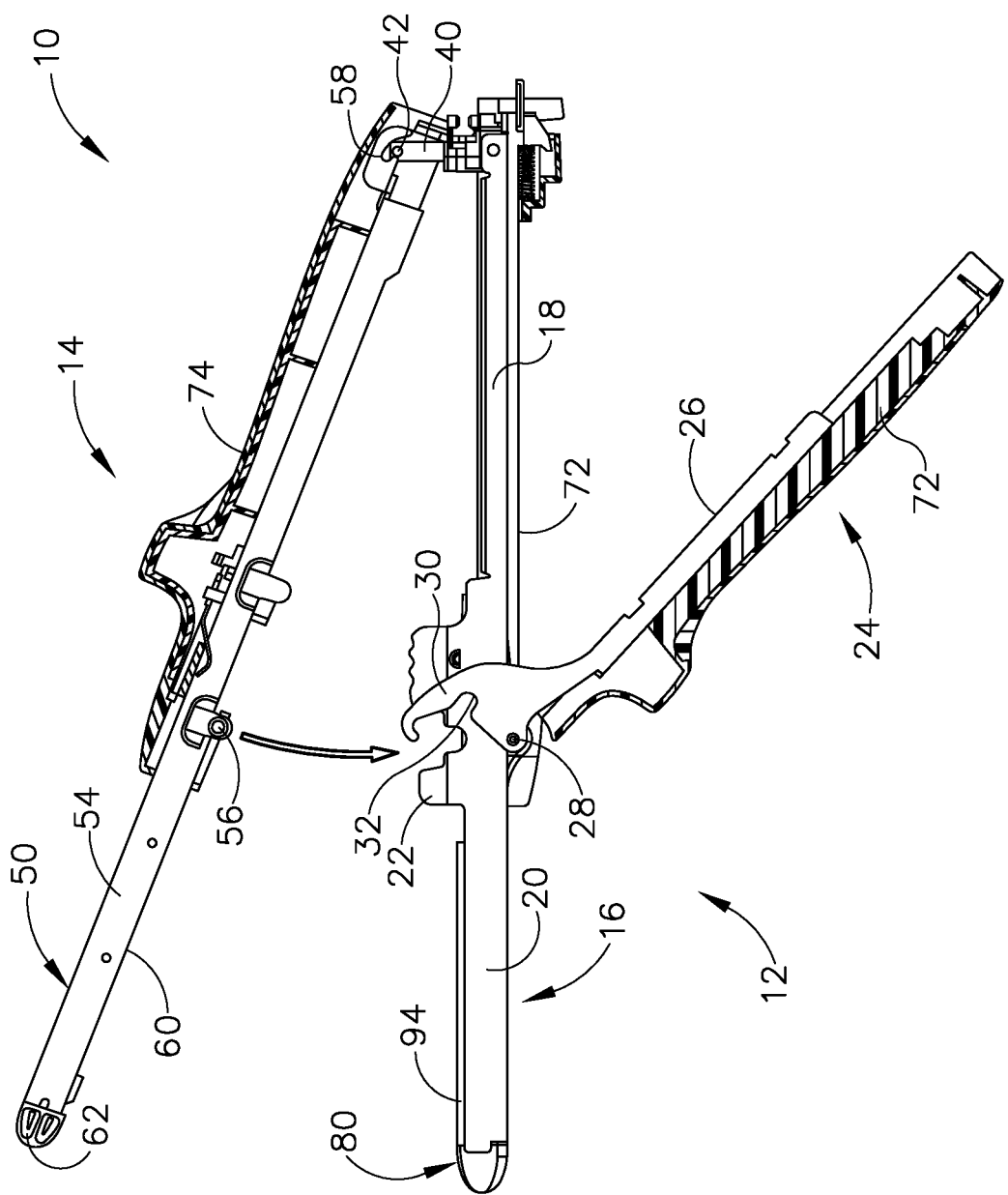
FIG. 4A depicts a cross-sectional side view of the linear surgical stapler of FIG. 1, showing the stapler halves coupled together at their proximal ends with the clamp lever in an open position.
Figure 4B:
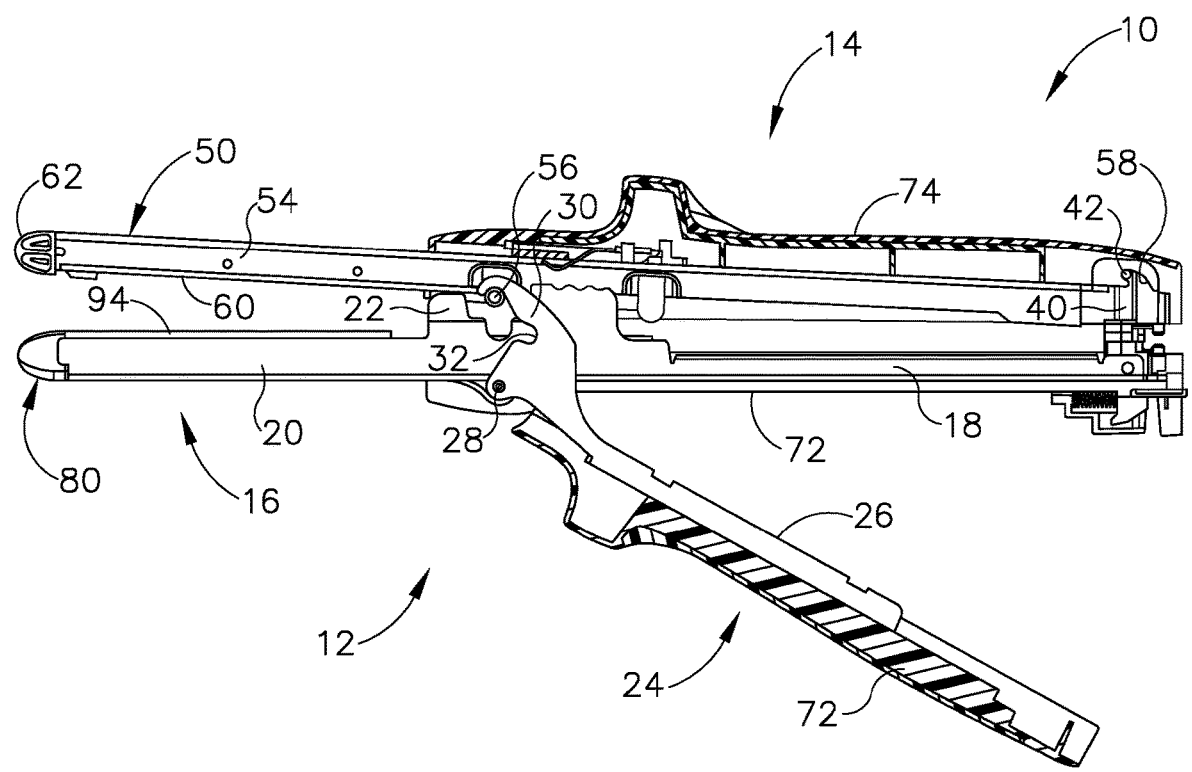
FIG. 4B depicts a cross-sectional side view of the linear surgical stapler of FIG. 1, showing the stapler halves coupled together with the clamp lever in a partially closed position.
Figure 4C:
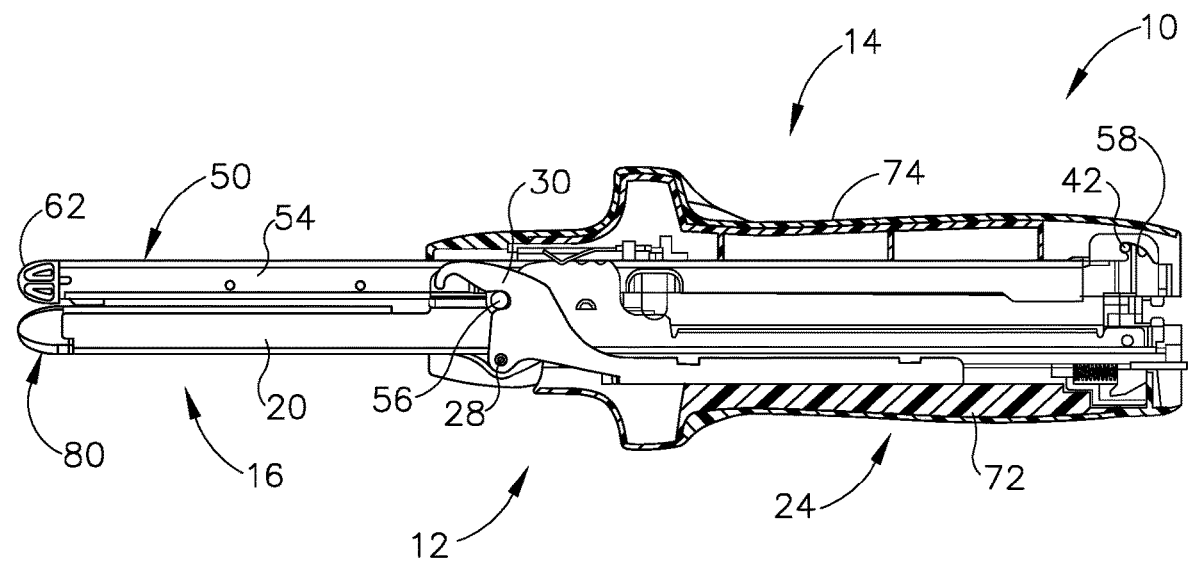
FIG. 4C depicts a cross-sectional side view of the linear surgical stapler of FIG. 1, showing the stapler halves coupled together with the clamp lever in a fully closed position.

FIGS. 4A-4C show exemplary coupling of stapler halves (12, 14) during a surgical procedure. As shown in FIG. 4A, the proximal end of anvil half (14) is aligned with the proximal end of cartridge half (12) such that proximal pivot pin (42) of cartridge half (12) is received by proximal hooks (58) of anvil half (14). With clamp lever (24) in the open position, anvil half (14) is then pivoted toward cartridge half (12), about proximal pivot pin (42), to direct latch projections of anvil half (14) into slots (32) of clamp lever jaws (30). Once latch projections (56) are received by clamp lever jaws (30), clamp lever (24) is pivoted toward the partially closed position shown in FIG. 4B. In this partially closed position of clamp lever (24), anvil half (14) is partially clamped with cartridge half (12) such that stapler (10) may now be held with a single hand without halves (12, 14) undesirably separating from one another. Additionally, in this state, the distal portions of stapler halves (12, 14) remain spaced apart from one another to permit positioning of tissue between the distal portions. It will be appreciated that tissue may be positioned between the distal portions of stapler halves (12, 14) before or upon achieving this partially clamped state.

As shown in FIG. 4C, clamp lever (24) is then pivoted further toward its fully closed position such that the camming surfaces of clamp lever jaws (30) draw latch projections of anvil half (14) proximally against the closed proximal ends of slots (32) of clamp lever jaws (30), thereby fully clamping stapler halves (12, 14) together with tissue positioned securely therebetween. Once halves (12, 14) of stapler (10) are in a fully clamped state, actuator (38) may be manipulated to fire staple cartridge (80). In particular, as shown in FIGS. 5A and 5B, actuator (38) is pivoted about the proximal end of stapler (10) to overlie one of the lateral sides of stapler (10). Actuator (38) is then driven distally to actuate firing assembly (34) in the manner described above and thereby simultaneously sever and staple the clamped tissue. Upon completing a distal firing stroke, actuator (38) may be returned to its proximal home position shown in FIG. 2, and clamp lever (24) may then be opened to separate stapler halves (12, 14) from one another and release the stapled and severed tissue.

II. Exemplary Linear Surgical Stapler Having Proximal Retaining Assembly

As described above in connection with FIGS. 4A-4C, clamp lever (24) must be actuated from its fully open position to at least a partially closed position in which lever jaws (30) initially capture latch projections (56) of anvil half (14) in order to prevent separation of anvil half (14) from cartridge half (12). However, this initial coupling process requires the use of both hands of an operator, thus preventing the operator from being able to mount tissue to stapler (10) when clamp lever (24) is fully opened. Because it is generally easier to mount tissue to stapler halves (12, 14) while clamp lever (24) is fully opened, thus allowing the distal portions of stapler halves (12, 14) to be spaced further apart from one another, the operator will often enlist the help of an assistant in a "4-hands" assembly approach.

In many instances, it may be desirable for an operator to be able to mount tissue to the separate halves of a linear surgical stapler with the clamp lever in a fully open position and without the aid of an assistant, such that the operator may use a first hand to hold the stapler and a second hand to position tissue relative to the stapler. The exemplary stapler (200) described below includes features that enable proximal ends of the first and second stapler halves to remain coupled together while the clamp lever is in a fully open position. This configuration enables the operator to suitably manipulate stapler (200) with a first hand, while leaving the other hand free to manipulate tissue relative to stapler (200).

A. Overview of Linear Surgical Stapler

Figure 7:
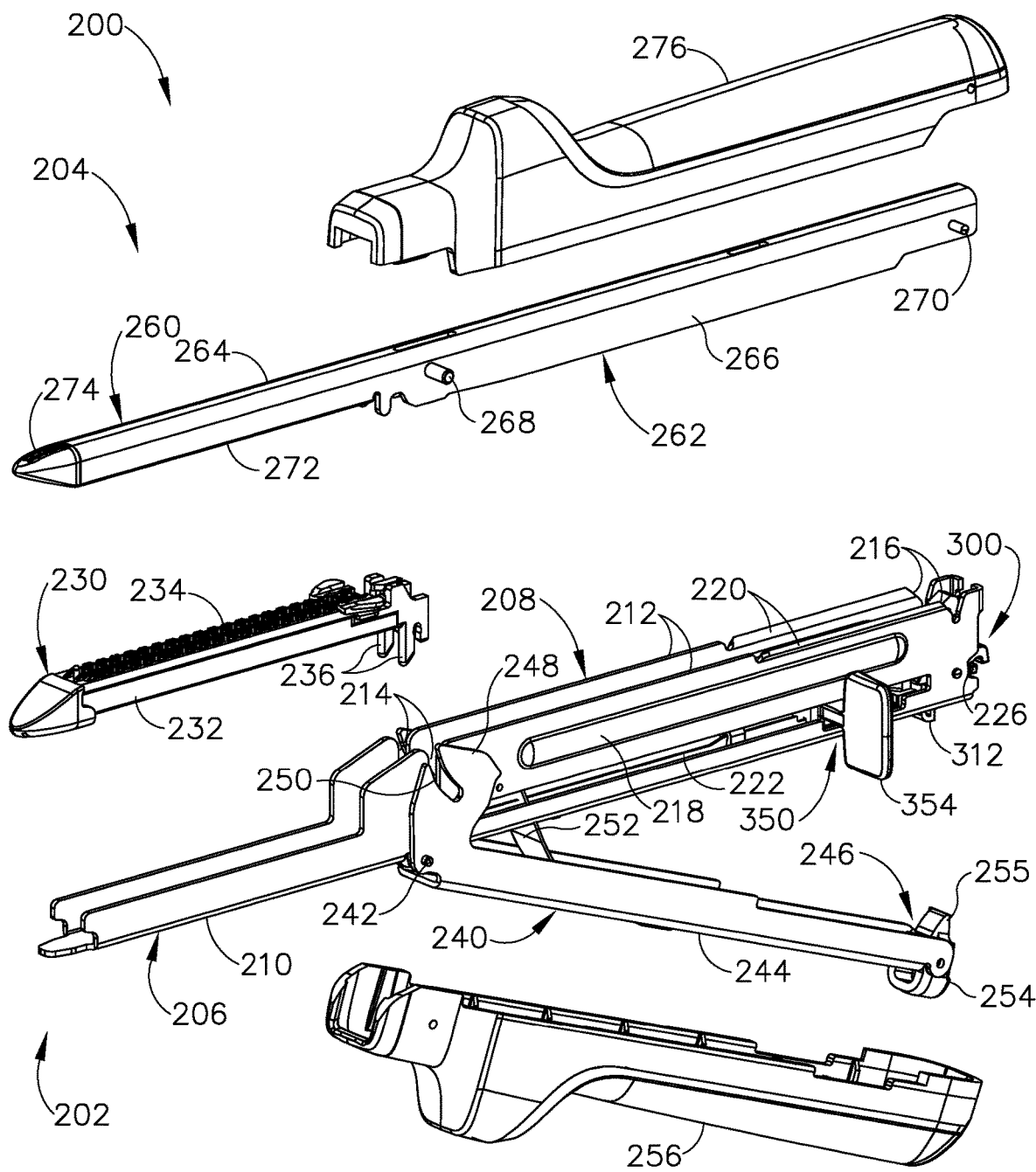
FIG. 7 depicts an exploded perspective view of the linear surgical stapler of FIG. 6.

FIGS. 6 and 7 show another exemplary linear surgical stapler (200) (or "linear cutter") that is generally similar to linear surgical stapler (10) described above except as otherwise described below. Linear surgical stapler (200) includes a cartridge half (202) (or "reload half") and an anvil half (204) configured to releasably couple together to clamp tissue therebetween for simultaneous cutting and stapling of the clamped tissue.

Cartridge half (202) includes an elongate cartridge channel (206) having a proximal frame portion (208) and a distal jaw portion (210). Proximal frame portion (208) slidably retains a firing assembly (350) and includes a laterally opposed pair of upright side flanges (212). Each side flange (212) includes a vertical slot (214) arranged at a distal end thereof, and a tapered notch (216) arranged at a proximal end thereof. An outwardly projecting stiffening rib (218) extends longitudinally between distal slot (214) and the proximal notch (216) of each side flange (212) and is configured to provide the side flange (212) with enhanced stiffness. An outwardly flared upper segment (220) defines an upper edge of a proximal portion of each side flange (212) and is configured to facilitate receipt of anvil half (204) by cartridge half (202), as described in greater detail below. Each side flange (212) further includes an elongate firing slot (222) extending longitudinally between proximal notch (216) and distal slot (214) along a lower side of side flange (212). Elongate firing slots (222) are configured to guide firing assembly (350) between proximal and distal positions. Firing assembly (350) is described in greater detail below in connection with FIGS. 16-21.

Distal jaw portion (210) of cartridge channel (206) is configured to receive a staple cartridge (230) (or "reload"), which may be similar to staple cartridge (80) described above except as otherwise described below. Staple cartridge (230) includes a cartridge body (232) that houses a plurality of staple drivers and staples (not shown) similar to staple drivers (86) and staples (88). Cartridge body (232) further includes a longitudinal slot (234) configured to slidably receive a knife member (366) (see FIG. 16) of firing assembly (350), and a pair of interior slots (not shown) configured to slidably receive a pair of cam ramps (360) (see FIG. 16) of firing assembly (350). In other versions, staple cartridge (230) and firing assembly (350) may be alternatively configured such that knife member (366) and cam ramps (360) are housed within cartridge body (232), similar to staple cartridge (80). Staple cartridge (230) of the present version further includes a pair of proximal coupling legs (236) configured to be directed through an opening (not shown) in a lower wall of cartridge channel (206) and releasably couple to a clamp lever pivot pin (242) with a snap-fit engagement.

Cartridge half (202) further includes a clamp lever (240) pivotably coupled to cartridge channel (206) with clamp lever pivot pin (242), which is arranged in approximate alignment with distal slots (214) of cartridge channel side flanges (212). Clamp lever (240) includes an elongate lever arm (244) having a free proximal end (246) and a distal end that is pivotably coupled to a lower portion of cartridge channel (206) with pivot pin (242). A pair of opposed jaws (248) extend distally from the distal end of lever arm (244) alongside cartridge channel side flanges (212). Each jaw (248) includes a curved slot (250) having a closed proximal end and an open distal end configured to receive a latch projection of anvil half (204), as described below.

Clamp lever (240) is operable to pivot relative to cartridge channel (206) between an open position in which proximal end (246) of lever arm (244) is spaced from cartridge channel frame portion (208), and a closed position in which proximal end (246) confronts cartridge channel frame portion (208). Actuation of clamp lever (240) from the open position to the closed position operates to clamp anvil half (204) against cartridge half (202). In particular, the curvature of each jaw slot (250) defines respective upper and lower camming surfaces configured to engage and draw the respective latch projection of anvil half (204) toward cartridge channel (206) as clamp lever (240) is pivotably closed, as described below.

Cartridge half (202) of the present example further includes a resilient member shown in the form of a flat spring (252) that biases lever arm (244) toward the open position. Accordingly, flat spring (252) promotes disengagement of lever jaws (248) from anvil half (204) upon initial advancement of clamp lever (240) from the closed position toward the open position. Cartridge half (202) further includes a clamp lever latch member (254) arranged at proximal end (246) of lever arm (244). As described in greater detail below, clamp lever latch member (254) is resiliently biased to engage a proximal end of cartridge channel (206) and thereby releasably retain clamp lever (240) in the closed position, for instance while stapler (200) is being fired.

Anvil half (204) of linear surgical stapler (200) includes an elongate anvil channel (260) having a proximal frame portion (262) and a distal jaw portion (264). Proximal frame portion (262) includes a laterally opposed pair of upright side flanges (266) that are configured to be received between cartridge channel side flanges (212) when anvil half (204) is coupled with cartridge half (202). A distal latch projection in the form of a distal pin (268) extends laterally through the distal ends of anvil channel side flanges (266), and a proximal pivot projection in the form of a proximal pin (270) extends laterally through the proximal ends of anvil channel side flanges (266). Anvil pins (268, 270) are configured to facilitate coupling of anvil half (204) with cartridge half (202) as described below.

Distal jaw portion (264) of anvil half (204) supports an anvil surface (272) having a plurality of staple forming pockets (not shown) configured to deform the legs of staples ejected by staple cartridge (230) when stapler (200) is fired. In some versions, anvil surface (272) may be formed integrally with or otherwise be rigidly connected to distal jaw portion (264), for example as described below in connection with FIGS. 37A-39. In other versions, anvil surface (272) may be adjustable relative to distal jaw portion (264) in a manner similar to anvil plate (60) of stapler (10) described above. Distal jaw portion (264) of anvil half (204) additionally supports a tapered distal tip member (274).

Similar to linear surgical stapler (10), linear surgical stapler (200) includes a plurality of shrouds (256, 276) that cover select portions of stapler (200) and promote effective grip and manipulation of stapler (200) by an operator during use. In particular, a clamp lever shroud (256) is affixed to and covers an outwardly facing side of clamp lever (240) such that clamp lever shroud (256) is configured to pivot with clamp lever (240) relative to cartridge channel (206). Additionally, an anvil shroud (276) is affixed to and covers an outwardly facing side of anvil channel (260). In some versions, anvil shroud (276) may be coupled with anvil channel (260) in accordance with the teachings of U.S. patent application Ser. No. 16/102,170, entitled "Clamping Assembly for Linear Surgical Stapler," filed on Aug. 13, 2018, published as U.S. Pub. No. 2020/0046353 on Feb. 13, 2020, the disclosure of which is incorporated by reference herein. It will be appreciated that in other versions, shrouds (256, 276) may be coupled with clamp lever (240) and anvil channel (260) in a variety of other manners readily apparent to those of ordinary skill in the art.

During assembly of stapler halves (202, 204), proximal pin (270) of anvil half (204) is directed into proximal tapered notches (216) of cartridge channel (206). Meanwhile, clamp lever (240) is held in the open position by resilient member (252) such that the open distal ends of curved jaw slots (250) align with the open upper ends of cartridge channel distal slots (214). Anvil half (204) is then pivoted about proximal pin (270) to direct distal pin (268) of anvil half (204) into vertical distal slots (214) of cartridge channel (206) and curved jaw slots (250) of clamp lever (240). Clamp lever (240) is then pivoted from the open position to the closed position, which causes the upper and lower camming surfaces of curved jaw slots (250) to engage and draw distal pin (268) toward the closed proximal ends of curved jaw slots (250). This action draws distal jaw portion (264) of anvil channel (260) closer toward distal jaw portion (210) of cartridge channel (206), thereby clamping any tissue positioned between anvil surface (272) and staple cartridge (230). When clamp lever (240) reaches the fully closed position, clamp lever latch member (254) engages the proximal end of cartridge channel (206) to maintain clamp lever (240) in the closed position. Stapler (200) may then be fired by actuating firing assembly (350) distally similar to firing assembly (34). After firing, firing assembly (350) is returned to its proximal home position, and clamp lever latch member (254) is disengaged from cartridge channel (206) to enable opening of clamp lever (240) and subsequent separation of stapler halves (202, 204).

B. Proximal Retaining Assembly of Linear Surgical Stapler

FIGS. 8-11 show details of an exemplary retaining assembly (300) arranged at a proximal end of linear surgical stapler (200) and which is configured to releasably retain portions of anvil half (204) and firing assembly (350) as described below. Retaining assembly (300) of the present example includes an anvil latch member (302) and a detent member (304), both of which are rotatably coupled with a proximal end of cartridge channel (206) via a laterally extending pin (306) arranged proximally of firing slots (222).

Figure 10:
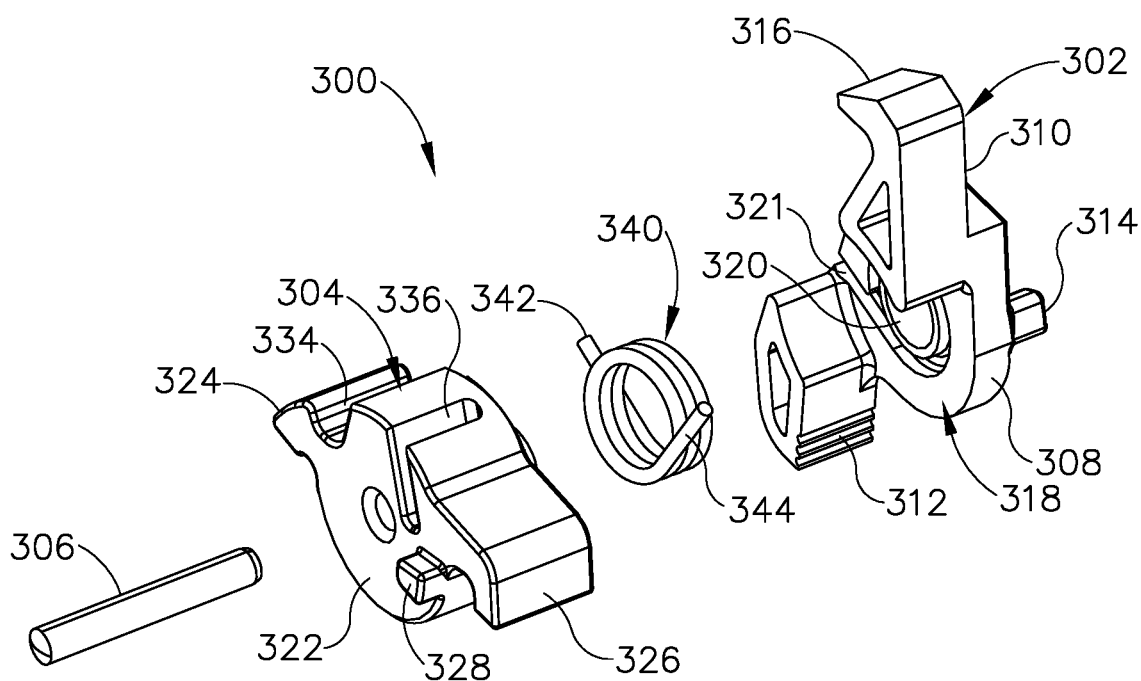
FIG. 10 depicts an exploded left perspective view of the proximal retaining assembly of FIG. 9.
Figure 11:
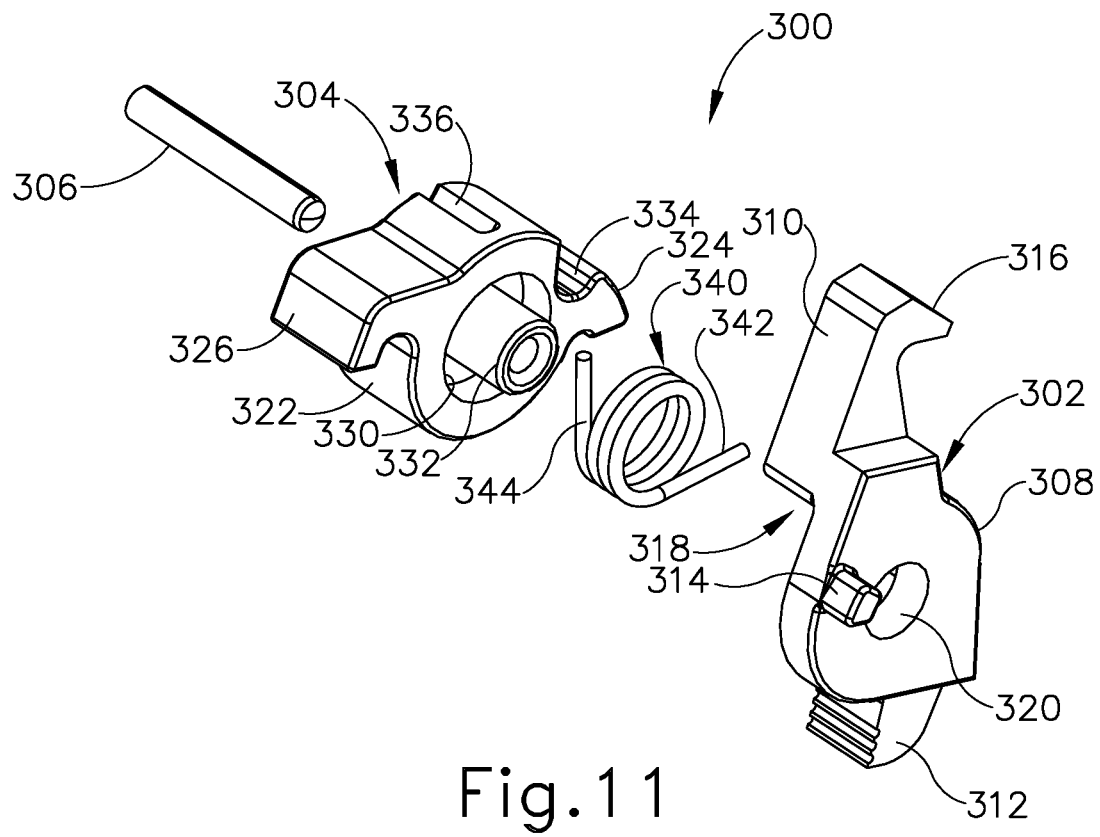
FIG. 11 depicts an exploded right perspective view of the proximal retaining assembly of FIG. 9.

As shown best in FIGS. 10 and 11, anvil latch member (302) includes a central body (308), a latch finger (310) extending upwardly from an upper side of central body (308), a release button (312) extending downwardly from a lower side central body (308), and a stop tab (314) arranged on an outwardly facing lateral side of central body (308) opposed from detent member (304). An upper end of latch finger (310) tapers distally and defines an upper cam ramp (316) configured to engage proximal pin (270) of anvil half (204) in the manner described below. Anvil latch member (302) further includes a central cutout feature (318) shaped to receive a portion of detent member (304) as described below, and an opening (320) extending laterally through central body (308).

Detent member (304) includes a generally cylindrical central body (322), a distal finger (324) extending distally from a distal side of central body (322), a hook element (326) extending proximally from a proximal side of central body (322), and a stop tab (328) arranged on an outwardly facing lateral side of central body (322) opposed from anvil latch member (302). As shown in FIG. 11, a lateral side of detent member (304) that confronts anvil latch member (302) includes an annular recess (330) and a shaft (332) extending laterally from annular recess (330) in a direction toward anvil latch member (302). Distal finger (324) of detent member (304) includes a proximal uppercut feature (334) that defines a proximal cam ramp of distal finger (324), and a sloped distal end that defines a distal cam ramp of distal finger (324). These proximal and distal cam ramps of distal finger (324) are configured to interact with firing assembly (350) as described in greater detail below.

Figure 8:
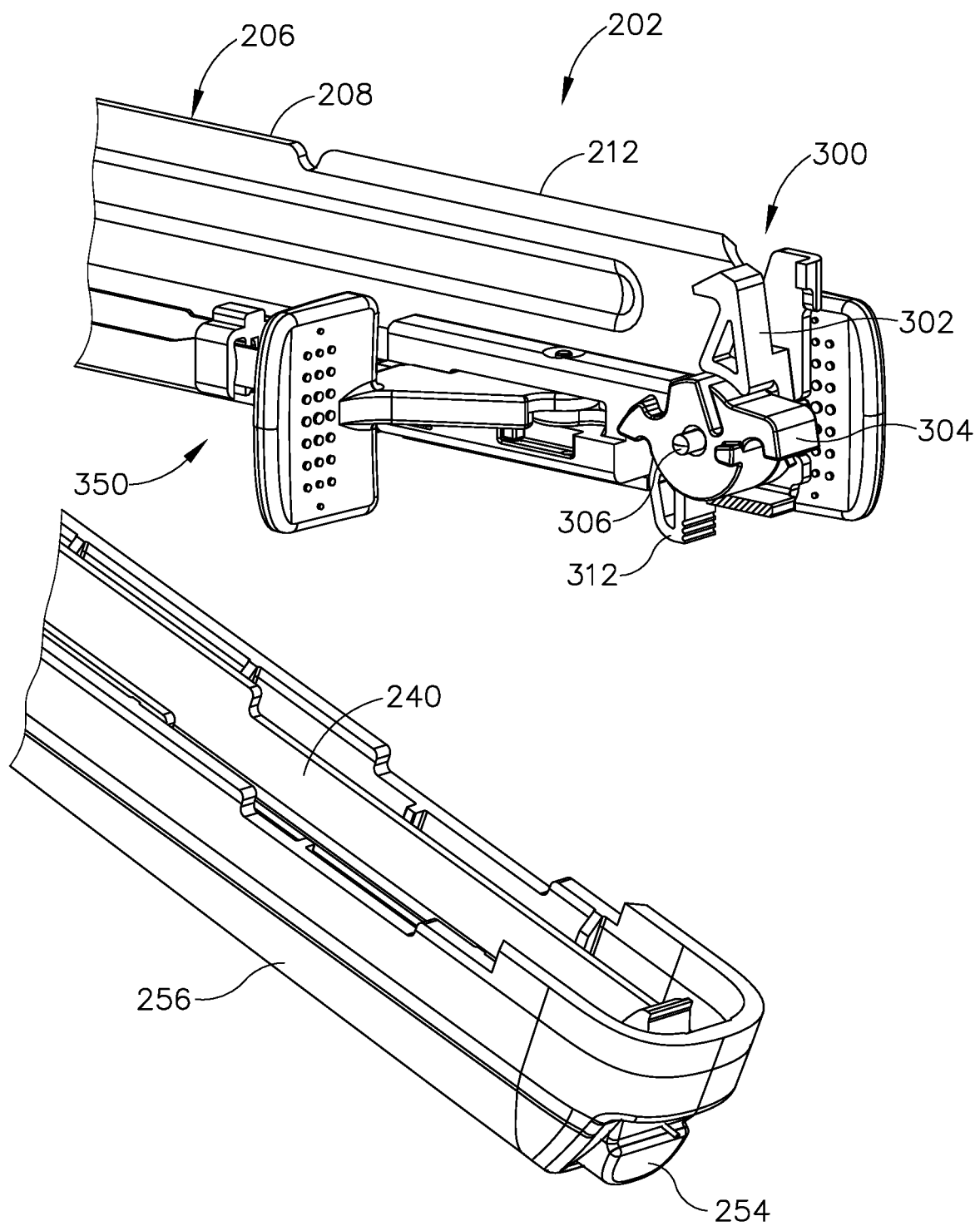
FIG. 8 depicts a perspective view of a proximal portion of the cartridge half of the linear surgical stapler of FIG. 6, showing the clamp lever in an open position and revealing internal features of the cartridge half.
Figure 9:
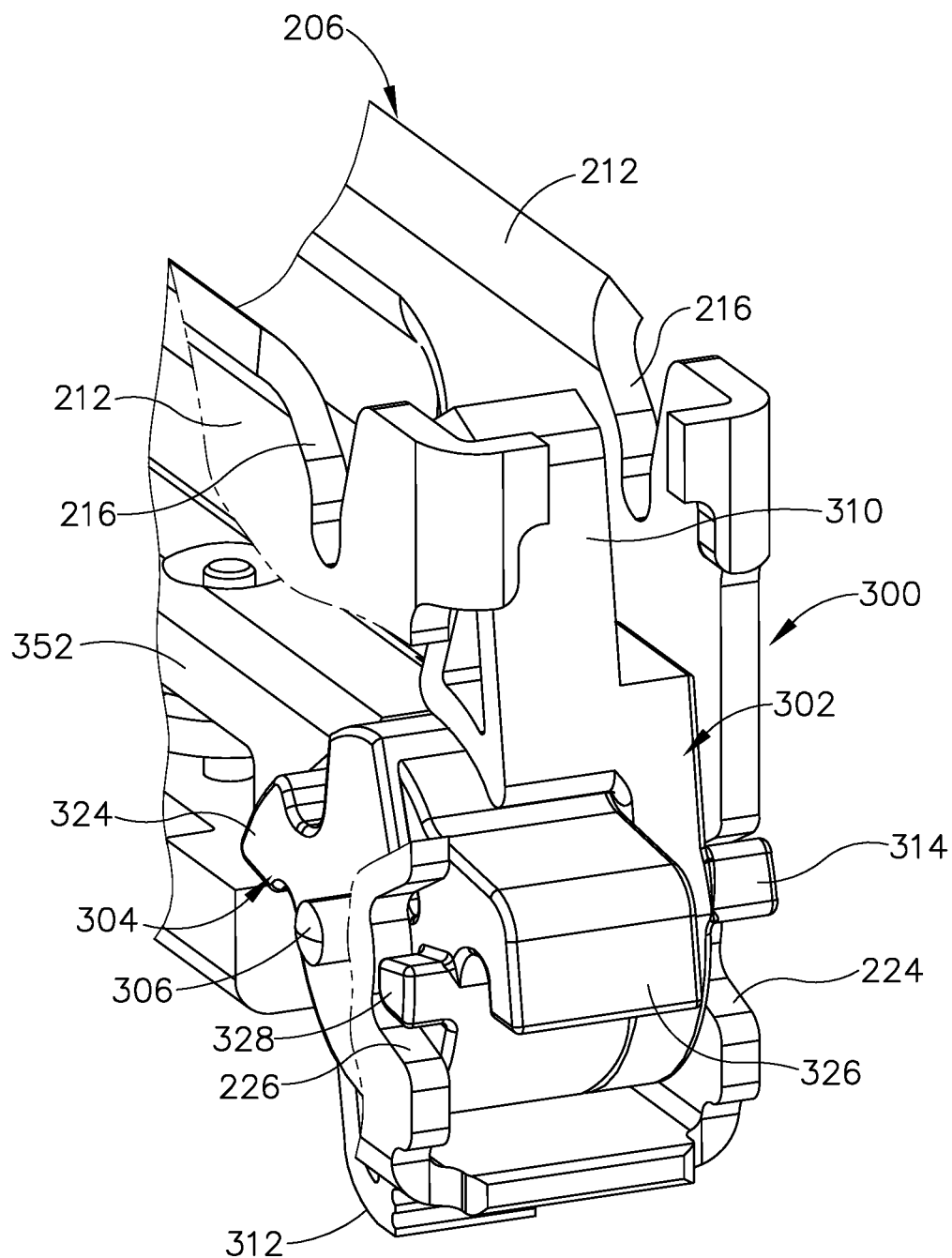
FIG. 9 depicts a perspective view of a proximal end of the cartridge half of FIG. 8, showing a side portion of a cartridge channel of the cartridge half partially cut away to reveal a proximal retaining assembly that includes an anvil latch member and a detent member.

Anvil latch member (302) and detent member (304) are configured to mate together such that their inwardly facing lateral sides confront one another along a plane that extends generally parallel to a longitudinal axis of linear surgical stapler (200). Central body (322) of detent member (304) is received within central cutout feature (318) of anvil latch member (302) such that latch finger (310) and release button (312) of anvil latch member (302) laterally overlie central body (322) of detent member (304). Additionally, lateral shaft (332) of detent member (304) is received through lateral opening (320) of anvil latch member (302), such that anvil latch member (302) may rotate about shaft (332). Pin (306) is then received through a central bore of lateral shaft (332) and is secured at its lateral ends to cartridge channel side flanges (212), as shown in FIGS. 8 and 9. Accordingly, anvil latch member (302) and detent member (304) are arranged coaxially about a lateral axis defined by pin (306)

and shaft (332). As described below, anvil latch member (302) and detent member (304) are configured to rotate independently from and relative to one another about the shared axis.

Retaining assembly (300) further includes a resilient member shown in the form of a torsion spring (340) positioned between anvil latch member (302) and detent member (304). A first lateral side of torsion spring (340) and a corresponding first spring leg (342) is captured within a complementary shaped recess (321) formed in central body (308) of anvil latch member (302). A second lateral side of torsion spring (340) is received within annular recess (330) of detent member (304) such that a corresponding second spring leg (344) is captured within a radially extending slot (336) formed in central body (322) of detent member (304). Torsion spring (340) is configured to resiliently bias anvil latch member (302) and detent member in opposite rotational directions about the lateral axis defined by pin (306). In particular, in the views depicted in FIGS. 9 and 12A-12C, torsion spring (340) is configured to bias anvil latch member (302) in a counter-clockwise direction about pin (306) such that latch finger (310) is biased distally. Additionally, torsion spring (340) is configured to bias detent member (304) in a clockwise direction such that distal finger (324) is biased upwardly and proximal hook element (326) is biased downwardly.

As shown in FIG. 9, stop tab (314) of anvil latch member (302) is configured to abut the upper surface of an adjacent first stop notch (224) formed in the distal end of a corresponding first side flange (212) of cartridge channel (206). Additionally, stop tab (328) of detent member (304) is configured to abut the lower surface of an adjacent second stop notch (226) formed in the distal end of a corresponding second side flange (212) of cartridge channel (206). Anvil latch member stop tab (314) and its respective channel stop notch (224) are configured to interact such that anvil latch member (302) is biased toward a rotational orientation in which latch finger (310) extends generally vertically. Additionally, detent member stop tab (328) and its respective channel stop notch (226) are configured to interact such that detent member (304) is biased toward a rotational orientation in which distal finger (324) and proximal hook element (326) extend generally horizontally.

Figure 12A:
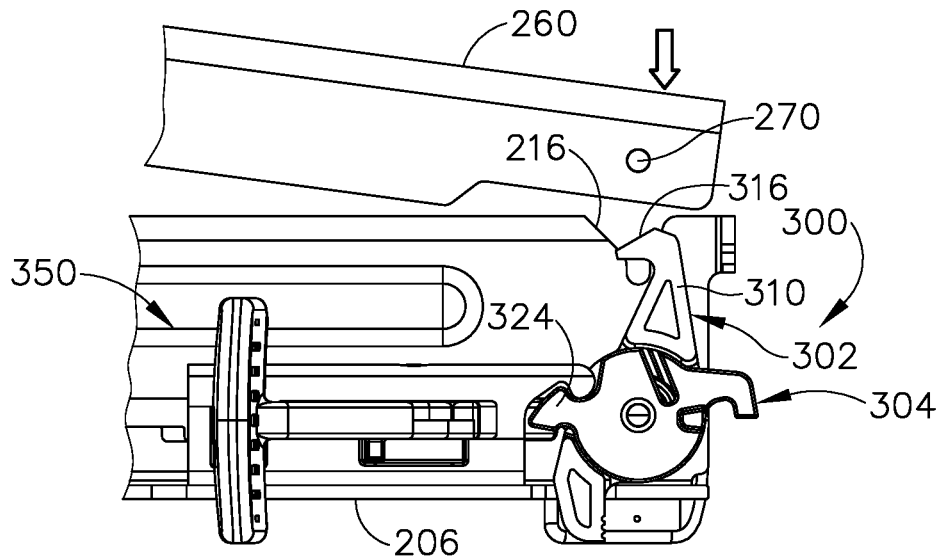
FIG. 12A depicts a side elevational view of the linear surgical stapler of FIG. 6 with an anvil shroud omitted and a side portion of the cartridge channel cut away, showing the anvil latch member in a first rotational position as a proximal end of the anvil half is aligned with a proximal end of the cartridge half.
Figure 12B:
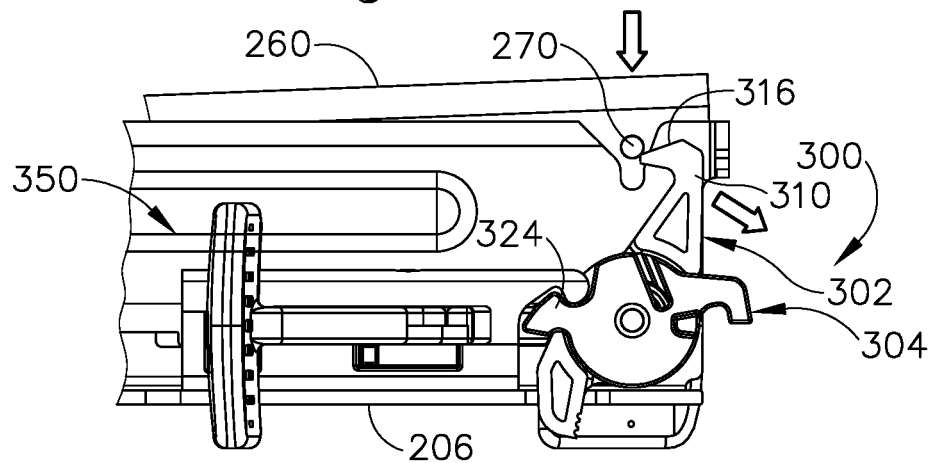
FIG. 12B depicts a side elevational view of the linear surgical stapler of FIG. 6 with the anvil shroud omitted and a side portion of the cartridge channel cut away, showing the anvil latch member in a second rotational position as a proximal pin of the anvil half engages an upper surface of the anvil latch member.
Figure 12C:
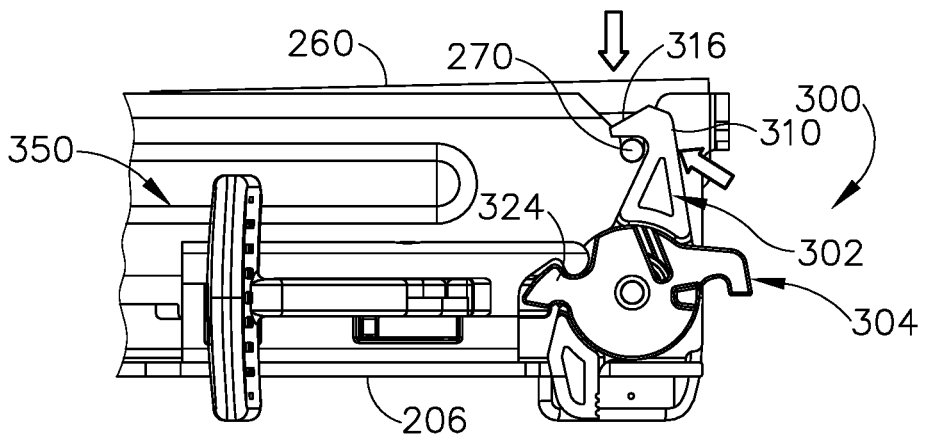
FIG. 12C depicts a side elevational view of the linear surgical stapler of FIG. 6 with the anvil shroud omitted and a side portion of the cartridge channel cut away, showing the anvil latch member after having returned to the first rotational position to releasably capture the proximal anvil pin and thereby couple the proximal ends of the stapler halves together.

FIGS. 12A-12C show engagement of anvil latch member (302) with proximal pin (270) of anvil half (204) to provide for releasable coupling of the proximal end of anvil half (204) with the proximal end of cartridge half (202). FIG. 12A shows cartridge half (202) and anvil half (204) in a pre-assembled state in which anvil half (204) is separated from cartridge half (202), clamp lever (240) (not depicted) is in a fully open position, and firing assembly (350) is held in a proximal home position by distal finger (324) of detent member (304), as described in greater detail below. As shown in FIGS. 12A and 12B, the proximal end of anvil half (204) is aligned with and brought toward the proximal end of cartridge half (202) such that proximal pin (270) is directed into proximal tapered notches (216) of cartridge channel (206) and contacts upper cam ramp (316) of anvil latch member (302). This engagement forces anvil latch member (302) to rotate clockwise such that latch finger (310) moves proximally, which allows proximal pin (270) to slip over the tapered distal tip of latch finger (310). As shown in FIG. 12C, anvil latch member (302) then snaps back counter-clockwise such that latch finger (310) hooks over and captures proximal pin (270), thereby coupling the proximal end of anvil half (204) with the proximal end of cartridge half (202). Because anvil latch member (302) is rotatable independently of detent member (304), detent member (304) remains rotationally stationary throughout the coupling steps shown in FIGS. 12A-12C.

Figure 13A:
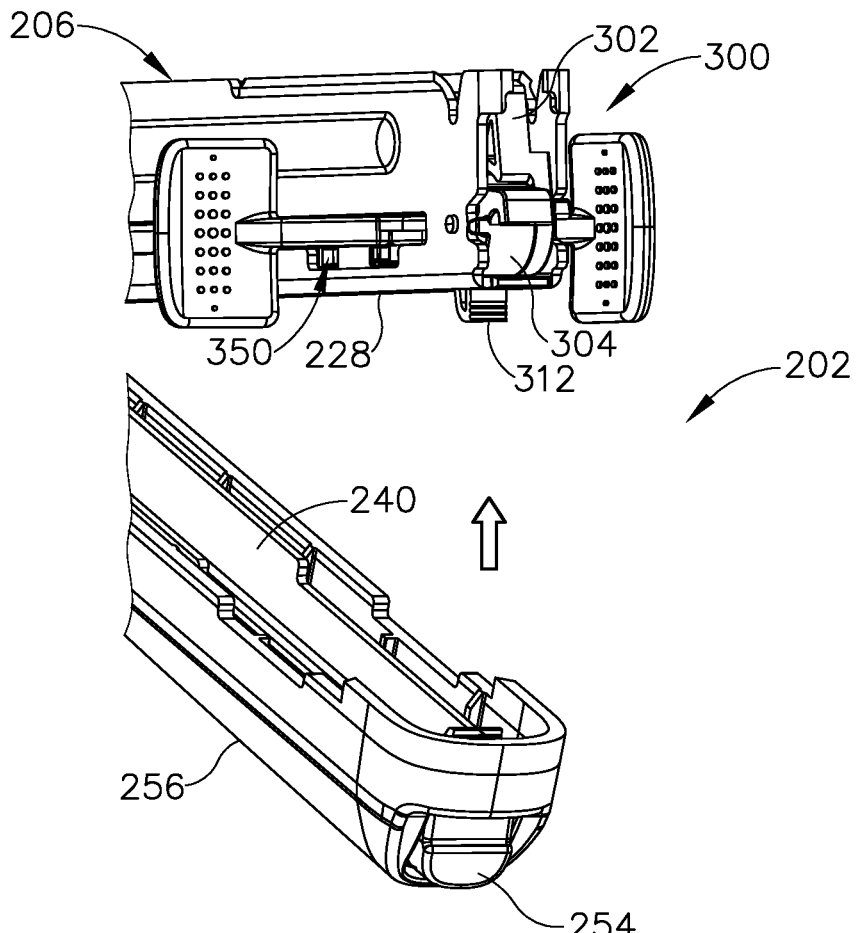
FIG. 13A depicts a perspective view of a proximal portion of the cartridge half of the linear surgical stapler of FIG. 6, showing the clamp lever in an open position.
Figure 13B:
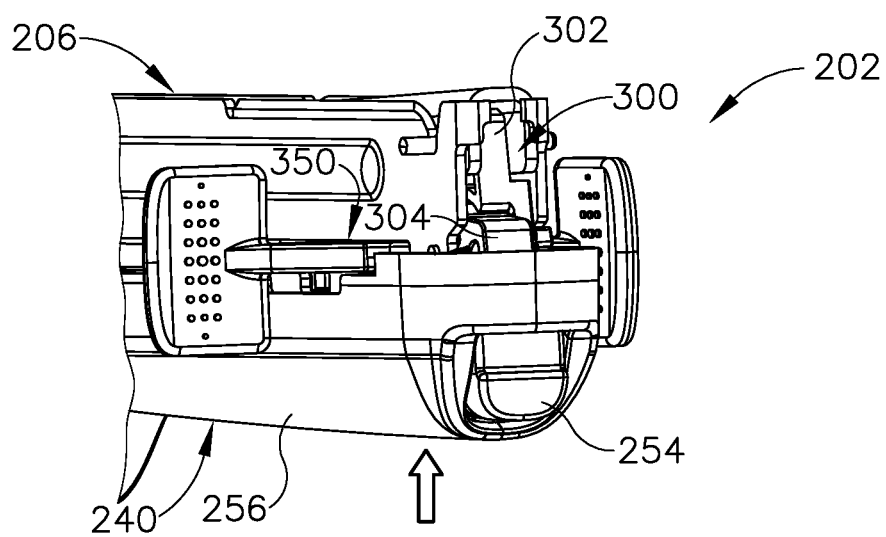
FIG. 13B depicts a perspective view of a proximal portion of the cartridge half of FIG. 13A, showing the clamp lever in a closed position in which a latch of the clamp lever engages a proximal end of the cartridge channel.
Figure 14A:
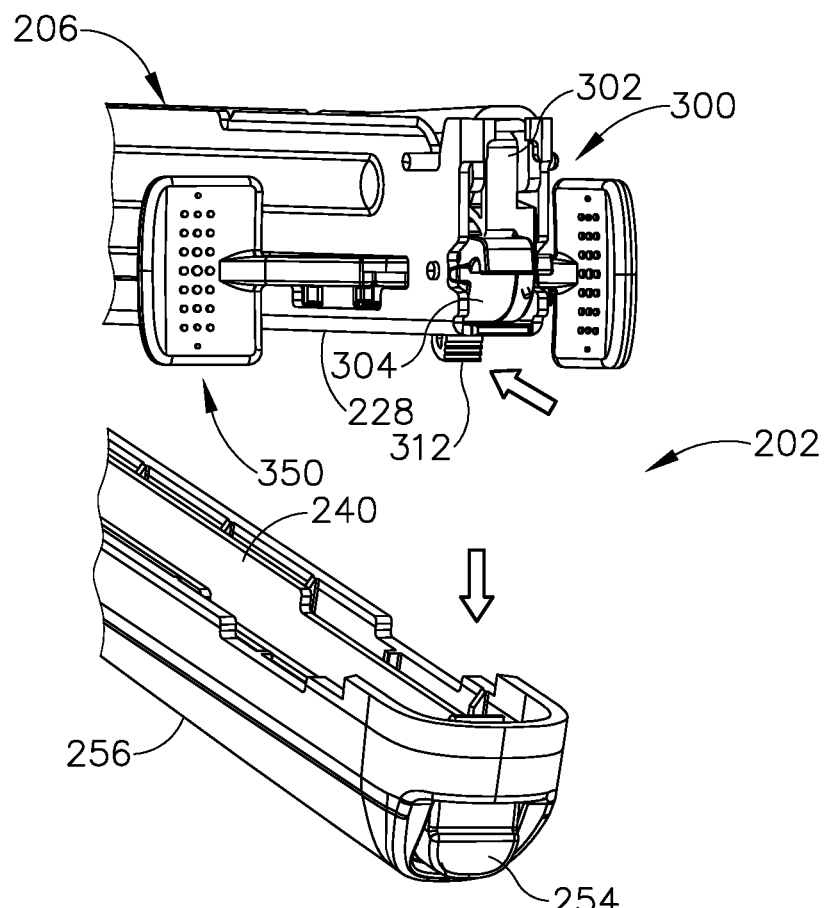
FIG. 14A depicts a perspective view of a proximal portion of the cartridge half of the linear surgical stapler of FIG. 6, showing the clamp lever in the open position in which a release feature of the anvil latch member is exposed through an underside of the cartridge channel.
Figure 14B:
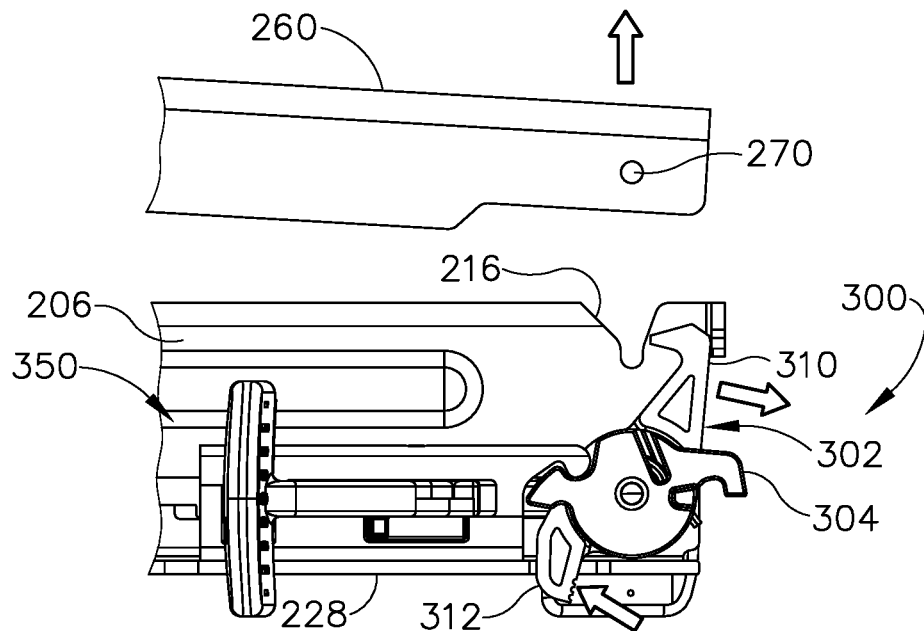
FIG. 14B depicts a side elevational view of proximal portions of the stapler halves of FIG. 6 with the anvil shroud omitted and a side portion of the cartridge channel cut away, showing actuation of the release feature to release the proximal anvil pin from the anvil latch member and thereby permit separation of the stapler halves.

As shown in FIGS. 13A and 13B, release button (312) of anvil latch member (302) is exposed and accessible to an operator only when clamp lever (240) is in the open position. As shown in FIG. 13A, release button (312) extends through an opening formed in a bottom wall (228) of cartridge channel (206). As shown in FIG. 13B, clamp lever (240) in the closed position conceals and blocks access to release button (312), thereby preventing unintentional actuation of release button (312) and resulting separation of the proximal ends of stapler halves (202, 204) during or immediately before a firing stroke. As shown in FIGS. 14A and 14B, separation of the proximal ends of stapler halves (202, 204) is achieved by opening clamp lever (240) and actuating release button (312) distally. As shown in FIG. 14B, this causes anvil latch member (302) to rotate clockwise, thereby driving latch finger (310) proximally to release proximal pin (270) of anvil half (204) so anvil half (204) may be pulled away from cartridge half (202).

Figure 18:
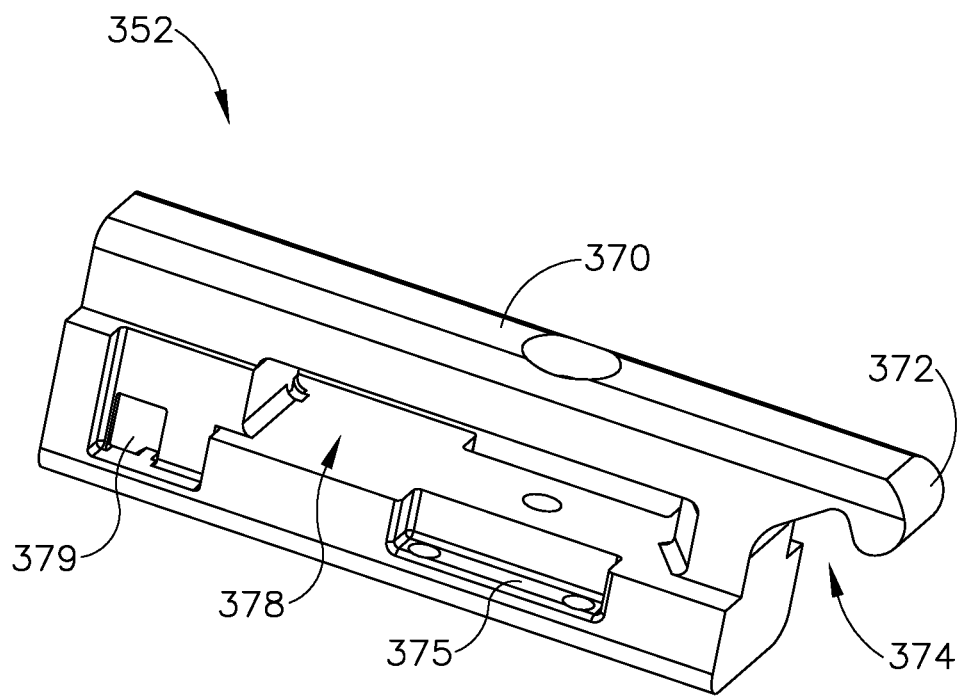
FIG. 18 depicts a top perspective view of the slider block of the firing assembly of FIG. 16.

As shown in FIGS. 15A-15E, a slider block (352) of firing assembly (350) is configured to releasably engage detent member (304) of retaining assembly (300) to provide an operator with a tactile indication of when firing assembly (350) is in a proximal home assembly, as described below. Referring briefly to FIG. 18, slider block (352) includes a block body (370) that is slidably housed between side flanges (212) of cartridge channel (206), and a finger (372) extending proximally from a proximal end of block body (370). Block finger (372) has a rounded proximal end that defines a proximal cam ramp of block finger (372), and an undercut feature (374) that defines a distal cam ramp of block finger (372).

Figure 15A:
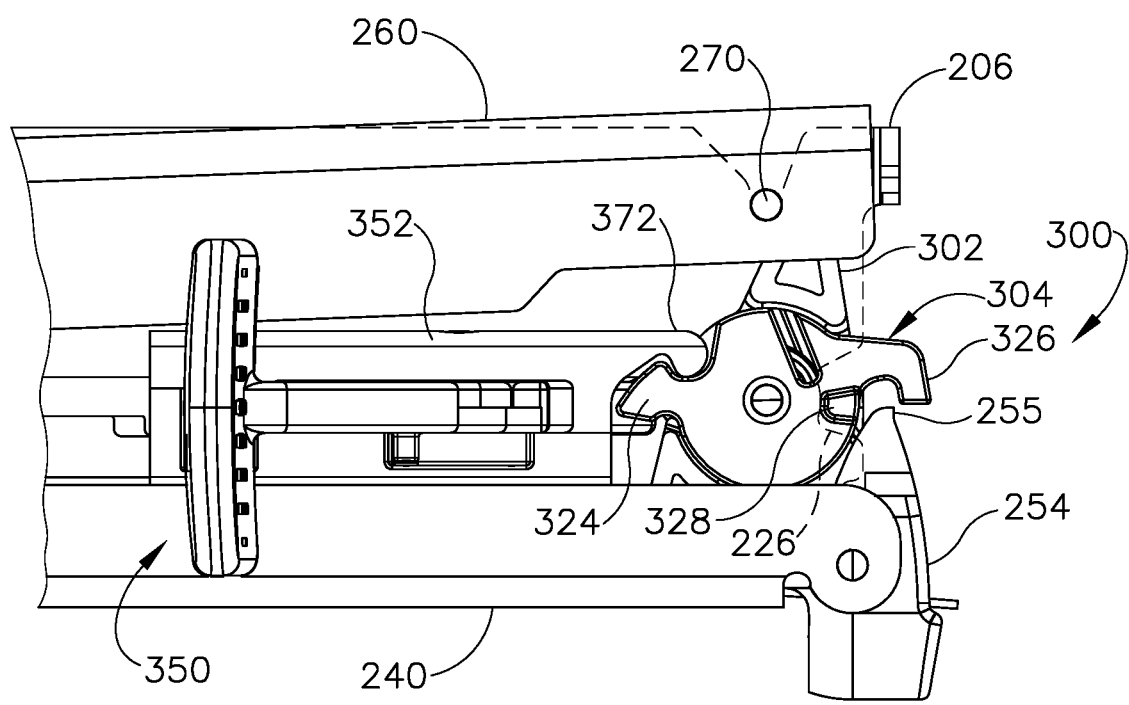
FIG. 15A depicts a side elevational view of a proximal portion of the linear surgical stapler of FIG. 6 with shrouds omitted and a proximal side portion of the cartridge channel outlined in phantom, showing a firing assembly of the linear surgical stapler in a proximal home position prior to firing.

FIG. 15A shows firing assembly (350) in a proximal home position in which slider block (352) is arranged proximally within cartridge channel (206). In this proximal position, block finger (372) hooks over and interlocks with detent finger (324) such that the proximal cam ramp of detent finger (324) contacts the distal cam ramp of block finger (372). This interaction between block finger (372) and detent finger (324) urges detent member (304) slightly in a counter-clockwise direction (in the view of FIG. 15A), against the bias of torsion spring (340), such that detent stop tab (328) is slightly spaced from the lower surface of the respective cartridge channel stop notch (226). In response, torsion spring (340) urges detent member (304) in a clockwise direction so that detent finger (324) exerts an upwardly directed force on block finger (372). This exertion of forces provides a detent engagement that releasably retains firing assembly (350), via slider block (352), in the proximal home position.

Figure 15B:
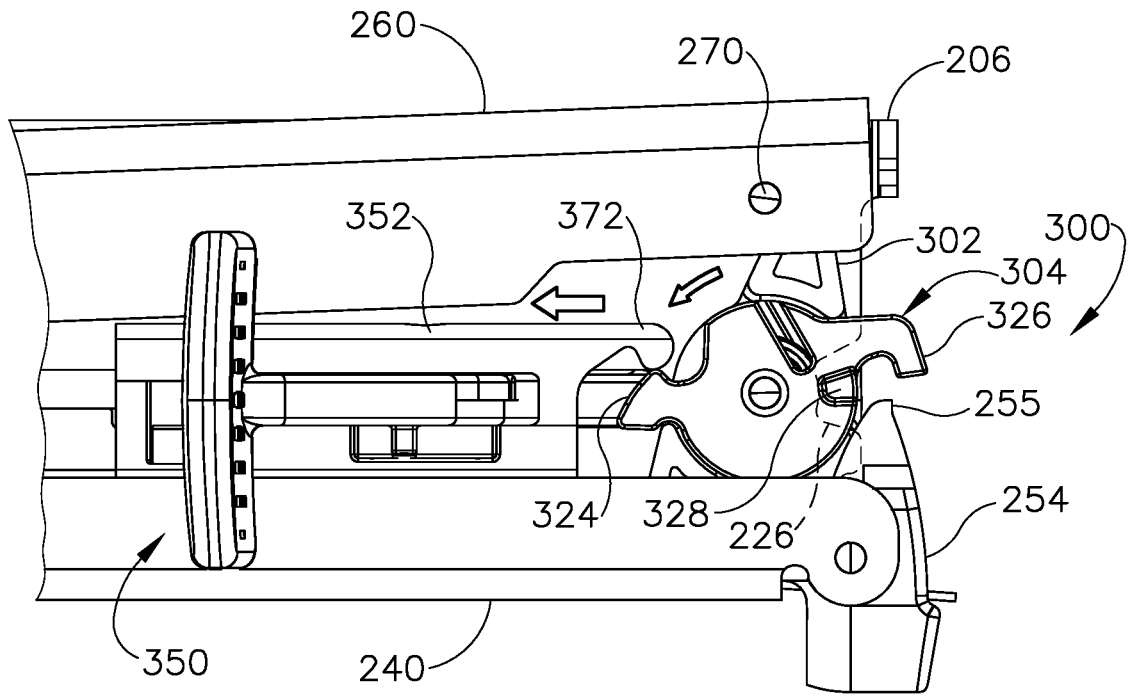
FIG. 15B depicts a side elevational view of the proximal portion of the linear surgical stapler of FIG. 15A, showing the firing assembly advancing distally during firing such that a proximal end of a slider block of the firing assembly rotates the detent member in a first direction.
Figure 15C:
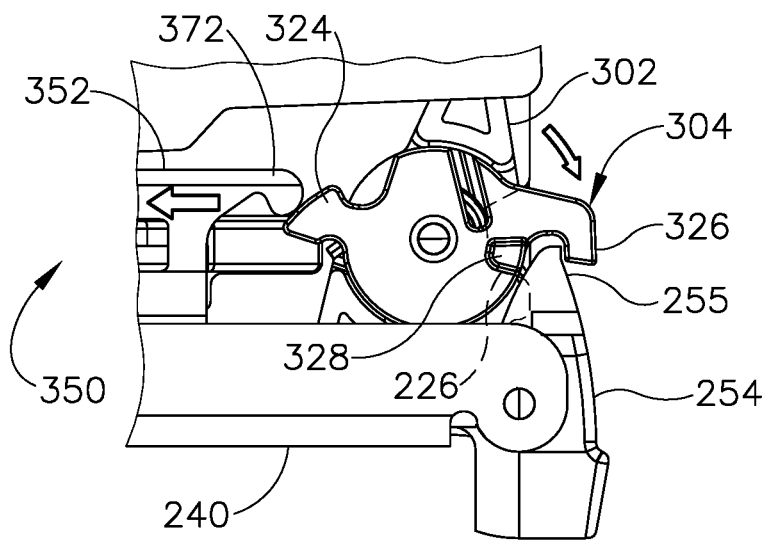
FIG. 15C depicts a side elevational view of the proximal portion of the linear surgical stapler of FIG. 15B, showing the firing assembly advancing further distally during firing such that the slider block disengages the detent member and enables the detent member to rotate in a second direction so that a clamp lever lockout feature of the detent member locks out the clamp lever latch.

As shown in FIG. 15B, when firing assembly (350) is actuated distally by an operator performing a firing stroke, block finger (372) drives detent finger (324) downwardly such that detent member (304) rotates in a counter-clockwise direction. As shown in FIG. 15C, as firing assembly (350) advances further distally, block finger (372) disengages detent finger (324) and the bias of torsion spring (340) rotates detent member (304) in a clockwise direction so that detent stop tab (328) abuts the lower surface of the respective cartridge channel stop notch (226). When detent member (304) assumes this rotational position, proximal hook element (326) of detent member (304) hooks over an upper tip (255) of clamp lever latch member (254), thereby preventing clamp lever latch member (254) from being actuated to release clamp lever (240) from cartridge channel (206).

Accordingly, hook element (326) functions as a safety lockout feature that prevents clamp lever (240) from being opened unless firing assembly (350) is in the proximal home position. Advantageously, this feature ensures that stapler halves (202, 204) cannot be separated from one another while a knife member (366) (see FIG. 16) of stapler (200) is exposed through an upper deck of staple cartridge (230) during a firing stroke.

Figure 15D:
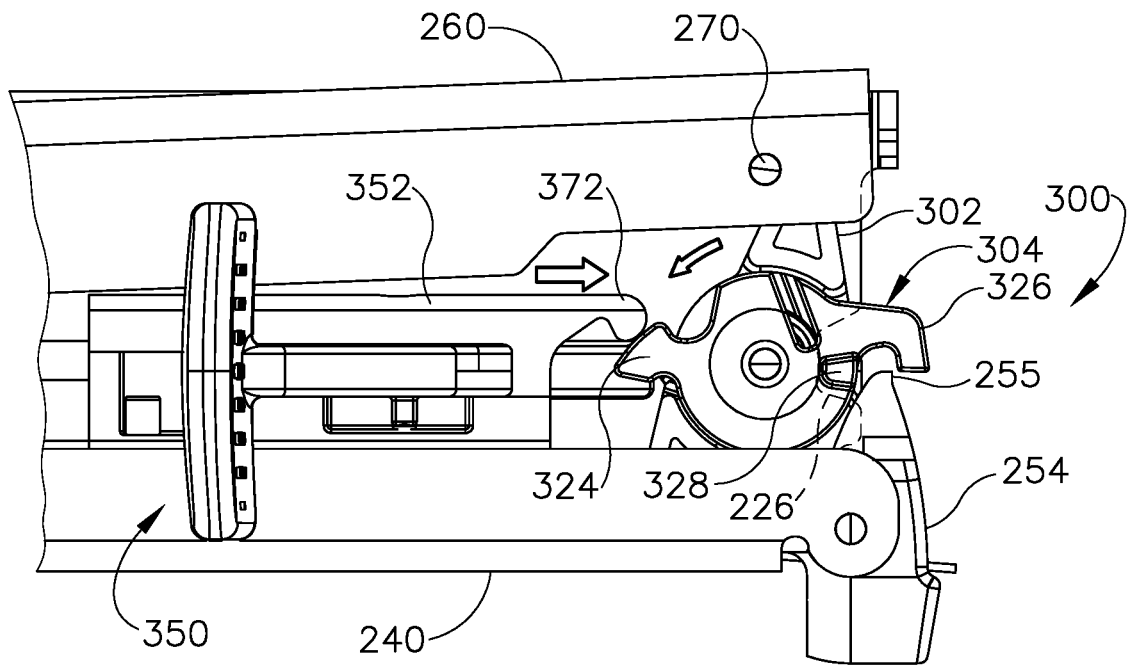
FIG. 15D depicts a side elevational view of the proximal portion of the linear surgical stapler of FIG. 15C, showing the firing assembly advancing proximally after firing such that the slider block reengages and rotates the dent member in the first direction.
Figure 15E:
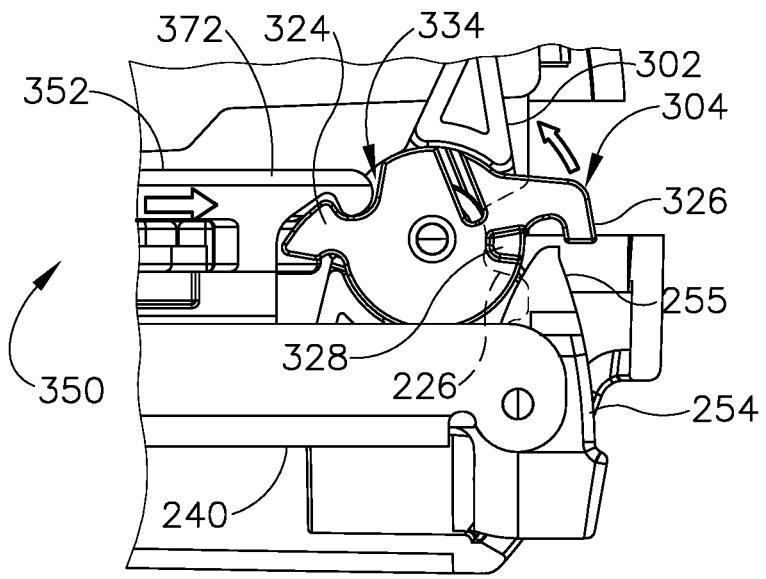
FIG. 15E depicts a side elevational view of the proximal portion of the linear surgical stapler of FIG. 15D, showing the firing assembly returned to the proximal home position in which the detent member is held in a rotational position in which the clamp lever lockout feature is disengaged from the clamp lever latch.
Figure 16:
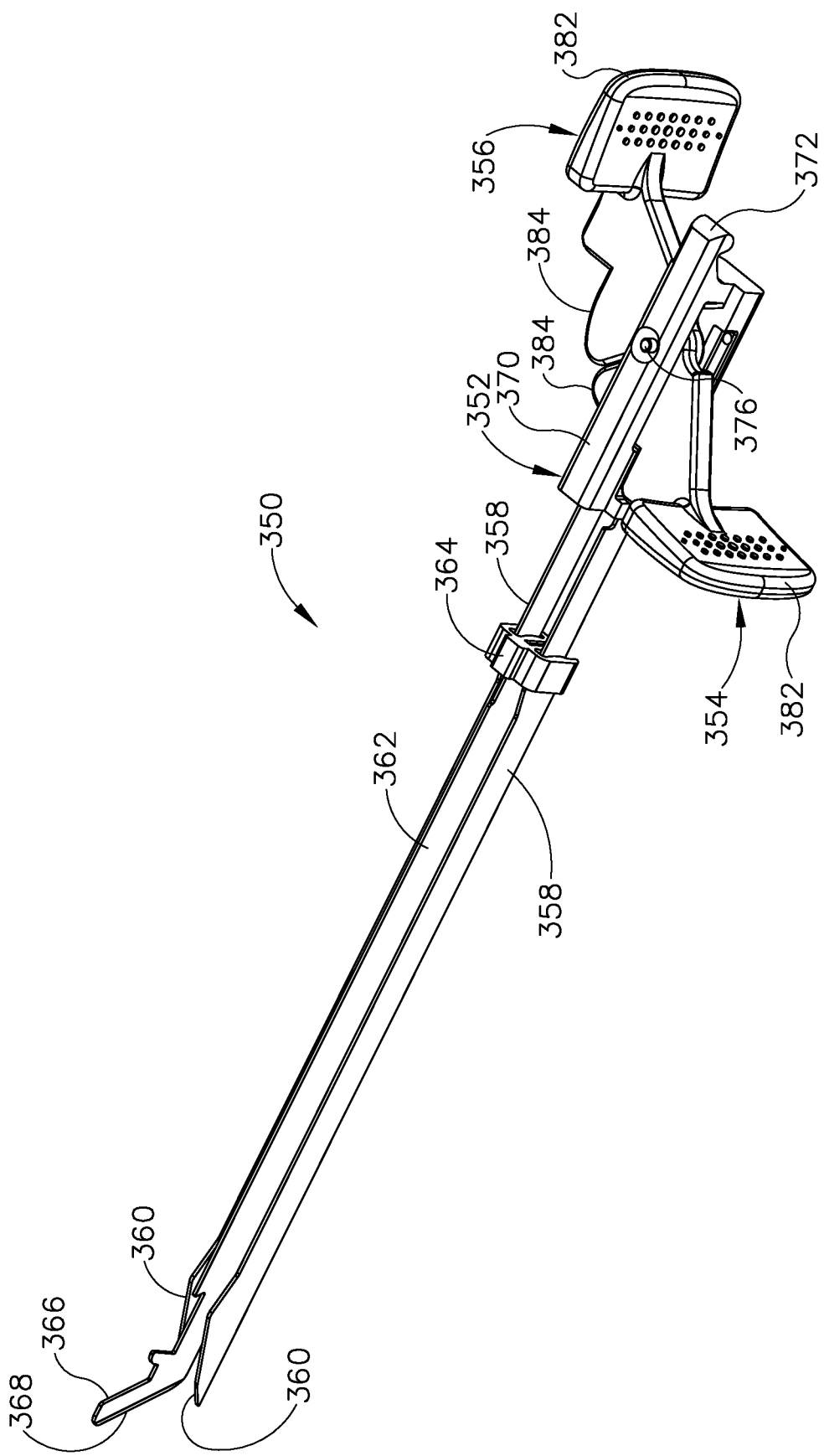
FIG. 16 depicts a top perspective view of the firing assembly of the linear surgical stapler of FIG. 6, which includes a slider block and a pair of rotatable actuators.

As shown in FIGS. 15D and 15E, after stapler (200) has been fired, firing assembly (350) is returned to its proximal home position within cartridge channel (206). As firing assembly (350) is advanced proximally, the proximal cam ramp of block finger (372) engages the distal cam ramp of detent finger (324), thereby driving detent finger (324) downwardly and rotating detent member (304) in the counter-clockwise direction against the bias of torsion spring (340). As firing assembly (350) reaches the proximal home position shown in FIG. 15E, block finger (372) settles within uppercut feature (334) of detent finger (324) and block finger (372) holds detent member (304) in a slightly counter-clockwise position such that proximal hook element (326) no longer obstructs upper tip (255) of clamp lever latch member (254). Accordingly, clamp lever latch member (254) may be actuated to disengage cartridge channel (206) and permit opening of clamp lever (240) for separation of stapler halves (202, 204). It will be appreciated that the detent interaction between detent member (304) and slider block (352) as described above provides an operator with a tactile indication of when firing assembly (350) is separated from and returned to its proximal home position, thereby signaling to the operator when it is safe to open clamp lever (240) and separate stapler halves (202, 204).

C. Firing Assembly of Linear Surgical Stapler

FIGS. 16-21 show additional details of firing assembly (350) of linear surgical stapler (200). As shown best in FIG. 16, firing assembly (350) of the present example includes a slider block (352), a pair of actuators (354, 356) (or "firing knobs") pivotably coupled to slider block (352), and a plurality of elongate beams (358, 360) extending distally from slider block (352). A pair of side beams (358) are coupled at their proximal ends to a distal end of slider block (352) and terminate distally in a pair of cam ramps (360). Cam ramps (360) are configured to actuate staple drivers (not shown) housed within staple cartridge (230) to fire staples (not shown) from cartridge (230), in a manner similar to cam ramps (106) of sled (100) described above. A center beam (362) is coupled with side beams (358) via a bridge element (364) spaced distally from slider block (352). Center beam (362) terminates distally in an angled knife member (366) having a distal cutting edge (368) configured to cut tissue clamped between the distal portions of stapler halves (202, 204). Firing assembly (350) is operable to be driven distally through cartridge channel (206) to simultaneously cut and staple tissue clamped between stapler halves (202, 204), in response to an operator pushing distally on an exposed one of actuators (354, 356) as described below.

Figure 17:
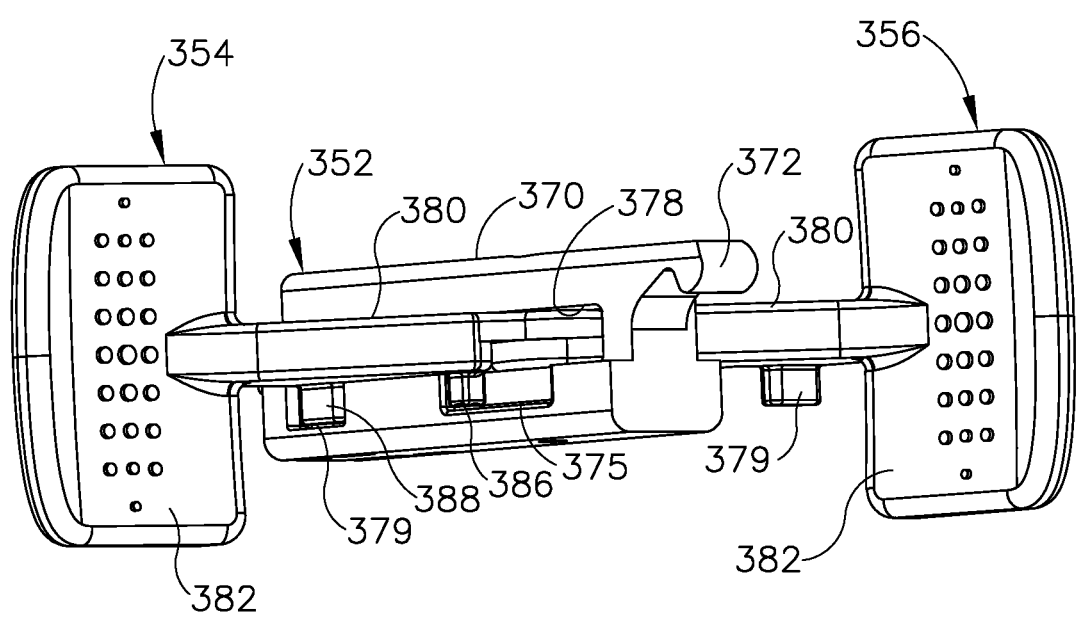
FIG. 17 depicts a proximal perspective view of the slider block and the rotatable actuators of the firing assembly of FIG. 16.
Figure 19:
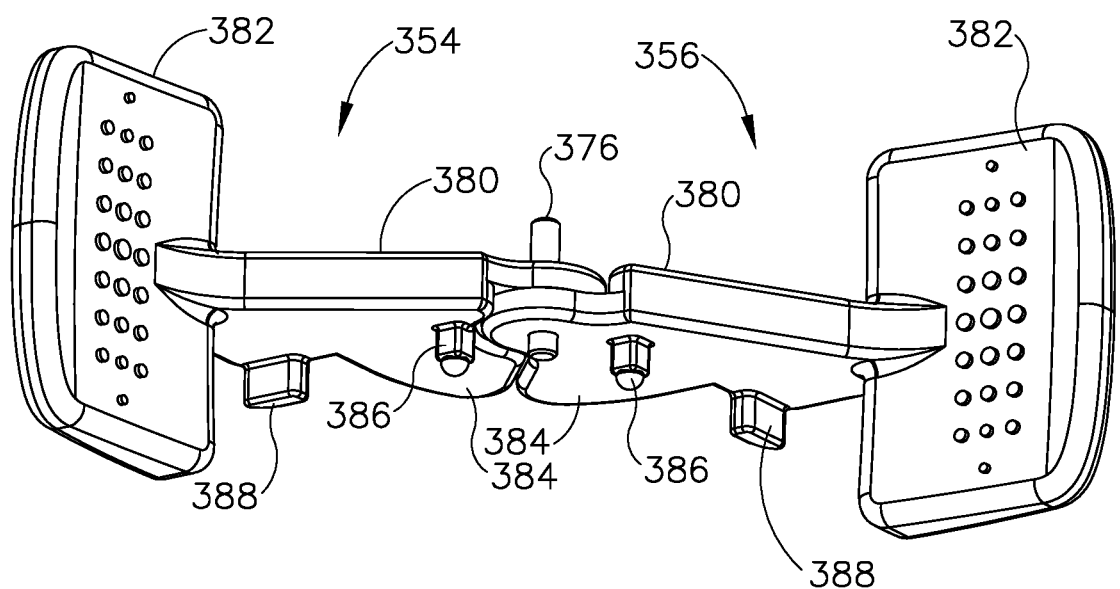
FIG. 19 depicts a bottom perspective view of the rotatable actuators of the firing assembly of FIG. 16.

As shown best in FIGS. 17-19, actuators (354, 356) are rotationally coupled to slider block body (370) with a pivot pin (376) such that each actuator (354, 356) extends outwardly from a respective lateral side of block body (370) and is configured to rotate through a lateral opening (378) formed in block body (370). Each actuator (354, 356) includes an actuator body (380) and a paddle (382) extending transversely from an outer end of actuator body (380), such that actuator bodies (380) are generally horizontal and paddles (382) are generally vertical in the orientations depicted herein. As shown in FIG. 19, each actuator body (380) includes a wedge feature (384) at its inner end that is configured to move through lateral opening (378) of block body (370). Wedge features (384) are configured to abut one another such that each actuator (354, 356) is configured automatically, rotationally retract relative to slider block (352) when the opposing actuator (354, 356) is rotationally exposed by an operator, as described in greater detail below in connection with FIGS. 20A and 20B.

As seen best in FIGS. 17 and 19, each actuator body (380) further includes a detent projection (386) and a stop tab (388) projecting downwardly from a lower surface of actuator body (380). Each detent projection (386) is configured to slidably engage a respective detent groove (375) formed in the proximal portion of a respective lateral side of slider block body (370). Each stop tab (388) is configured to be received within a recess (379) formed in the distal portion of a respective lateral side of slider block body (370). As each actuator (354, 356) rotates between a retracted rotational positional and an exposed rotational position, its detent projection (386) slides longitudinally within the respective detent groove (375). Additionally, as an actuator (354, 356) is rotated from its exposed rotational position to its retracted rotational position, its stop tab (388) is received within and abuts an inner side wall of the respective recess (379).

Actuators (354, 356) of linear surgical stapler (200) are configured to enable dual-sided firing of stapler (200) such that stapler (200) may be fired by driving an actuator (354, 356) distally along either lateral side of stapler (200). Actuators (354, 356) are further configured such that at least one actuator (354, 356) remains retracted at all times to prevent an unused actuator (354, 356) from interfering with an operator's ability to securely grip stapler (200) with a supporting hand while firing stapler (200) with a firing hand. As described below, each actuator (354, 356) of the present version is rotatable relative to slider block (352) by approximately 90 degrees between a retracted rotational position and an exposed rotational position.

Figure 20A:
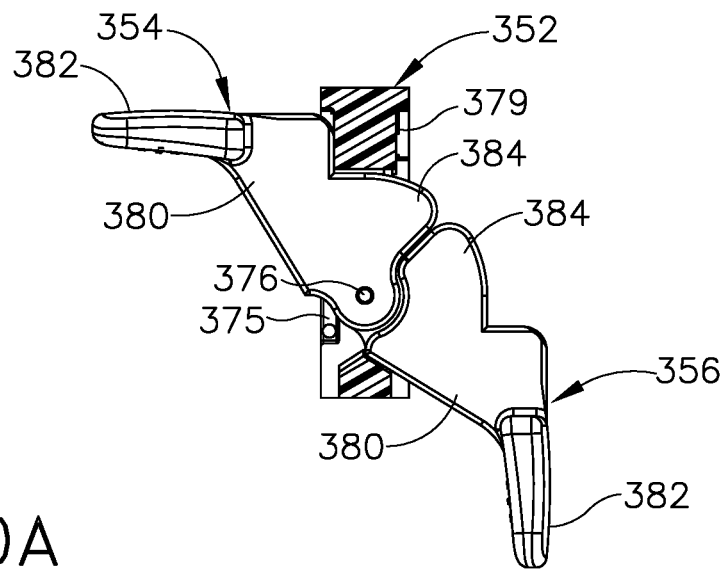
FIG. 20A depicts a top cross-sectional view of the slider block and rotatable actuators of the firing assembly of FIG. 16, showing the actuators in a first configuration in which the first actuator is in an extended rotational position and the second actuator is in a retracted rotational position.

FIG. 20A shows first actuator (354) in an exposed rotational position in which its paddle (382) is oriented distally and extends transversely to a longitudinal axis of firing assembly (350), and second actuator (356) in a retracted rotational position in which its paddle (382) is oriented proximally and extends parallel to the longitudinal axis. In this configuration, an operator may grip, with a first hand, the second lateral side of stapler (200) along which paddle (382) of second actuator (356) is retracted, and simultaneously drive with a second hand the exposed paddle (382) of first actuator (354) distally to perform a firing stroke.

Figure 20B:
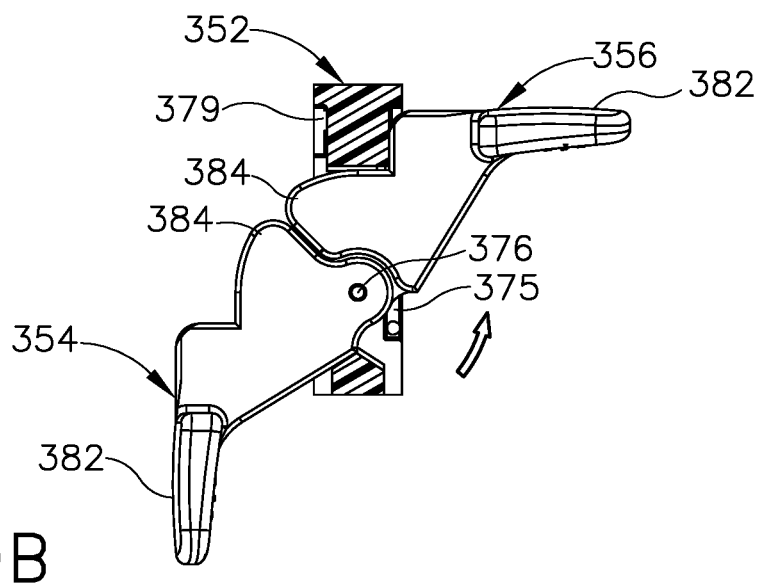
FIG. 20B depicts a top cross-sectional view of the slider block and actuators of the firing assembly of FIG. 16, showing the actuators in a second configuration in which the first actuator is retracted and the second actuator is extended.

FIG. 20B shows actuators (354, 356) in an opposite orientation achieved by driving paddle (382) of retracted second actuator (356) distally to rotate second actuator body (380) about pin (376) such that wedge feature (384) of second actuator (356) drives against wedge feature (384) of first actuator (354). This interaction causes first actuator (354) to automatically rotate from an exposed rotational position to a retracted rotational position, shown in FIG. 20B. In this configuration, an operator grips, with a first hand, the first lateral side of stapler (200) along which paddle (382) of first actuator (354) is retracted, and simultaneously drive with a second hand the exposed paddle (382) of second actuator (356) distally to perform a firing stroke. It will be appreciated that second actuator (356) may also automatically rotate from its exposed rotational position to its retracted rotational position in response to rotation of first actuator (354).

Figure 20C:
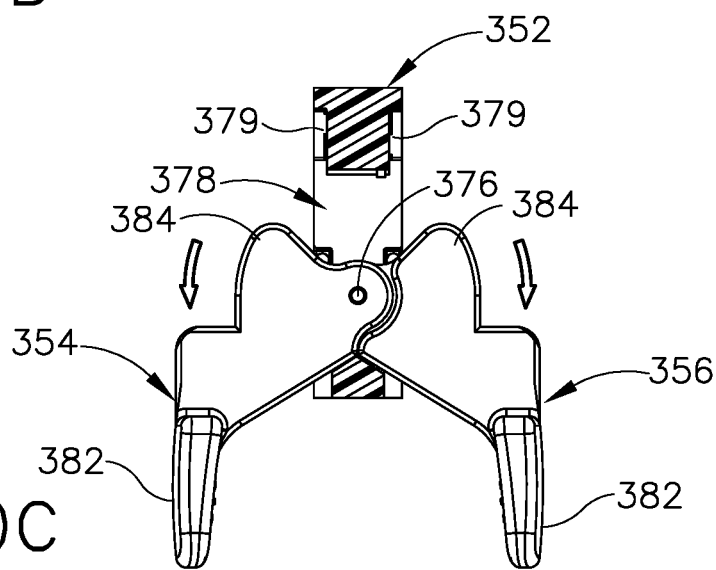
FIG. 20C depicts a top cross-sectional view of the slider block and actuators of the firing assembly of FIG. 16, showing the actuators in a third configuration in which both actuators are retracted.

FIG. 20C shows both actuators (354, 356) in retracted rotational positions in which both paddles (382) are oriented proximally such that they extend generally parallel to the longitudinal axis of firing assembly (350). Such a configuration may provide surgical stapler (200) with a compact profile suitable for device packaging and other storage or transportation purposes, for example.

Figure 21:
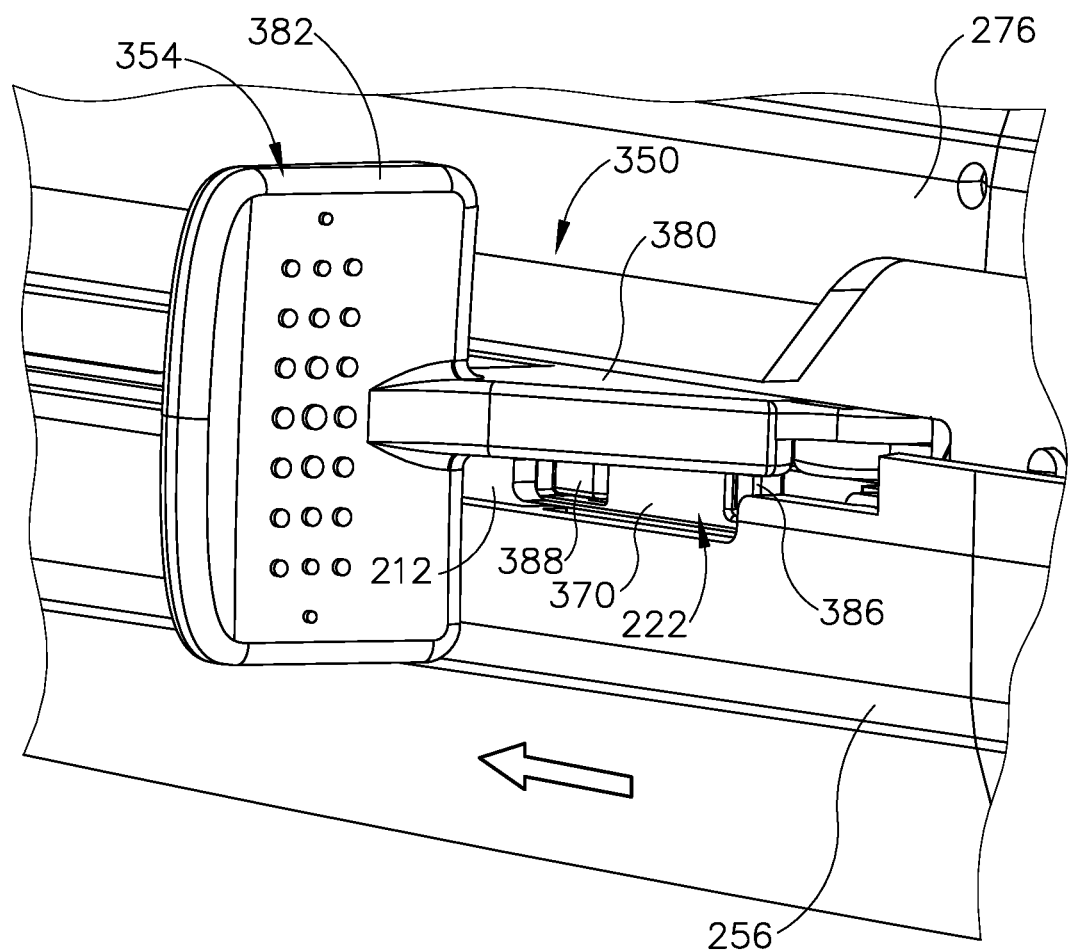
FIG. 21 depicts an enlarged perspective view of a proximal portion of the linear surgical stapler of FIG. 6, showing a lower tab of an actuator of the firing assembly of FIG. 16 being constrained against an inner surface of the cartridge channel as the firing assembly is advanced distally.

As shown in FIGS. 7 and 21, the proximal portion of each longitudinal firing slot (222) of cartridge channel (206) is suitably shaped to permit the respective actuator (354, 356) to rotate between its retracted and exposed positions while firing assembly (350) is in its proximal home position. Once firing assembly (350) is actuated distally during a firing stroke, firing slots (222) prevent actuators (354, 356) from rotating until firing assembly (350) is returned to its proximal home position following completion of the firing stroke. For instance, FIG. 21 shows first actuator (354) in an exposed position and being driven distally through a respective longitudinal firing slot (222) such that its stop tab (388), and subsequently its detent projection (386), are captured between slider block body (370) and a confronting inner surface of the respective side flange (212) of cartridge channel (206). Accordingly, stop tab (388) and detent projection (386) of first actuator (354) become constrained to prevent unintentional rotation of first actuator (354) from its exposed position to its retracted position while stapler (200) is being fired. It will be understood that second actuator (356) is constrained in a similar manner by slider block body (370) and the adjacent cartridge channel side flange (212) when second actuator (356) is in the exposed position and is being driven distally to fire stapler (200).

III. Exemplary Linear Surgical Stapler having Proximal Decoupling Mechanism and Extendable Distal Tip In some instances, it may be desirable to provide linear surgical stapler (200) with one or more additional features that facilitate decoupling of the proximal ends of stapler halves (202, 204). As described below, FIGS. 22-27 show another exemplary linear surgical stapler (400) having exemplary versions of such decoupling features, and which is otherwise similar to stapler (200) described above except as otherwise described below.

A. Overview of Linear Surgical Stapler

Figure 22:
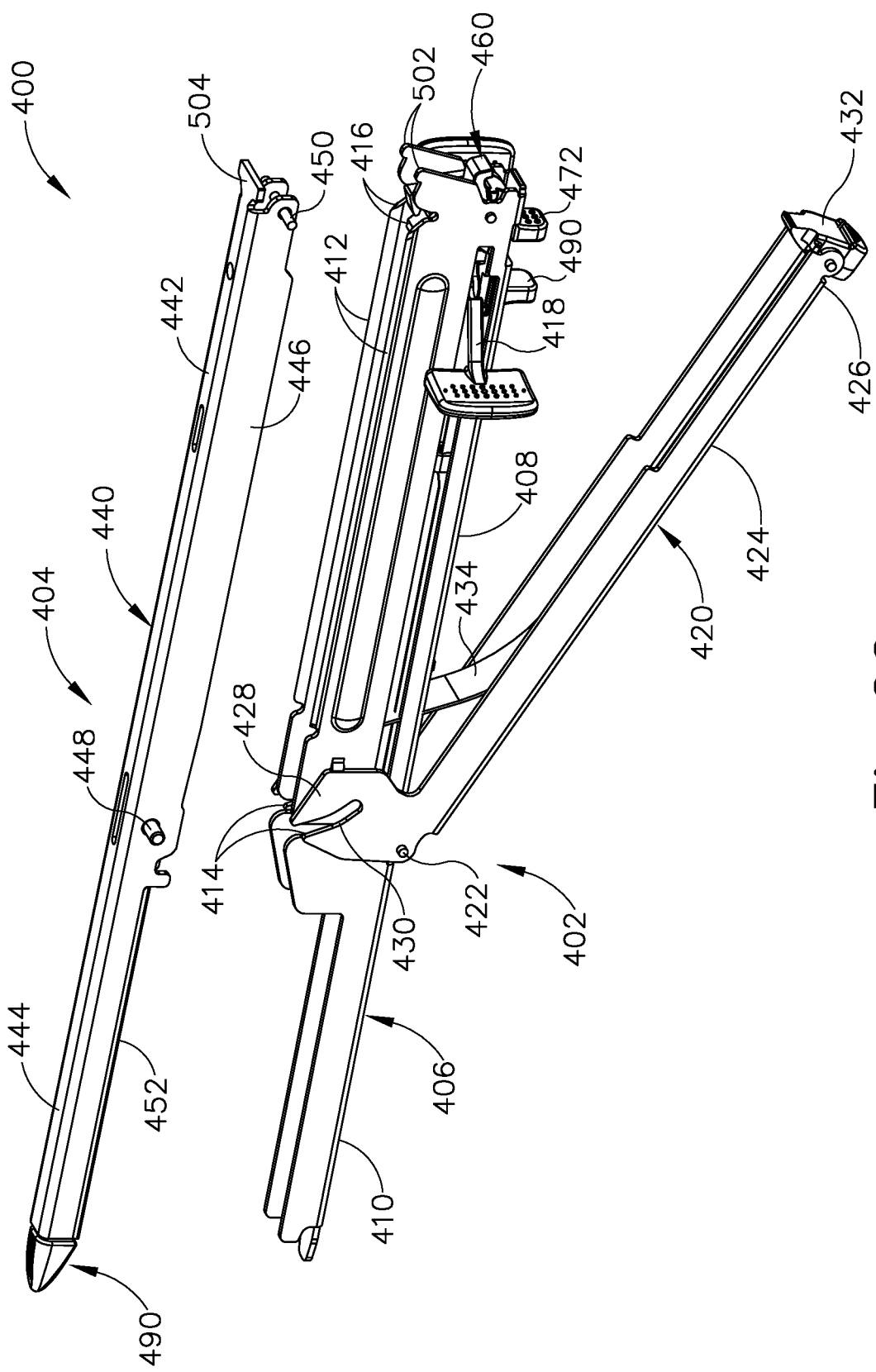
FIG. 22 depicts a perspective view of another exemplary linear surgical stapler having a cartridge half and an anvil half, showing the stapler halves separated from one another, with shrouds of the stapler halves and a staple cartridge being omitted.

As shown in FIG. 22, linear surgical stapler (400) includes a cartridge half (402) (or "reload half") and an anvil half (404) configured to releasably couple together to clamp tissue therebetween for simultaneous cutting and stapling of the clamped tissue. Though not shown in FIG. 22, stapler halves (402, 404) may include shrouds similar to shrouds (256, 276) described above, for example as shown in FIGS. 31A and 31B.

Cartridge half (402) includes an elongate cartridge channel (406) having a proximal frame portion (408) and a distal jaw portion (210). Proximal frame portion (408) slidably retains a firing assembly (418) similar to firing assembly (350) described above, and includes a laterally opposed pair of upright side flanges (412). Each side flange (412) includes a vertical slot (414) arranged at a distal end thereof, and a tapered notch (416) arranged at a proximal end thereof. Distal jaw portion (410) of cartridge channel (406) is configured to receive a staple cartridge (or "reload") (not shown), which may be similar to staple cartridge (230) described above.

Cartridge half (402) further includes a clamp lever (420) pivotably coupled to cartridge channel (406) with clamp lever pivot pin (422). Clamp lever (420) includes an elongate lever arm (424) having a free proximal end (426) and a distal end pivotably coupled to cartridge channel (406) and having a pair of opposed jaws (428). Each jaw (428) has a curved camming slot (430) configured to capture a respective lateral end of distal anvil pin (448) of anvil half (404). Clamp lever (420) further includes a clamp lever latch member (432) arranged at proximal end (426) of lever arm (424) and configured to engage a proximal end of cartridge channel (406) to releasably retain clamp lever (240) in the closed position during firing. Clamp lever (420) is resiliently biased toward an open position by a resilient member in the form of a flat spring (434).

Anvil half (404) of linear surgical stapler (400) includes an elongate anvil channel (440) having a proximal frame portion (442) and a distal jaw portion (446). Proximal frame portion (442) includes a laterally opposed pair of upright side flanges (446) that are configured to be received between cartridge channel side flanges (412) when anvil half (404) is coupled with cartridge half (402). A distal anvil pin (448) extends laterally through the distal ends of anvil channel side flanges (446), and a proximal anvil pin (450) extends laterally through the proximal ends of anvil channel side flanges (446). Anvil pins (448, 450) are configured to facilitate coupling of anvil half (404) with cartridge half (402) similar to anvil pins (268, 270) described above. Distal jaw portion (444) of anvil half (404) supports an anvil surface (452) having a plurality of staple forming pockets (454) (see FIG. 28) configured to deform the legs of staples ejected by a staple cartridge (not shown) when stapler (400) is fired. Distal jaw portion (446) of anvil half (404) additionally supports an extendable distal tip member (510), described in greater detail below.

B. Proximal Retaining Assembly having Anvil Pin Ejection Feature

Figure 23:
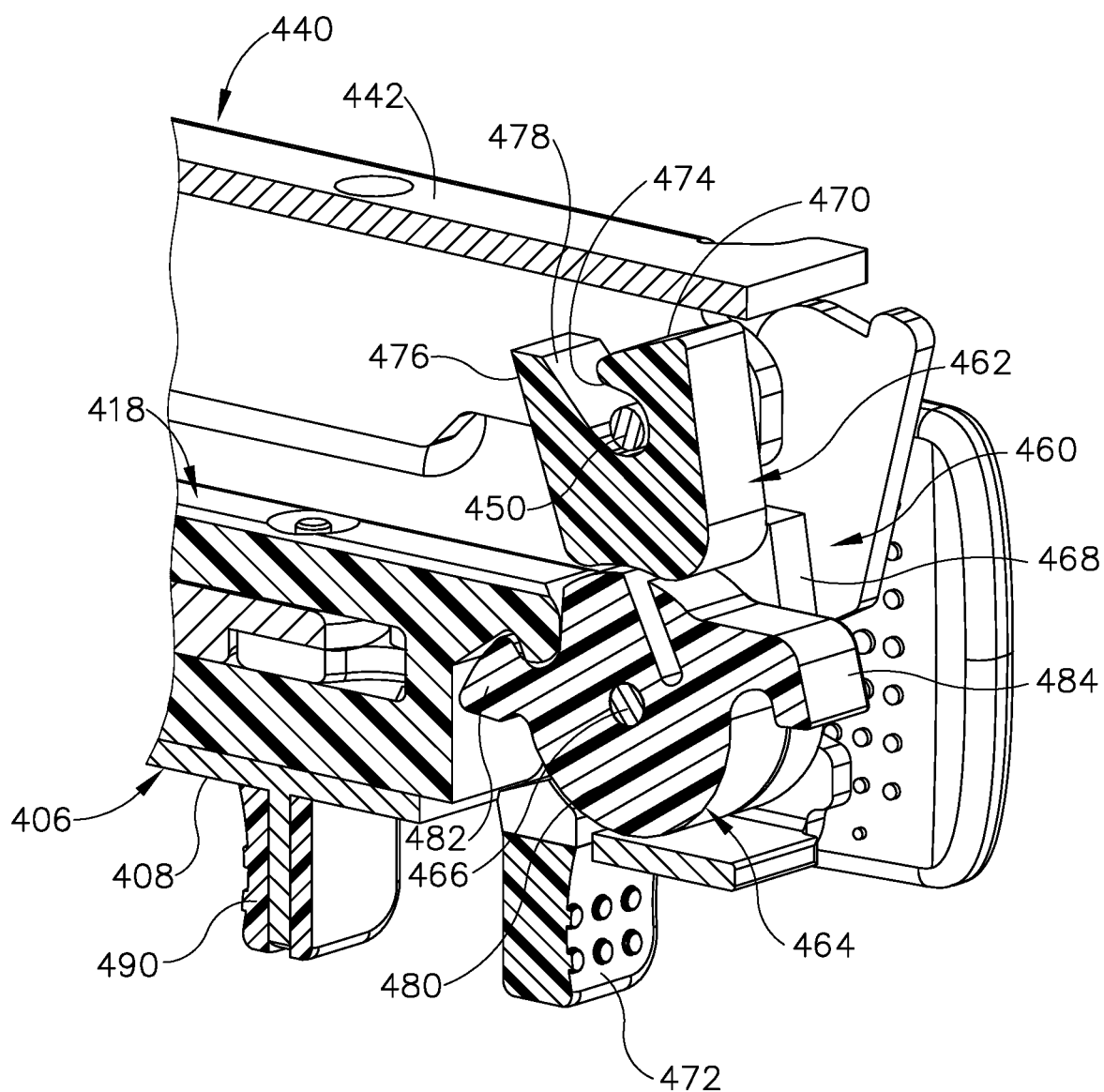
FIG. 23 depicts a side cross-sectional view of a proximal portion of the linear surgical stapler of FIG. 22, showing details of a proximal retaining assembly of the cartridge half having a latch member that releasably captures a proximal pin of the anvil half to couple proximal ends of the stapler halves together.
Figure 24A:
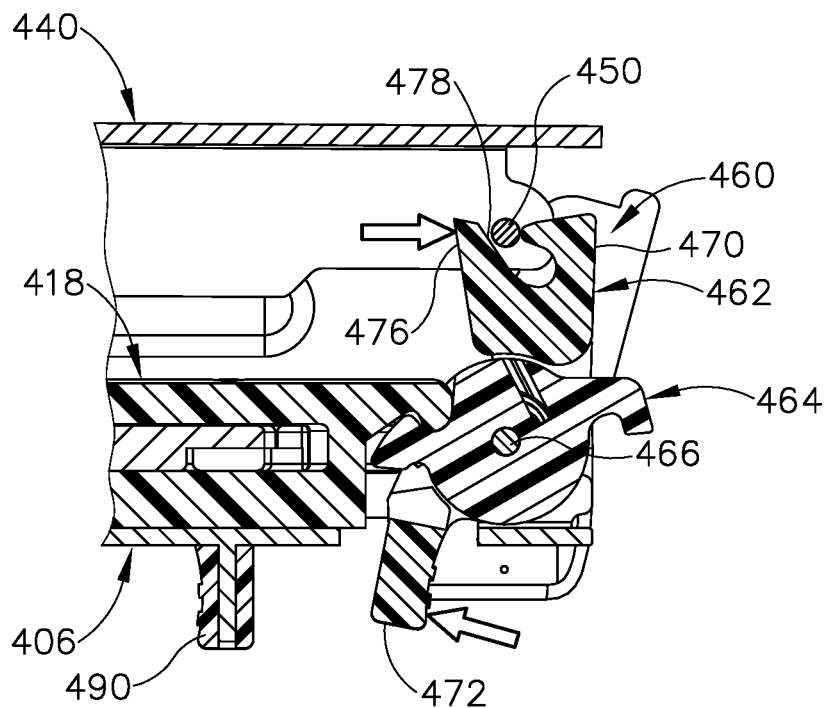
FIG. 24A depicts a side cross-sectional view of the proximal portion of the linear surgical stapler of FIG. 22, showing actuation of a release button of the latch member to release and eject the proximal pin of the anvil half from the cartridge half.
Figure 24B:
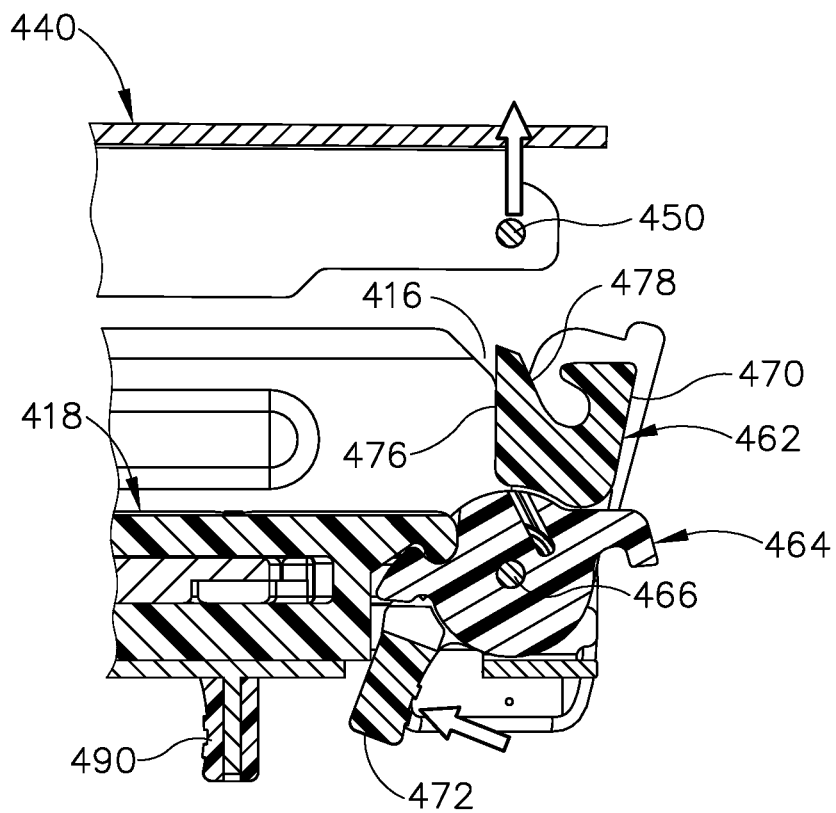
FIG. 24B depicts a side cross-sectional view of the proximal portion of the linear surgical stapler of FIG. 22, showing the proximal ends of the stapler halves decoupled from one another following actuation of the latch member release button.

FIGS. 23-24B show details of a proximal retaining assembly (460) arranged at a proximal end of linear surgical stapler (400), and which is similar to proximal retaining assembly (300) of stapler (200) described above except as otherwise described below. Proximal retaining assembly (460) includes an anvil latch member (462) and a detent member (464), both of which are rotatably coupled with a proximal end of cartridge channel (406) via a laterally extending pin (466). Anvil latch member (462) and detent member (464) are configured to rotate independently about pin (466), and are resiliently biased in opposite rotational directions by a torsion spring (not shown), similar to torsion spring (340) described above.

As shown best in FIG. 23, anvil latch member (462) includes a central body (468), a latch finger (470) extending upwardly from central body (308), and a release button (472) extending downwardly from central body (468) through a base wall of proximal frame portion (408) of cartridge channel (406). An upper end of latch finger (470) tapers distally and is configured to releasably capture proximal anvil pin (450) of anvil half (404) with an angled latching surface (474) that overlies proximal anvil pin (450) once captured. Anvil latch member (462) further includes a pin ejection feature in the form of an angled projection (476) extending distally from a base portion of latch finger (470) and which defines an ejection cam ramp (478) that faces proximally toward latch finger (470).

Detent member (464) of proximal retaining assembly (460) is similar in structure and function to detent member (304) described above. In particular, detent member (464) includes a generally cylindrical central body (480), a distal finger (482) extending distally from central body (480), and a proximal hook element (484) extending proximally from central body (480). Distal finger (482) is configured to releasably engage and retain firing assembly (418) in a proximal home position. Proximal hook element (484) is configured to overlie and capture an upper tip of clamp lever latch member (432) when clamp lever (420) is closed and firing assembly (418) is translated distally from its proximal home position, thereby preventing clamp lever (420) from opening during a firing stroke, for example as described in U.S. patent application Ser. No. 16/102,170, published as U.S. Pub. No. 2020/0046353 on Feb. 13, 2020, incorporated by reference above.

As shown in FIGS. 24A and 24B, with clamp lever (420) in the open position, distal actuation of lower release button (472) causes anvil latch member (462) to rotate about pin (466) such that ejection cam ramp (478) advances proximally to drive proximal anvil pin (450) upwardly out of proximal tapered notches (416) of cartridge channel (406). Cartridge half (402) of the present version includes a stationary gripping projection (490) that extends downwardly from a base wall of proximal frame portion (408) of cartridge channel (406) at a location distal to lower release button (472), and is configured to facilitate actuation of release button (472). In particular, a user may apply his or her thumb to a proximal side of release button (472) and one or more fingers to a distal side of gripping projection (490), and then squeeze release button (472) distally toward stationary gripping projection (490) to rotate latch finger (470) out of engagement with proximal anvil pin (450) and eject pin (450) upwardly from cartridge channel (406) with ejection cam ramp (478).

C. Decoupling Mechanism having Engageable Stop Tabs

Figure 25:
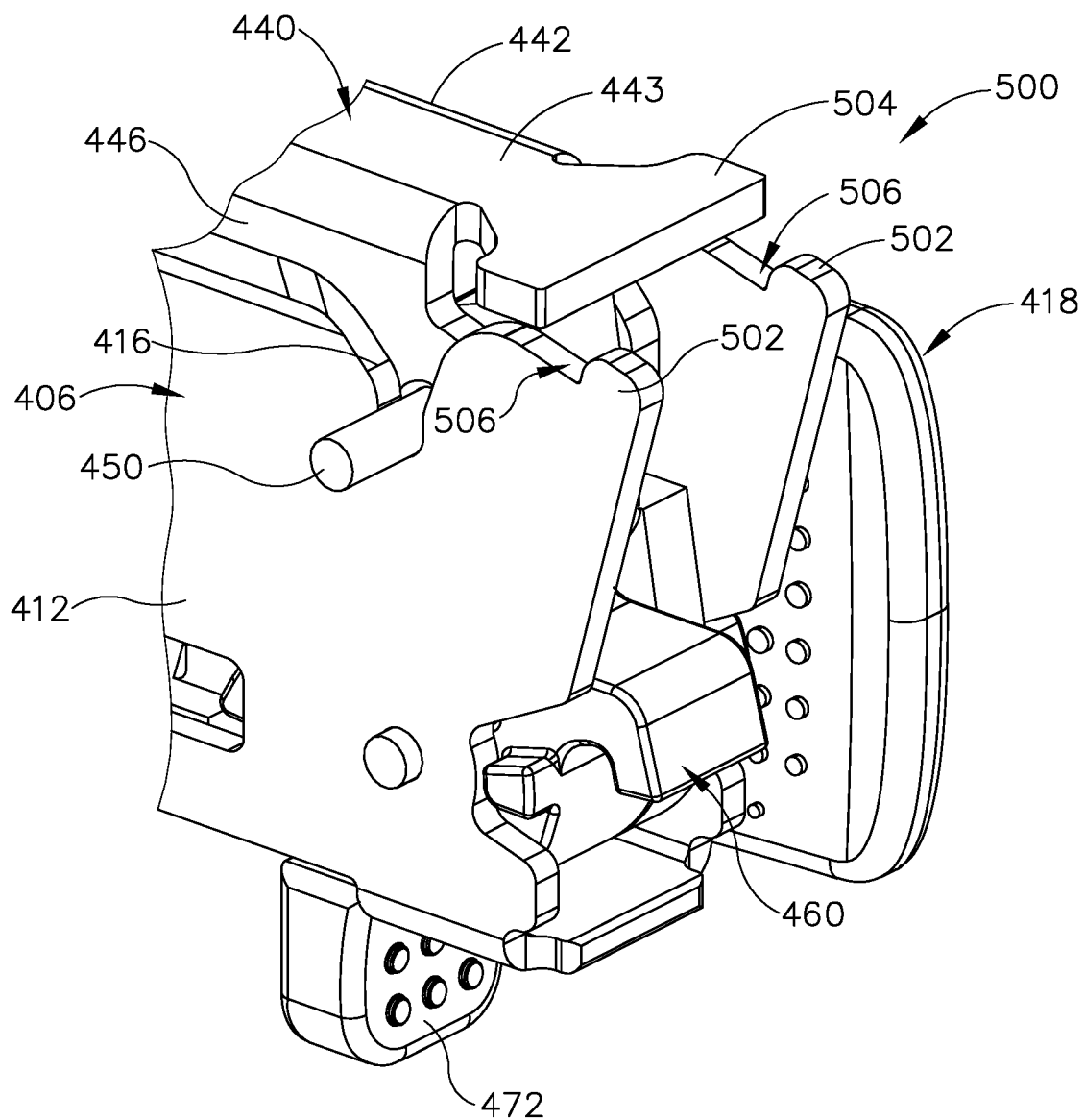
FIG. 25 depicts a perspective view of a proximal portion of the linear surgical stapler of FIG. 22, showing details of an exemplary decoupling mechanism arranged at the proximal end of the stapler.

As shown in FIG. 25, a proximal end of linear surgical stapler (400) of the present example further includes a decoupling mechanism (500). As described in greater detail below, decoupling mechanism (500) is configured to release proximal anvil pin (450) from latch finger (470) of anvil latch member (462) and thereby decouple the proximal ends of stapler halves (402, 404) from one another in response to anvil half (404) being pivoted away from cartridge half (402) when clamp lever (420) is open. Accordingly, decoupling mechanism (500) is configured to decouple the proximal ends of stapler halves (402, 404) from one another without user-actuation of lower release button (472), such that decoupling mechanism (500) may be used as an alternative to release button (472) at the user's preference.

Decoupling mechanism (500) of the present example includes a pair of laterally opposed cartridge channel stop tabs (502) and an anvil channel stop tab (504) configured to engage and pivot relative to cartridge channel stop tabs (502) in a lever-fulcrum arrangement. Each cartridge channel stop tab (502) is defined by a proximal end of a respective cartridge channel side flange (412) and projects vertically at a location proximal to the respective tapered notch (416) to define a corresponding fulcrum notch (506) positioned along a distal face of cartridge channel stop tab (502). Anvil channel stop tab (504) projects proximally from the proximal end of a base wall (443) of anvil channel (440), and has a T-like shape defining a lateral width that increases proximally. Anvil channel stop tab (504) of the present example has a maximum lateral width at its proximal end that is equal to or greater than an outer lateral width of cartridge channel (406) defined by cartridge channel stop tabs (502). Accordingly, the proximal end of anvil channel stop tab (504) has a lateral width that is greater than an outer lateral width defined by anvil channel side flanges (446).

As shown in FIGS. 26A-26E, anvil half (404) is configured to pivot away from cartridge half (402) through successive first and second ranges of motion about respective first and second lateral pivot axes to thereby release proximal anvil pin (450) from proximal latch member (462) without depressing lower release button (472). The first pivot axis is defined by proximal anvil pin (450) when retained within proximal tapered notches (416) of cartridge channel (406) by proximal latch member (462). The second pivot axis is arranged proximal to the first pivot axis and is defined by a lateral line of contact established between the distal faces of cartridge channel stop tabs (502) and the proximal face of anvil channel stop tab (504) as the opposed lateral ends of anvil channel stop tab (504) are received within fulcrum notches (506).

Figure 26A:
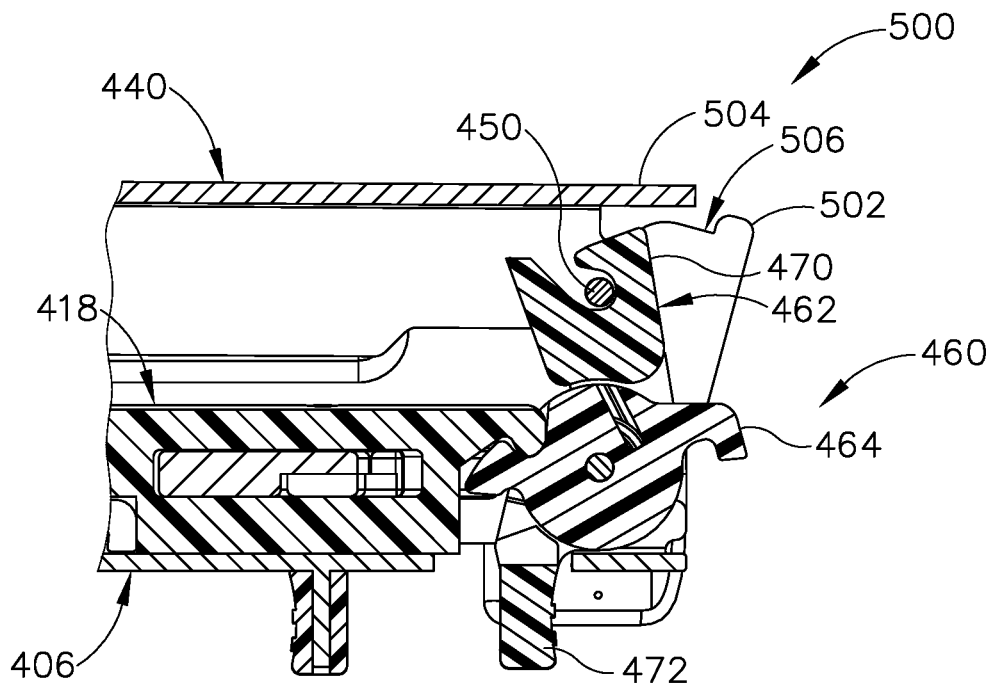
FIG. 26A depicts a side cross-sectional view of the proximal portion of the linear surgical stapler of FIG. 22, showing the proximal pin of the anvil half captured by the latch member of the cartridge half so that the proximal ends of the stapler halves are pivotably coupled.
Figure 26B:
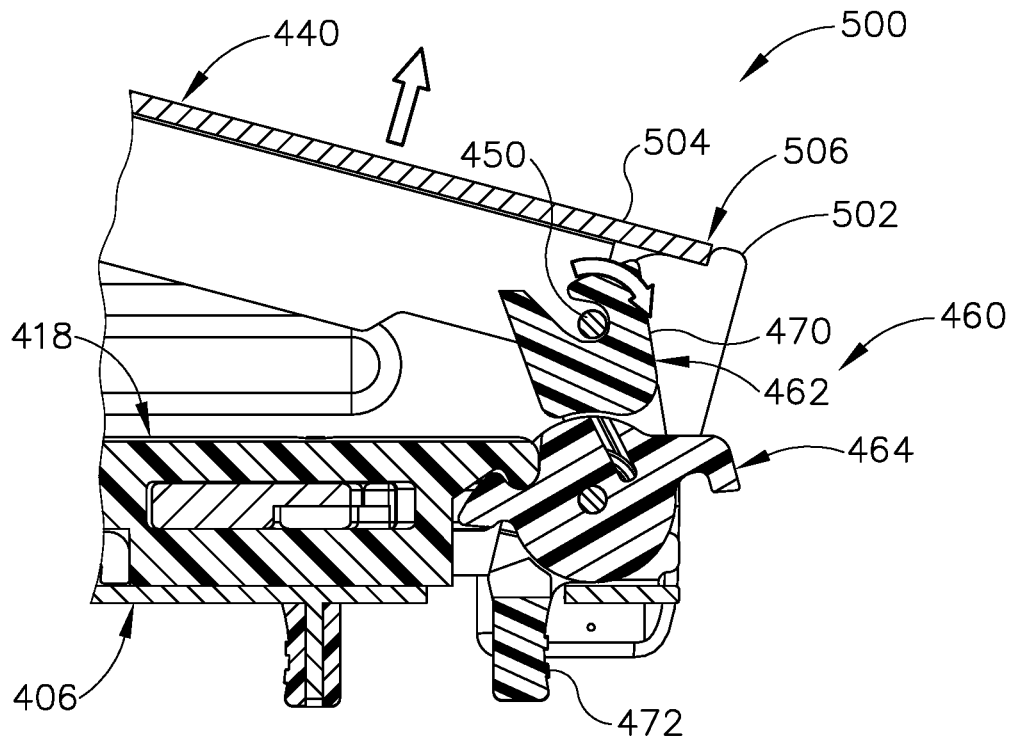
FIG. 26B depicts a side cross-sectional view of the proximal portion of the linear surgical stapler of FIG. 22, showing the anvil half pivoting away from the cartridge half through a first range of motion about a first pivot axis defined by the proximal anvil pin.

FIG. 26A shows the proximal ends of stapler halves (402, 404) in an initial state in which anvil channel (440) extends generally parallel to cartridge channel (406) and in which clamp lever (420) is open. Proximal anvil pin (450) is fully seated within proximal tapered notches (416) of cartridge channel (406) and is pivotably retained therein by latch finger (470) of proximal latch member (462). FIG. 26B shows stapler halves (402, 404) in a second state in which anvil channel (440) has been pivoted away from cartridge channel (406) through a first range of motion about the first pivot axis defined by proximal anvil pin (450). Upon reaching the end of this first range of motion, the proximal end of anvil channel stop tab (504) is received with fulcrum notches (506) and abuts the distal faces of cartridge channel stop tabs (502).

Figure 26C:
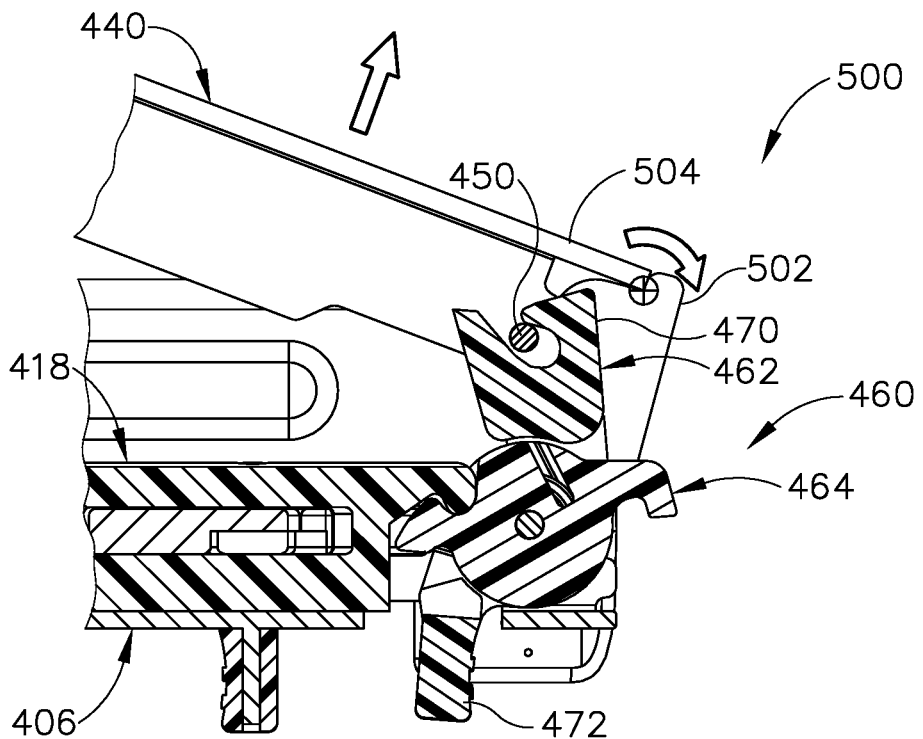
FIG. 26C depicts a side cross-sectional view of the proximal portion of the linear surgical stapler of FIG. 22, showing the anvil half transitioning to a second range of motion through which the anvil half pivots away from the cartridge half and about a second pivot axis defined by the decoupling features of the stapler halves.
Figure 26D:
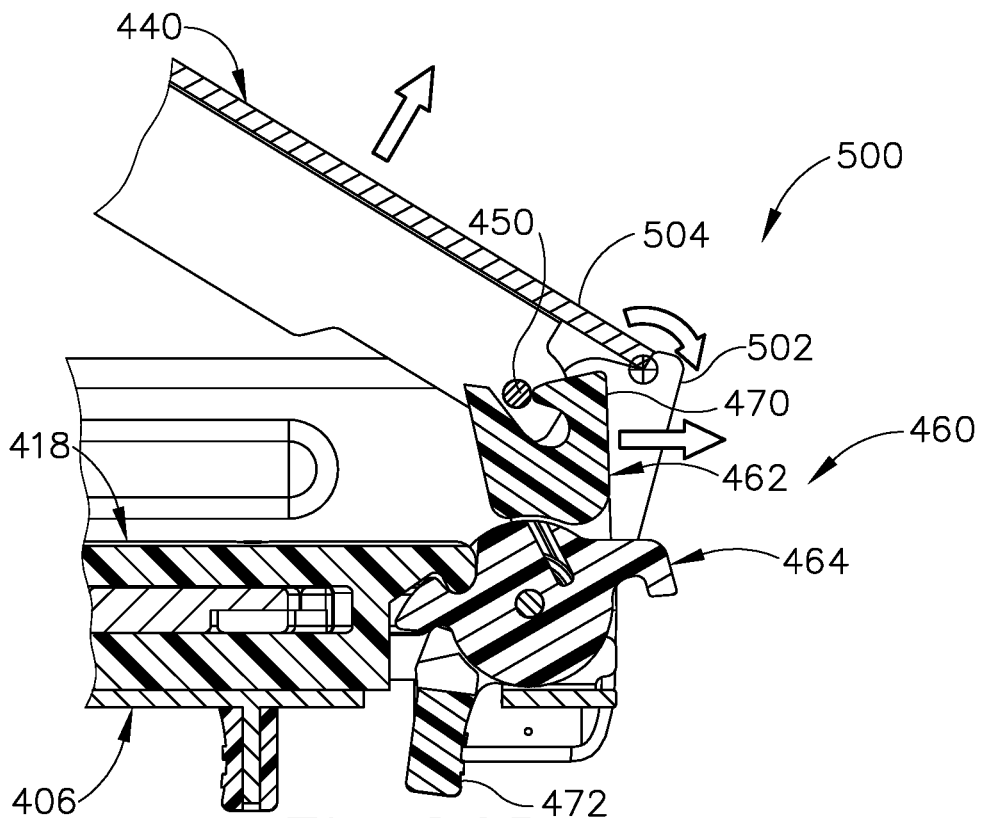
FIG. 26D depicts a side cross-sectional view of the proximal portion of the linear surgical stapler of FIG. 22, showing the anvil half pivoting through the second range of motion about the second pivot axis such that the proximal anvil pin drives the latch member proximally and overcomes its distal resilient bias.
Figure 26E:
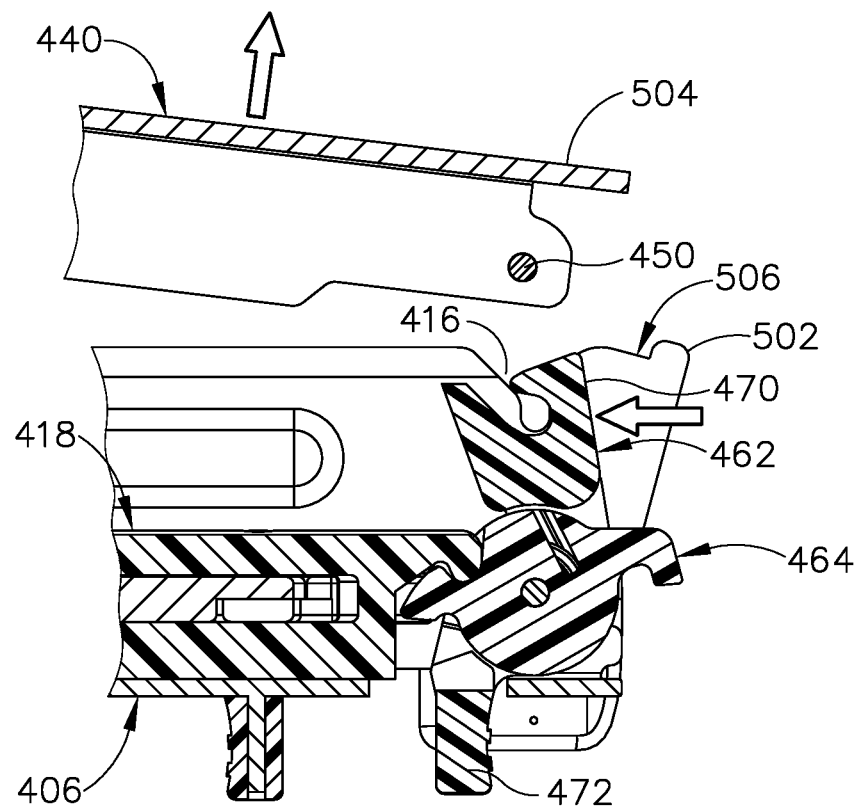
FIG. 26E depicts a side cross-sectional view of the proximal portion of the linear surgical stapler of FIG. 22, showing the proximal ends of the stapler halves decoupled from one another following full travel of the anvil half through the second range of motion about the second pivot axis, showing the latch member returned to its distal position.
Figure 27:
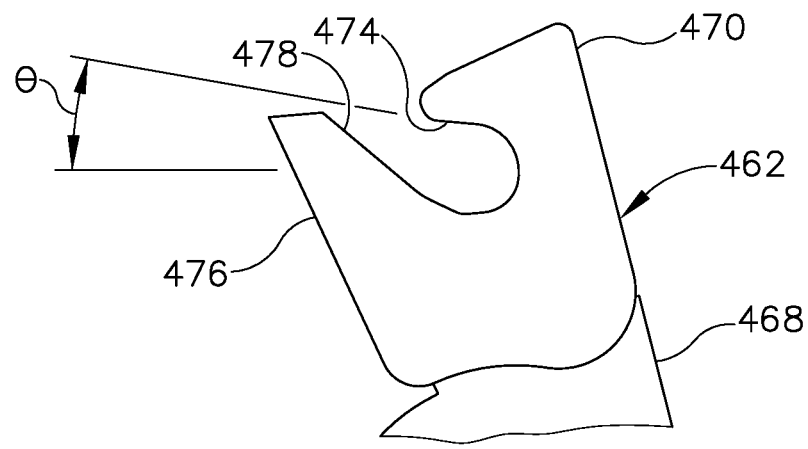
FIG. 27 depicts a side elevational view of an upper portion of the latch member of the cartridge half of FIG. 22, showing an angle defined by a latching surface of the latch member.

As shown in FIGS. 26C and 26D, as anvil channel (440) is pivoted further away from cartridge channel (406) through a second range of motion about the second pivot axis defined by stop tabs (502, 504), proximal anvil pin (450) contacts angled latching surface (474) of latch finger (470) in camming engagement. Continued pivoting of anvil channel (440) through the second range of motion thus causes proximal anvil pin (450) to drive latch finger (470) proximally, overcoming the rotational resilient bias of anvil latch member (462). As shown in FIG. 26E, as anvil channel (440) reaches the end of the second range of motion, proximal anvil pin (450) is fully released from latch member (462) such that pin (450) may be withdrawn vertically from tapered notches (416) of cartridge channel (406) to fully separate the proximal ends of stapler halves (402, 404) from one another. Latch member (462) then automatically returns to its original rotational position under its resilient bias.

It will be appreciated that the requisite torque applied by a user to anvil half (404) to successfully pivot anvil half (404) fully through the second range of motion and thereby lift proximal anvil pin (450) from tapered notches (416) of cartridge channel (406) must be sufficient to overcome the downwardly-directed resistant force exerted by angled latching surface (474) on proximal anvil pin (450). This resistant force is inversely proportional to an angle ($\theta$), shown in FIG. 27, defined by latching surface (474) relative to a longitudinal axis of cartridge half (402). In particular, as latching surface angle ($\theta$) increases, the resistant force exerted by latching surface (474) on proximal anvil pin (250) decreases, thereby decreasing the requisite torque to be applied by the user to anvil half (404) to successfully overcome the rotational resilient bias of anvil latch member (462) and drive latch finger (270) proximally to separate the proximal ends of stapler (400). Accordingly, latching surface (474) may be shaped with any suitable angle ($\theta$) to tune the requisite input torque for decoupling as desired.

D. Decoupling Mechanism Having Proximal Latch Member with Torque Arm Feature

Figure 28A:
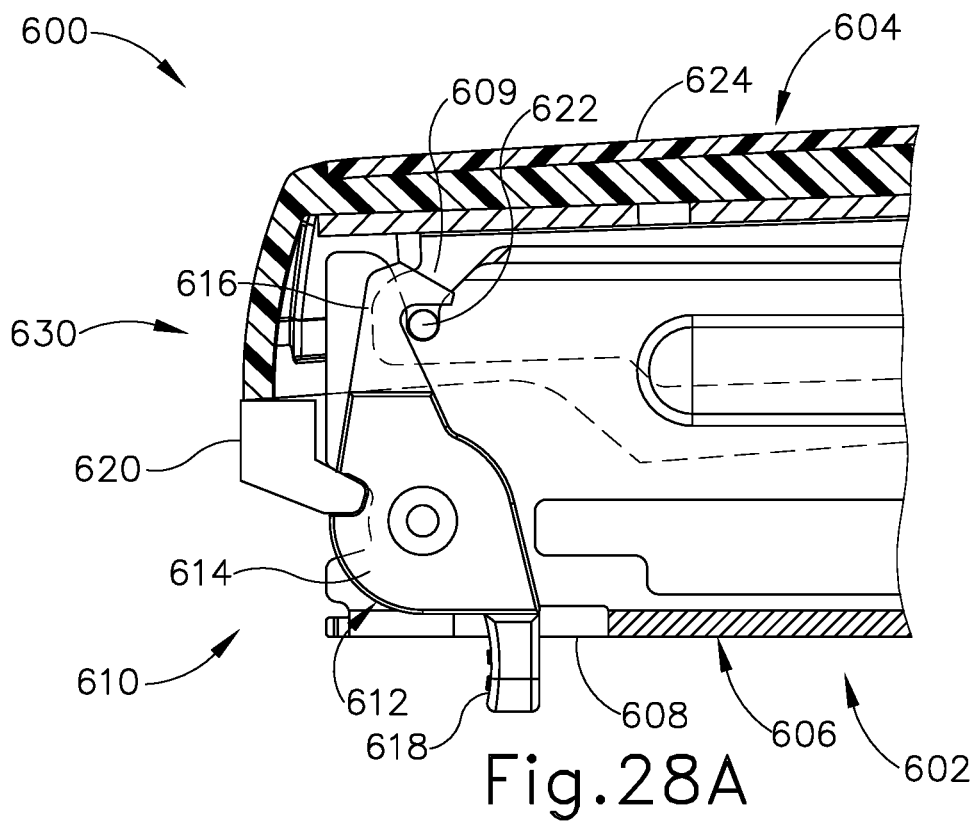
FIG. 28A depicts a side view of a linear surgical stapler having another exemplary decoupling mechanism, showing a proximal latch member of the stapler in a distal latching position.
Figure 28B:
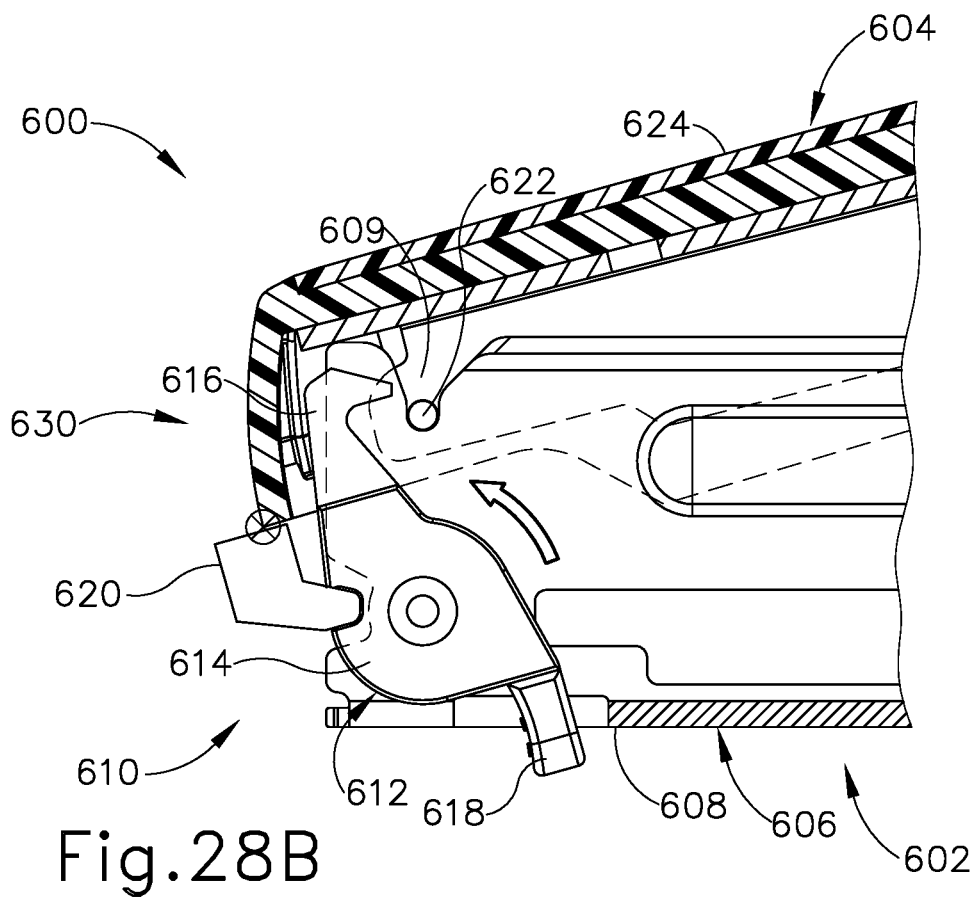
FIG. 28B depicts a side view of the decoupling mechanism of FIG. 28A, showing the proximal latch member rotated to a release position in response to the anvil half of the stapler being pivoted open relative to the cartridge half.

In some instances, it may be desirable to integrate a portion of a decoupling mechanism into the proximal retaining assembly of a linear surgical stapler. FIGS. 28A and 28B depict the proximal end of an exemplary alternative linear surgical stapler (600) having a decoupling mechanism (630)

with such a configuration. Stapler (600) is similar to staplers (200, 400) described except as otherwise described below.

Linear surgical stapler (600) includes a cartridge half (602) and an anvil half (604) configured to releasably couple together to simultaneously cut and staple tissue clamped therebetween. Cartridge half (602) includes an elongate cartridge channel (606) having a proximal frame portion (608) that supports a proximal retaining assembly (610) similar to proximal retaining assemblies (300, 460) described above, except as otherwise described. An anvil latch member (612) of proximal retaining assembly (610) includes a generally cylindrical body (614), a latch finger (616) extending upwardly from body (614), a release button (618) extending downwardly from body (614), and a torque arm (620) extending proximally from body (614). Anvil half (604) of stapler (600) is similar to anvil halves (204, 404) described above in that anvil half (604) includes an elongate anvil channel (not shown) having a proximal frame portion that supports a proximal anvil pin (622), and an anvil shroud (624) coupled to the proximal frame portion. It will be appreciated that cartridge half (602) and anvil half (604) may omit any stop tab features at the proximal ends thereof, for example similar to those shown and/or described above in connection with staplers (200, 400), to accommodate the structure and function of torque arm (620) of anvil latch member (612).

As shown in FIG. 28A, anvil half (604) is configured to be pivoted open relative to cartridge half (602) through a first range of motion about a first pivot axis defined by proximal anvil pin (622) to a predetermined degree at which a proximal end of anvil shroud (624) directly contacts an upper surface of torque arm (620). As shown in FIG. 28B, pivoting anvil half (604) further open through a second range of motion about proximal anvil pin (622) causes the proximal end of anvil shroud (624) to drive torque arm (620) downwardly. This downward motion of torque arm (620) causes anvil latch member (612) to rotate such that latch finger (616) moves proximally to release proximal anvil pin (622). Accordingly, torque arm (620) and the proximal end of anvil shroud (624) cooperate to define a decoupling mechanism (630) that is similar in function to decoupling mechanism (650) described above. In that regard, further opening of anvil half (604) causes anvil half (604) to pivot relative to cartridge half (602) about a second pivot axis defined by the point of contact between torque arm (620) and the proximal end of anvil shroud (624). Similar to arrangement of decoupling mechanism (500), this second pivot axis of decoupling mechanism (630) is located proximal to the first pivot axis defined by proximal anvil pin (622). Pivoting anvil half (604) about this second pivot axis lifts proximal anvil pin (622) from proximal tapered notches (609) of cartridge half (602) while latch member (612) remains in the release position, such that the proximal ends of stapler halves (602, 604) may be separated from one another.

In some such versions, the modified anvil latch member (612) of linear surgical stapler (600) may be suitably resiliently biased toward its distal latching position to resist a predetermined amount of torque applied by the proximal end of anvil shroud (624) via torque arm (620). This may enable a user to hold stapler (600) in a "hang open" configuration in which stapler halves (602, 604) are pivotably opened to the point that the proximal end of anvil shroud (624) rests upon the torque arm (620) of anvil latch member (612). Simultaneously, anvil latch member (612) maintains its distal latching position to prevent decoupling of the proximal ends of stapler halves (602, 604) until the user actively forces anvil half (604) further open relative to cartridge half (602).

E. Extendable Distal Tip Member of Anvil Half

When forming a side-by-side anastomosis between first and second tubular tissue structures, it may be desirable to insert the distal ends of linear surgical stapler (400) into the respective tubular tissue structures successively, rather than simultaneously, to ensure that the distal jaw portion (410, 444) of each stapler half (402, 404) is successfully received within an inner lumen of the respective tissue structure. As described below, extendable distal tip member (510) of anvil half (404) is selectively extendable to provide anvil half (404) with a longer length than cartridge half (402), thereby enabling such use of stapler (400).

Figure 29:
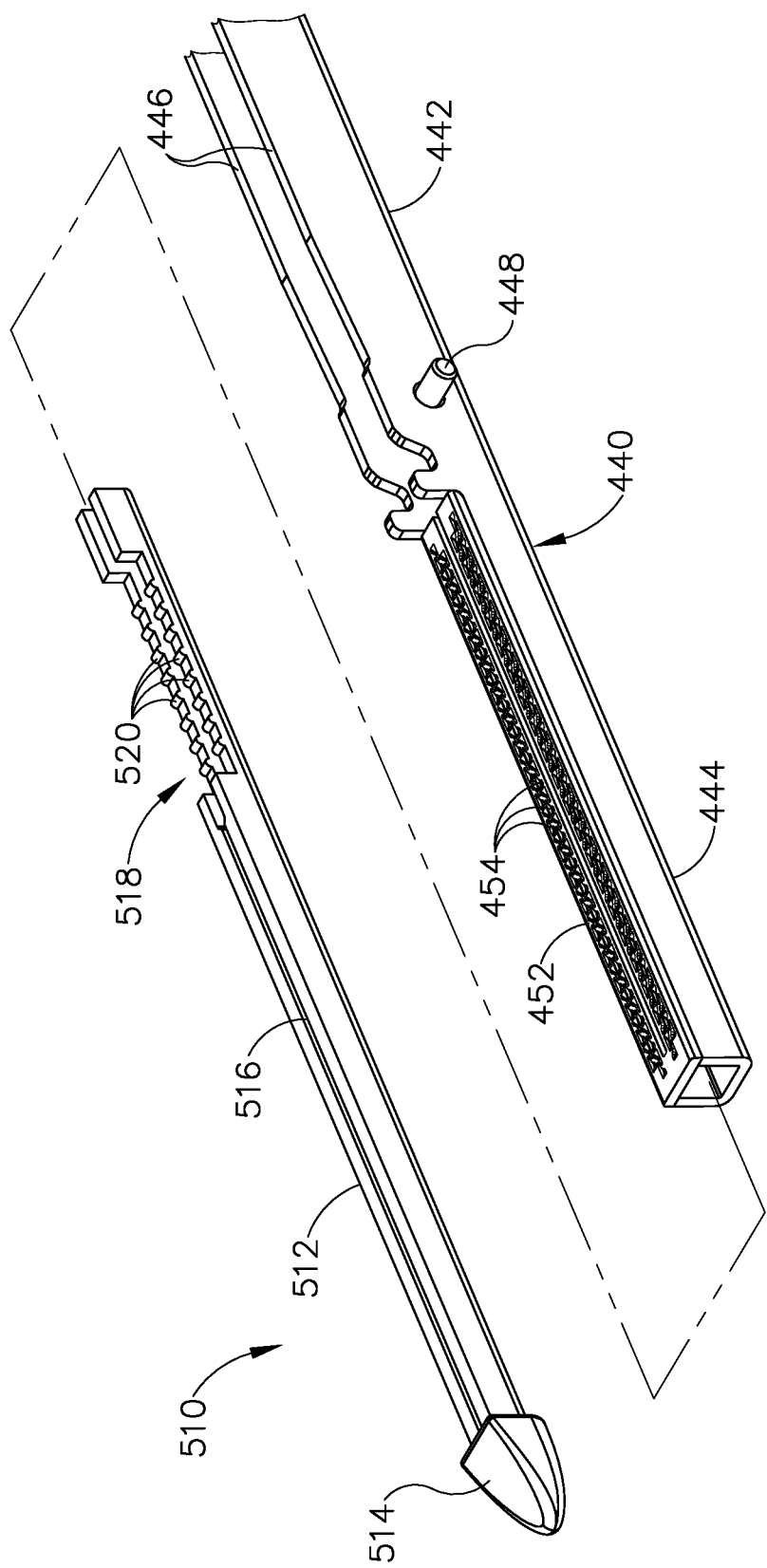
FIG. 29 depicts a disassembled perspective view of a distal portion of the anvil half of the linear surgical stapler of FIG. 22, showing details of an exemplary extendable tip member.

As shown in FIG. 29, extendable distal tip member (510) of the present example includes an elongate body (512) having a cross-sectional shape that corresponds to a cross-sectional shape of an interior of distal jaw portion (444) of anvil channel (440), such that elongate body (512) is slidable within distal jaw portion (444). A tapered distal tip element (514) is arranged at a distal end of elongate body (512) and is configured to remain distal to a distal end of distal jaw portion (444) throughout the various longitudinal positions of tip member (510) described below. Elongate body (512) includes a longitudinal slot (516) in an upper surface thereof through which a knife member (not shown) of firing assembly (418) is configured to translate longitudinally when stapler (400) is fired. A proximal portion of elongate body (512) includes an elongate recess (518) having a base surface along which a plurality of detent bumps (520) are spaced longitudinally.

As shown in FIGS. 30A-30C, detent bumps (520) are configured to resiliently engage an underside of distal anvil pin (448) to releasably retain extendable distal tip member (510) in a corresponding plurality of longitudinal positions relative to anvil channel (440). FIG. 30A shows extendable distal tip member (510) in a fully-retracted proximal position in which distal anvil pin (448) is positioned at a distal end of elongate recess (518). In the fully-retracted position of the present example, a proximal end of elongate body (512) abuts a fin-like inner tab (not shown) of a shroud of anvil half (404), and a proximal end of tapered distal tip element (514) is spaced apart from a distal end of distal jaw portion (444) to define a slight axial gap therebetween.

FIG. 30B shows extendable distal tip member (510) in an exemplary partially-extended position in which distal anvil pin (448) is positioned between an adjacent set of detent bumps (520) within a medial portion of elongate recess (518). FIG. 30C shows extendable distal tip member (510) in a fully-extended distal position in which distal anvil pin (448) is positioned at a proximal end of elongate recess (518). Each longitudinally adjacent set of detent bumps (520) within elongate recess (518) defines a corresponding longitudinal position of extendable distal tip member (510) relative to anvil channel (440). Accordingly, it will be appreciated that elongate recess (518) may be provided with any suitable length and with any suitable quantity of detent bumps (520) to define a corresponding quantity of longitudinal positions for extendable distal tip member (510).

Figure 31A:
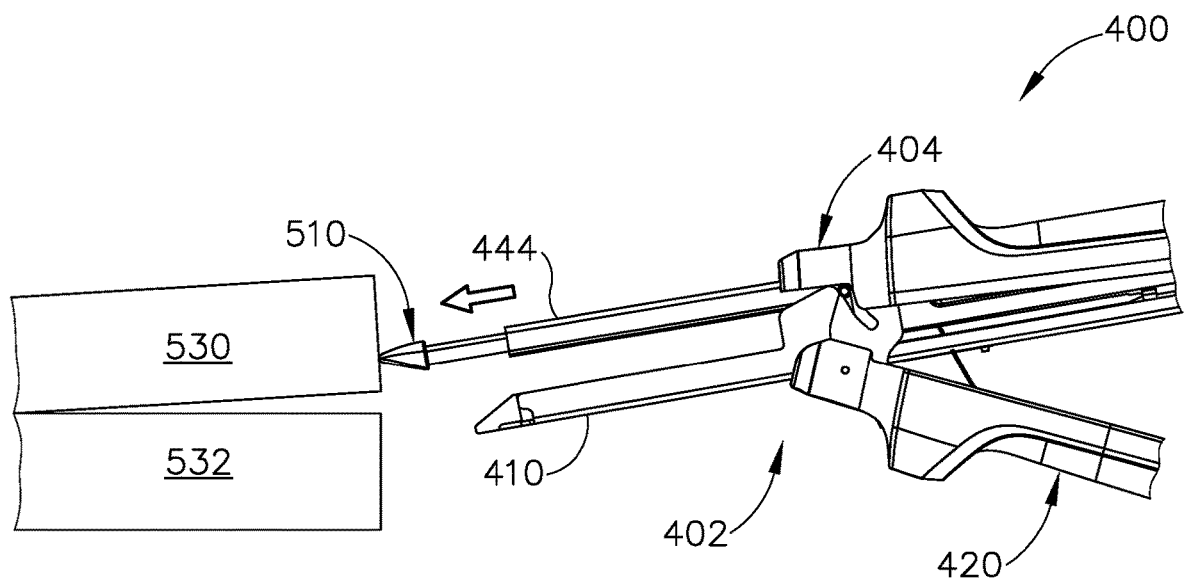
FIG. 31A depicts a schematic side elevational view of the linear surgical stapler of FIG. 22 and a pair of tubular tissue structures, showing the extendable tip member in a fully extended and being inserted into a first tubular tissue structure while the clamp lever is open.
Figure 31B:
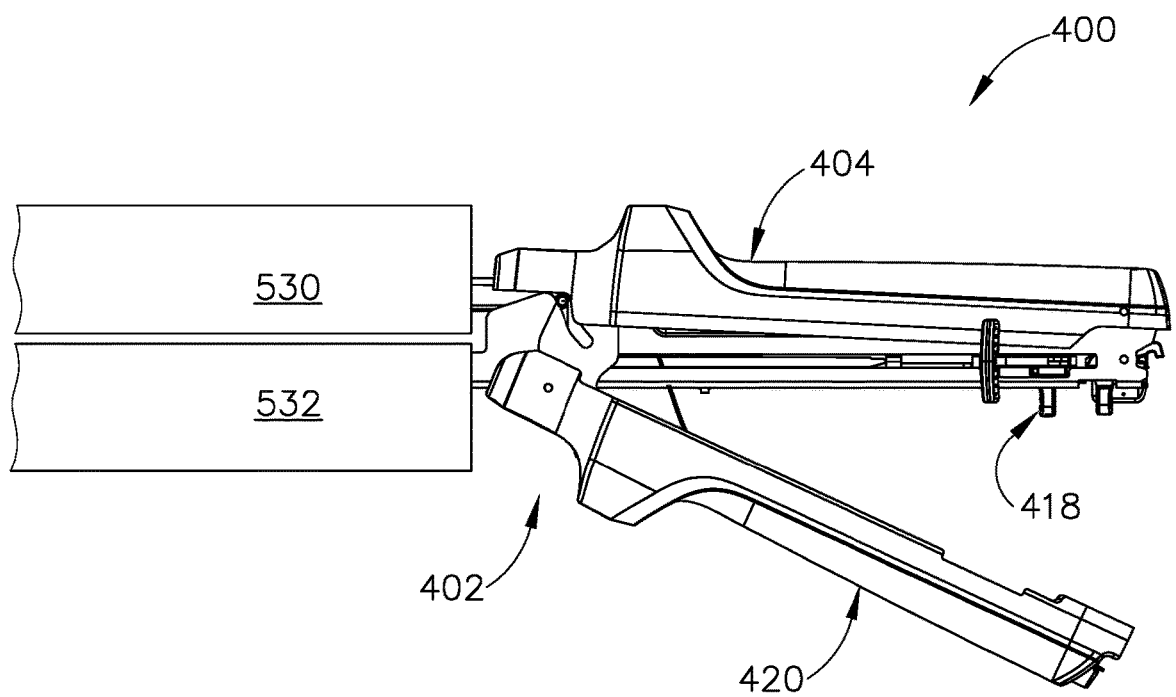
FIG. 31B depicts a schematic side elevational view of the linear surgical stapler and the tubular tissue structures of FIG. 31A, showing the distal portions of the stapler halves fully inserted into the tubular tissue structures such that the clamp lever may be closed for forming a side-by-side anastomosis.

While extendable distal tip member (510) of the present example is releasably retained in various longitudinal positions by detent bumps (520) provided within recess (518) of elongate body (512), it will be appreciated that various other types, quantities, and arrangements of releasable retaining features may be employed in other examples. Such features may be arranged on elongate body (512) and/or on another portion of anvil half (404), such as anvil channel (440) or a corresponding anvil shroud, for example as shown in FIGS. 31A and 31B. For instance, though not shown, extendable distal tip member (510) may include one or more resilient members arranged on a proximal portion of elongate body (512) and which are configured to frictionally engage a fin-like inner tab of the anvil shroud. Such an inner tab and other features of the anvil shroud may be constructed in accordance with the teachings of U.S. patent application Ser. No. 16/102,170, published as U.S. Pub. No. 2020/0046353 on Feb. 13, 2020, incorporated by reference above.

FIG. 31A shows linear surgical stapler (400) being positioned relative to first and second tubular tissue structures (530, 532) between which a side-by-side anastomosis is to be formed using stapler (400). Extendable distal tip member (510) is fully extended to provide anvil half (404) with a longer length than cartridge half (402). Accordingly, with clamp lever (420) in the open position, stapler (400) is manipulated by the user to insert extended distal tip member (510) into the inner lumen of first tissue structure (530). As shown in FIG. 31A, stapler (400) may be held at an angle by the user as needed to better align extended distal tip member (510) with a longitudinal axis of first tissue structure (530). Once extended distal tip member (510) is at least partially received within first tissue structure (530), stapler (400) may be repositioned angularly as needed to align the distal end of cartridge half (402) with a longitudinal axis of second tissue structure (532). stapler (400) is then advanced distally to insert distal jaw portion (410) of cartridge half (402) into an inner lumen of second tissue structure (532) and simultaneously advance distal jaw portion (444) of anvil half (404) within the inner lumen of first tissue structure (530). As shown in FIG. 31B, stapler halves (402, 404) are thus suitably positioned relative to tissue structures (530, 532), such that clamp lever (420) may be closed and firing assembly (418) may be advanced distally to fire stapler (400) and form a side-by-side anastomosis between tissue structures (530, 532).

F. Exemplary Alternative Extendable Distal Tip Member

Figure 32A:
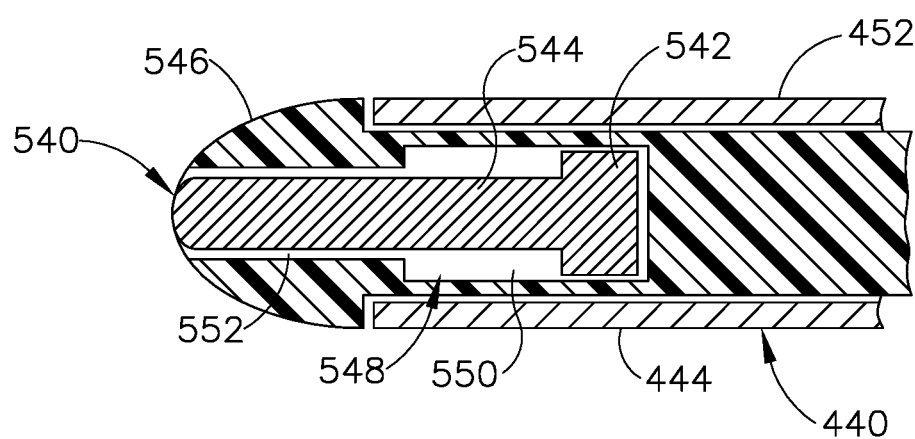
FIG. 32A depicts a side cross-sectional view of a distal portion of an anvil half having another exemplary extendable tip member, showing the extendable tip member in a fully retracted position.
Figure 32B:
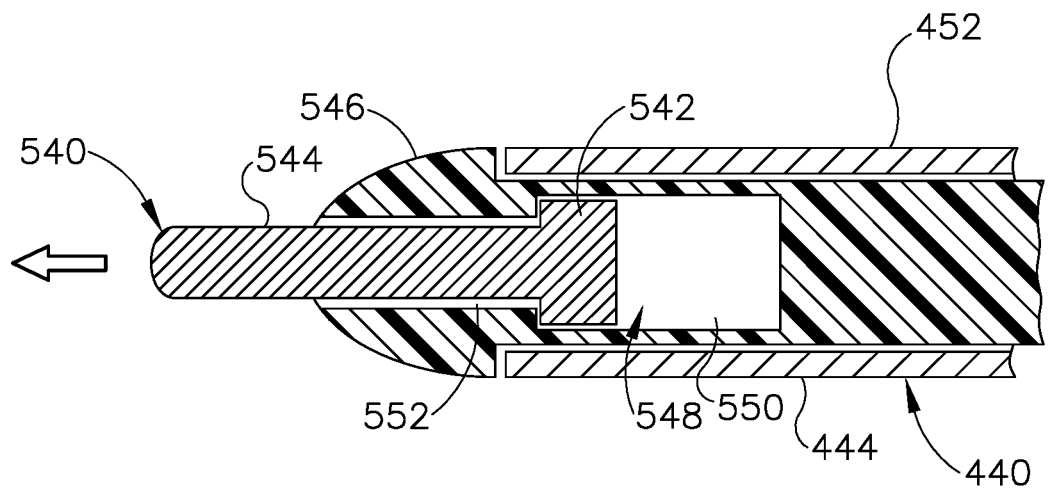
FIG. 32B depicts a side cross-sectional view of the distal portion of the anvil half of FIG. 32A, showing the extendable tip member in a fully extended position.

FIGS. 32A and 32B show distal jaw portion (444) of anvil channel (440) equipped with an exemplary alternative extendable distal tip member (540). Extendable distal tip member (540) includes a proximal head (542) and a shaft (544) extending distally from head (542) and defining distal end of tip member (540). Tip member (540) is slidable within a cavity (548) formed in a stationary insert (546) disposed within a distal end of distal jaw portion (444). Cavity (548) includes a proximal cavity portion (550) having an enlarged width sized to slidably receive proximal head (542) of tip member (540), and a distal cavity portion (552) having a narrowed width sized to slidably received shaft (544) of tip member (540).

Extendable distal tip member (540) is slidable within cavity (548) between a proximal retracted position shown in FIG. 32A in which a distal end of tip member (540) aligns with a tapered distal end of stationary insert (546), and a distal extended position shown in FIG. 32B in which the distal end of tip member (540) extends distally beyond the tapered distal end of stationary insert (546). Though not shown, tip member (540) and/or stationary insert (546) may include one or more retaining features of any suitable type configured to releasably retain tip member (540) in any one or more longitudinal positions relative to stationary insert (546). In use, tip member (540) may be extended to facilitate insertion of distal jaw portions (410, 444) of linear surgical stapler (400) into first and second tubular tissue structures (530, 532) in a manner similar to that described above in connection with FIGS. 32A and 32B.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a first elongate member having a distal portion that supports a plurality of staple forming pockets; (b) a second elongate member having a distal portion configured to receive a staple cartridge; (c) a clamp member operable to releasably clamp the first and second elongate members together; (d) a retaining member provided on one of the first elongate member or the second elongate member, wherein the retaining member is configured to releasably couple proximal ends of the first and second elongate members together with a resilient bias such that the first and second elongate members are pivotable relative to one another at the proximal ends; and (e) a decoupling mechanism, wherein the decoupling mechanism is configured to overcome the resilient bias of the retaining member and thereby decouple the proximal ends from one another in response to the first and second elongate members being pivoted away from one another.

Example 2

The surgical stapler of Example 1, wherein a portion of the decoupling mechanism is positioned to overlie and directly contact a portion of the other of the first elongate member or the second elongate member.

Example 3

The surgical stapler of any of the preceding Examples, wherein the decoupling mechanism comprises: (a) a first decoupling feature provided at the proximal end of the first elongate member, and (b) a second decoupling feature provided at the proximal end of the second elongate member, wherein the first and second decoupling features are configured to engage and thereby overcome the resilient bias of the retaining member to decouple the proximal ends in response to the first and second elongate members being pivoted away from one another.

Example 4

The surgical stapler of Example 3, wherein the first decoupling feature comprises a first projection and the second decoupling feature comprises a second projection that extends transversely to the second projection.

Example 5

The surgical stapler of any of Examples 3 through 4, wherein the first decoupling feature comprises a first stop tab, wherein the second projection comprises a second stop tab.

Example 6

The surgical stapler of any of Examples 3 through 5, wherein the first decoupling feature defines a distal end of the first elongate member.

Example 7

The surgical stapler of any of Examples 3 through 6, wherein the second decoupling feature defines a notch configured to receive the first decoupling feature when the first and second elongate members are pivoted away from one another.

Example 8

The surgical stapler of any of Examples 3 through 7, wherein the first and second elongate members are configured to pivot about a first pivot axis when coupled together by the retaining member, wherein the first and second elongate members are configured to pivot about a second pivot axis when the first and second decoupling features engage.

Example 9

The surgical stapler of any of Examples 3 through 8, wherein the first and second pivot axes extend laterally, wherein the second pivot axis is arranged proximal to the first pivot axis.

Example 10

The surgical stapler of any of the preceding Examples, wherein the other of the first elongate member or the second elongate member comprises a pivot projection, wherein the retaining member is configured to releasably capture the pivot projection to pivotably couple the proximal ends of the first and second elongate members.

Example 11

The surgical stapler of any of Example 10, wherein the pivot projection comprises a laterally extending pin.

Example 12

The surgical stapler of any of Examples 10 through 11, wherein the retaining member is configured to release the pivot projection in response to the first and second elongate members being pivoted away from one another.

Example 13

The surgical stapler of any of the preceding Examples, wherein the retaining member is coupled to the proximal end of the second elongate member, wherein at least a portion of the decoupling mechanism is provided at the proximal end of the first elongate member.

Example 14

The surgical stapler of any of the preceding Examples, wherein the retaining member comprises a rotatable latch member.

Example 15

The surgical stapler of any of the preceding Examples, further comprising an extendable tip arranged at a distal end of the first elongate member, wherein the extendable tip is selectively movable between a first longitudinal position and a second longitudinal position.

Example 16

A surgical stapler comprising: (a) a first elongate member having a distal portion that supports a plurality of staple forming pockets; (b) a second elongate member having a distal portion configured to receive a staple cartridge, wherein proximal ends of the first and second elongate members are configured to releasably couple together to define a first pivot axis about which the first and second elongate members are configured to pivot relative to one another through a first range of motion; (c) a clamp member operable to releasably clamp the first and second elongate members together; (d) a first decoupling feature provided on the first elongate member; and (e) a second decoupling feature provided on the second elongate member, wherein the first and second decoupling features are configured to cooperate to define a second pivot axis about which the first and second elongate members are configured to pivot relative to one another through a second range of motion, wherein the first and second elongate members are configured to remain pivotably coupled while pivoting through the first range of motion about the first pivot axis, wherein the first and second elongate members are configured to decouple in response to pivoting through the second range of motion about the second pivot axis.

Example 17

The surgical stapler of Example 16, wherein the second pivot axis is located proximal to the first pivot axis.

Example 18

The surgical stapler of any of Examples 16 through 17, wherein the first decoupling feature comprises a first stop tab, wherein the second decoupling feature comprises a second stop tab.

Example 19

A surgical stapler comprising: (a) a first elongate member having a distal portion that supports a plurality of staple forming pockets; (b) a second elongate member having a distal portion configured to receive a staple cartridge, wherein proximal ends of the first and second elongate members are configured to pivotably couple together; (c) a clamp member operable to releasably clamp the first and second elongate members together; (d) a lever feature arranged at the proximal end of one of the first elongate member or the second elongate member; and (e) a fulcrum feature arranged at the proximal end of the other of the first elongate member or the second elongate member, wherein the lever feature is configured to engage the fulcrum feature when the first and second elongate members are pivoted away from one another, wherein the proximal ends of the first and second elongate members are configured to pivotably decouple from one another in response to engagement of the lever feature with the fulcrum feature.

Example 20

The surgical stapler of Example 19, further comprising a latch member configured to releasably maintain the pivotable coupling between the proximal ends of the first and second elongate members, wherein the lever feature is configured to engage the fulcrum feature at a location proximal to a latching surface of the latch member.

Example 21

The surgical stapler of Example 3, wherein the second decoupling feature comprises a torque arm coupled to the retaining member.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on Feb. 6, 2018, issued as U.S. Pat. No. 10,631,866 on Apr. 28, 2020; U.S. application Ser. No. 15/889,370, entitled "Lockout Assembly for Linear Surgical Stapler," filed on Feb. 6, 2018, issued as U.S. Pat. No. 10,667,818 on Jun. 2, 2020; U.S. application Ser. No. 15/889,374, entitled "Features to Align and Close Linear Surgical Stapler", "filed on Feb. 6, 2018; issued as U.S. Pat. No. 10,932,781 on Mar. 2, 2021; U.S. application Ser. No. 15/889,376, entitled "Releasable Coupling Features for Proximal Portions of Linear Surgical Stapler," filed on Feb. 6, 2018, issued as U.S. Pat. No. 10,898,197 on Jan. 26, 2021; U.S. application Ser. No. 15/889,388, entitled "Firing Lever Assembly for Linear Surgical Stapler," filed on Feb. 6, 2018, issued as U.S. Pat. No. 10,874,398 on Dec. 29, 2020; U.S. application Ser. No. 15/889,390, entitled "Clamping Mechanism for Linear Surgical Stapler," filed on Feb. 6, 2018, issued as U.S. Pat. No. 10,678,819 on Jun. 23, 2020; U.S. patent application Ser. No. 16/102,170, entitled "Clamping Assembly for Linear Surgical Stapler," filed on Aug. 13, 2018, published as U.S. Pub. No. 2020/0046353 on Feb. 13, 2020; U.S. application Ser. No. 16/157,599, entitled "Anvil Assembly for Linear Surgical Stapler," filed on Oct. 11, 2018, published as U.S. Pub. No. 2020/0113561 on Apr. 16, 2020; and/or U.S. application Ser. No. 16/157,605, entitled "Closure Assembly for Linear Surgical Stapler," filed on Oct. 11, 2018, issued as U.S. Pat. No. 10,905,419 on Feb. 2, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
   (a) a first elongate member having a distal portion that supports a plurality of staple forming pockets;
   (b) a second elongate member having a distal portion configured to receive a staple cartridge;
   (c) a clamp member operable to releasably clamp the first and second elongate members together;
   (d) a retaining member provided on one of the first elongate member or the second elongate member, wherein the retaining member is configured to releasably couple proximal ends of the first and second elongate members together with a resilient bias such that the first and second elongate members are pivotable relative to one another at the proximal ends; and
   (e) a decoupling mechanism, wherein the decoupling mechanism is configured to overcome the resilient bias of the retaining member and thereby decouple the proximal ends from one another in response to the first and second elongate members being pivoted away from one another.

2. The surgical stapler of claim 1, wherein a portion of the decoupling mechanism is positioned to overlie and directly contact a portion of the other of the first elongate member or the second elongate member.

3. The surgical stapler of claim 1, wherein the decoupling mechanism comprises:
   (a) a first decoupling feature provided at the proximal end of the first elongate member, and
   (b) a second decoupling feature provided at the proximal end of the second elongate member,
   wherein the first and second decoupling features are configured to engage and thereby overcome the resilient bias of the retaining member to decouple the proximal ends in response to the first and second elongate members being pivoted away from one another.

4. The surgical stapler of claim 3, wherein the first decoupling feature comprises a first projection and the second decoupling feature comprises a second projection that extends transversely to the second projection.

5. The surgical stapler of claim 3, wherein the first decoupling feature comprises a first stop tab, wherein the second projection comprises a second stop tab.

6. The surgical stapler of claim 3, wherein the first decoupling feature defines a distal end of the first elongate member.

7. The surgical stapler of claim 3, wherein the second decoupling feature defines a notch configured to receive the first decoupling feature when the first and second elongate members are pivoted away from one another.

8. The surgical stapler of claim 3, wherein the first and second elongate members are configured to pivot about a first pivot axis when coupled together by the retaining member, wherein the first and second elongate members are configured to pivot about a second pivot axis when the first and second decoupling features engage.

9. The surgical stapler of claim 8, wherein the first and second pivot axes extend laterally, wherein the second pivot axis is arranged proximal to the first pivot axis.

10. The surgical stapler of claim 1, wherein the other of the first elongate member or the second elongate member comprises a pivot projection, wherein the retaining member is configured to releasably capture the pivot projection to pivotably couple the proximal ends of the first and second elongate members.

11. The surgical stapler of claim 10, wherein the pivot projection comprises a laterally extending pin.

12. The surgical stapler of claim 10, wherein the retaining member is configured to release the pivot projection in response to the first and second elongate members being pivoted away from one another.

13. The surgical stapler of claim 1, wherein the retaining member is coupled to the proximal end of the second elongate member, wherein at least a portion of the decoupling mechanism is provided at the proximal end of the first elongate member.

14. The surgical stapler of claim 1, wherein the retaining member comprises a rotatable latch member.

15. The surgical stapler of claim 1, further comprising an extendable tip arranged at a distal end of the first elongate member, wherein the extendable tip is selectively movable between a first longitudinal position and a second longitudinal position.

* * * * *